US 11,896,840 B2

(12) United States Patent
Xu et al.

(10) Patent No.: US 11,896,840 B2
(45) Date of Patent: Feb. 13, 2024

(54) DEVICES AND METHODS FOR LIGHT DELIVERY

(71) Applicant: NORTHWESTERN UNIVERSITY, Evanston, IL (US)

(72) Inventors: Shuai Xu, Evanston, IL (US); Chenkai Xu, Evanston, IL (US); Hao Zhang, Evanston, IL (US); Hangbo Zhao, Evanston, IL (US); John A. Rogers, Wilmette, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 18/060,073

(22) Filed: Nov. 30, 2022

(65) Prior Publication Data
US 2023/0087102 A1  Mar. 23, 2023

Related U.S. Application Data

(63) Continuation of application No. 17/056,094, filed as application No. PCT/US2019/032831 on May 17, 2019, now Pat. No. 11,571,586.
(Continued)

(51) Int. Cl.
*A61N 5/06* (2006.01)
*A61M 37/00* (2006.01)

(52) U.S. Cl.
CPC ....... *A61N 5/0601* (2013.01); *A61M 37/0015* (2013.01); *A61N 5/062* (2013.01);
(Continued)

(58) Field of Classification Search
CPC .............. A61N 5/0601; A61N 5/062; A61N 2005/0602; A61N 2005/063;
(Continued)

(56) References Cited

U.S. PATENT DOCUMENTS

| | | | |
|---|---|---|---|
| 6,503,231 B1 * | 1/2003 | Prausnitz | A61B 5/150984 |
| | | | 604/272 |
| 2007/0129776 A1 * | 6/2007 | Robins | A61N 5/0613 |
| | | | 607/88 |

(Continued)

*Primary Examiner* — Catherine M Voorhees
*Assistant Examiner* — Roland Dinga
(74) *Attorney, Agent, or Firm* — Locke Lord LLP; Tim Tingkang Xia, Esq.

(57) ABSTRACT

Provided are conformable light delivery devices for increasing light penetration depth and related methods. The device comprises a tissue penetrating member having a distal end and a proximal end, the tissue penetrating member configured to penetrate the tissue of the patient to be inserted into the tissue, wherein the tissue penetrating member is at least partially optically transparent along a surface of the tissue penetrating member positioned between the distal end of the tissue penetrating member and the proximal end of the tissue penetrating member to provide optical transmission of at least a portion of the light through the surface of the tissue penetrating member, thereby allowing at least the portion of the light to be delivered into the tissue of the patient when the tissue penetrating member is inserted into the tissue; and a substrate that supports the tissue penetrating member.

21 Claims, 43 Drawing Sheets

Related U.S. Application Data

(60) Provisional application No. 62/673,305, filed on May 18, 2018.

(52) U.S. Cl.
CPC .......... *A61M 2037/003* (2013.01); *A61M 2037/0061* (2013.01); *A61N 2005/0602* (2013.01); *A61N 2005/063* (2013.01); *A61N 2005/0652* (2013.01); *A61N 2005/0661* (2013.01)

(58) Field of Classification Search
CPC ... A61N 2005/0652; A61N 2005/0661; A61M 37/0015; A61M 2037/003; A61M 2037/0061
See application file for complete search history.

(56) References Cited

U.S. PATENT DOCUMENTS

| | | | | |
|---|---|---|---|---|
| 2011/0009737 A1* | 1/2011 | Manstein | ............... | A61M 37/00 604/21 |
| 2012/0095533 A1* | 4/2012 | Wang | ................... | A61N 5/0613 607/89 |
| 2013/0331992 A1* | 12/2013 | Subramaniam | ....... | B24B 41/062 700/266 |

* cited by examiner

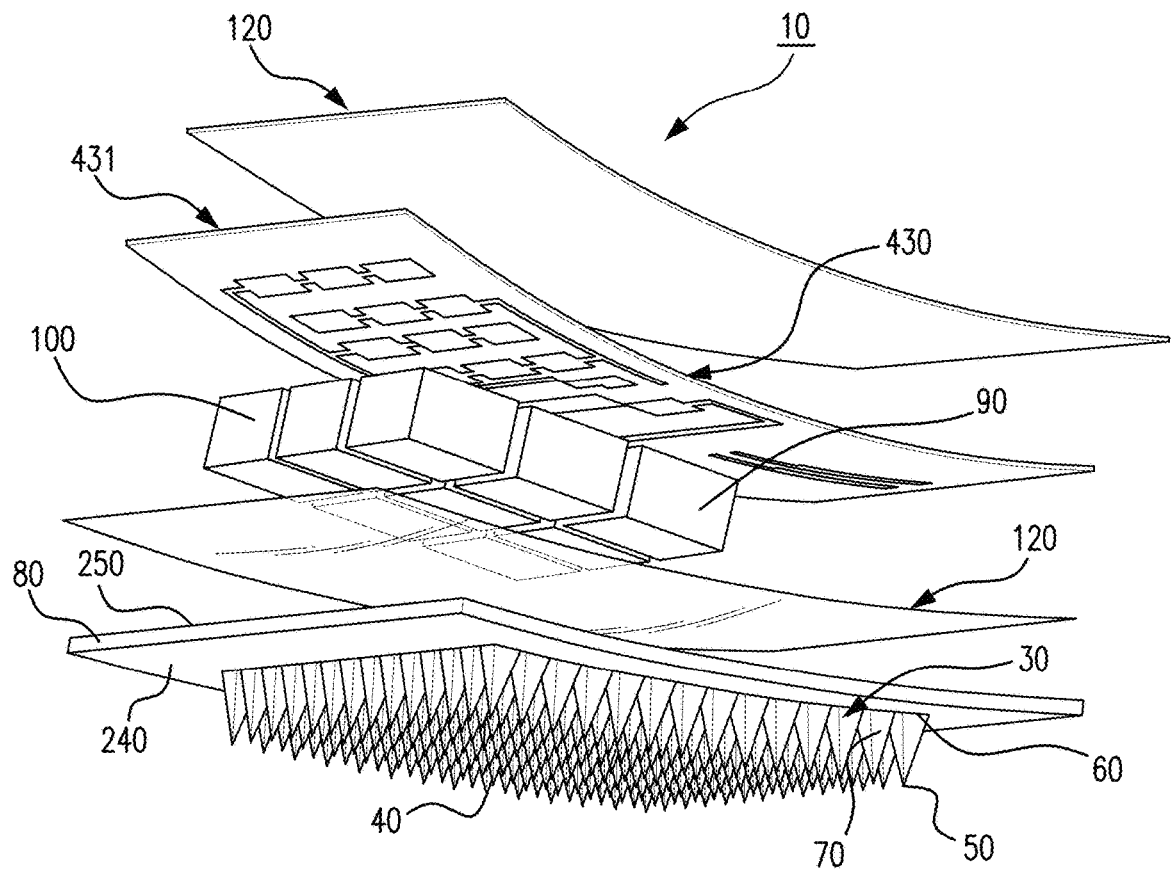
FIG. 1A
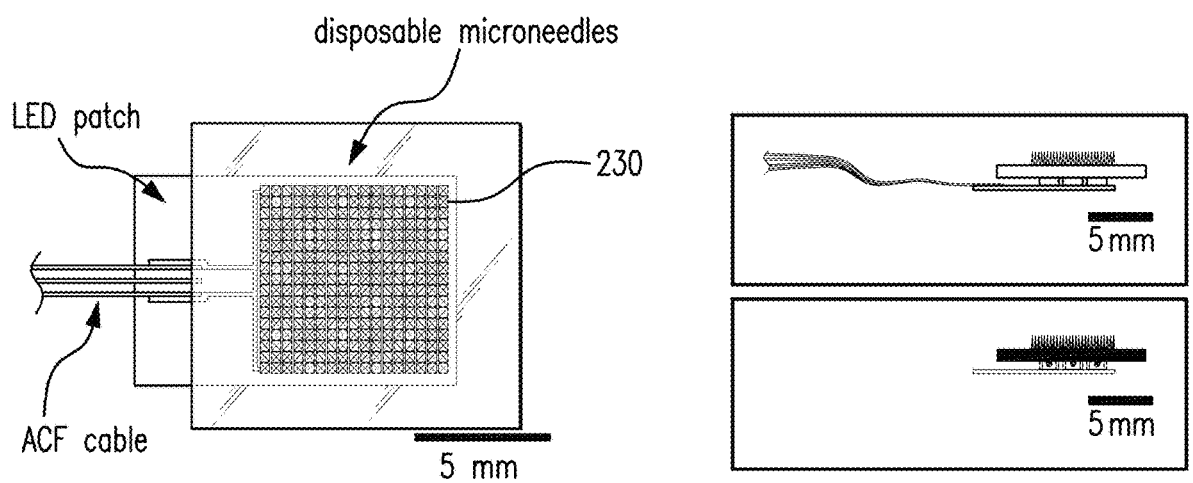
FIG. 1B
FIG. 1C

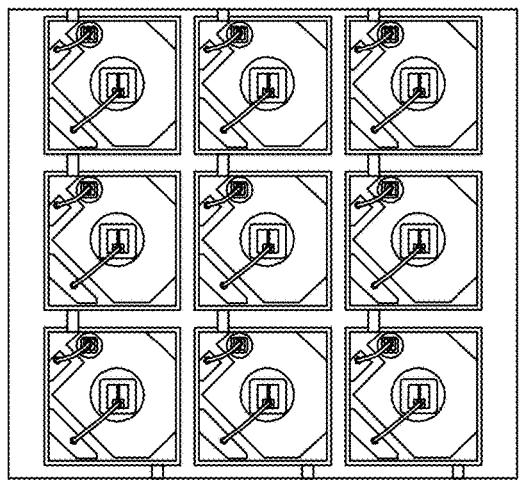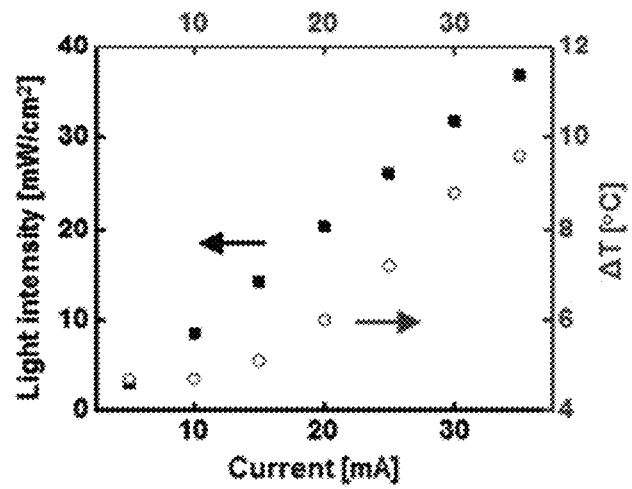
FIG. 2A  FIG. 2B
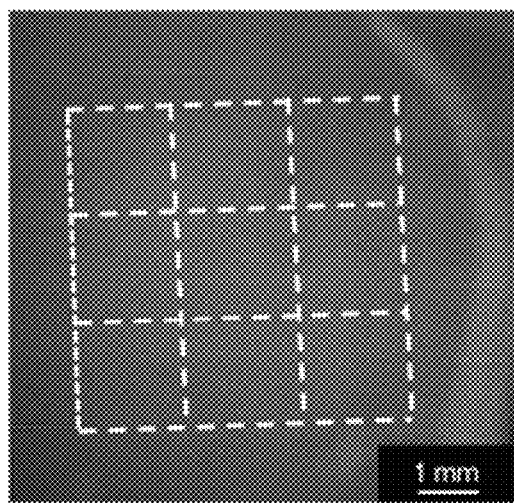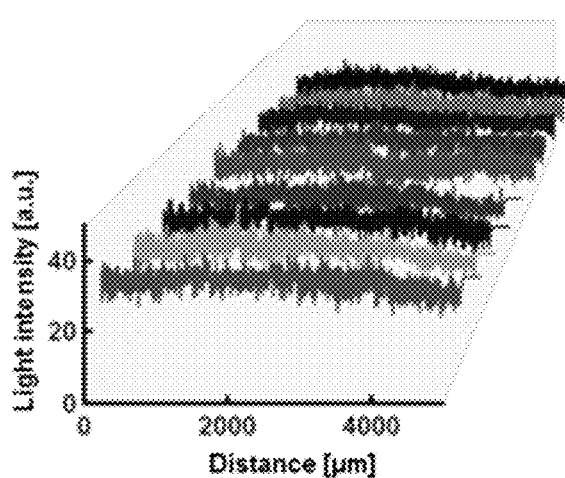
FIG. 2C  FIG. 2D

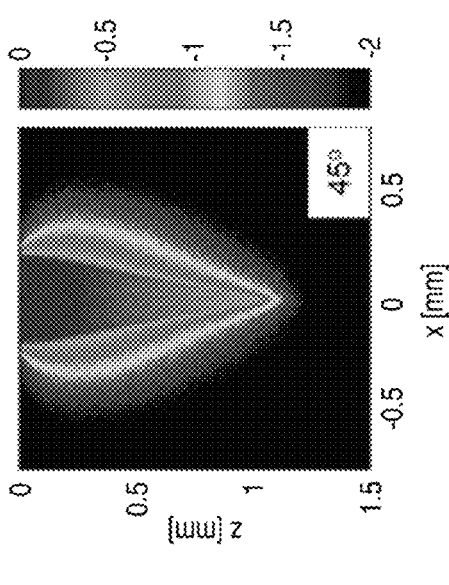
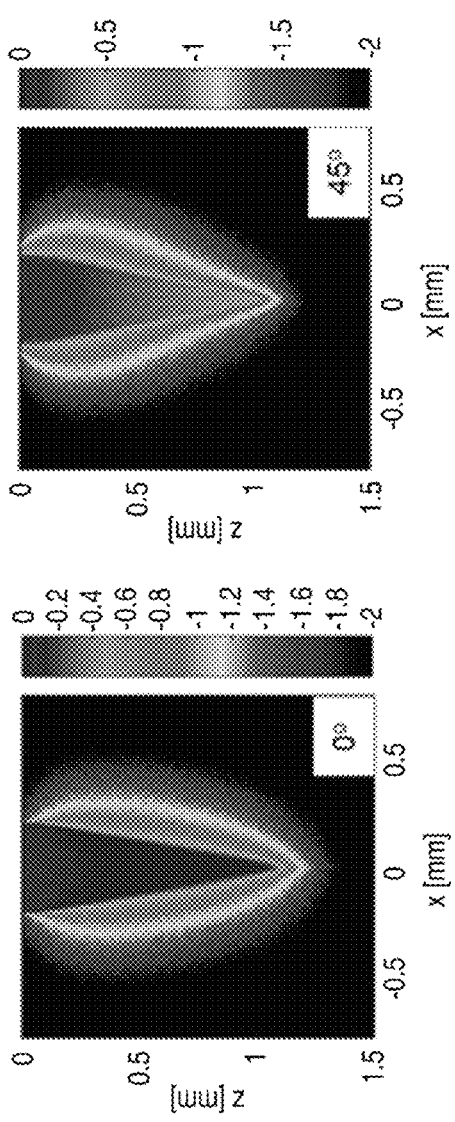
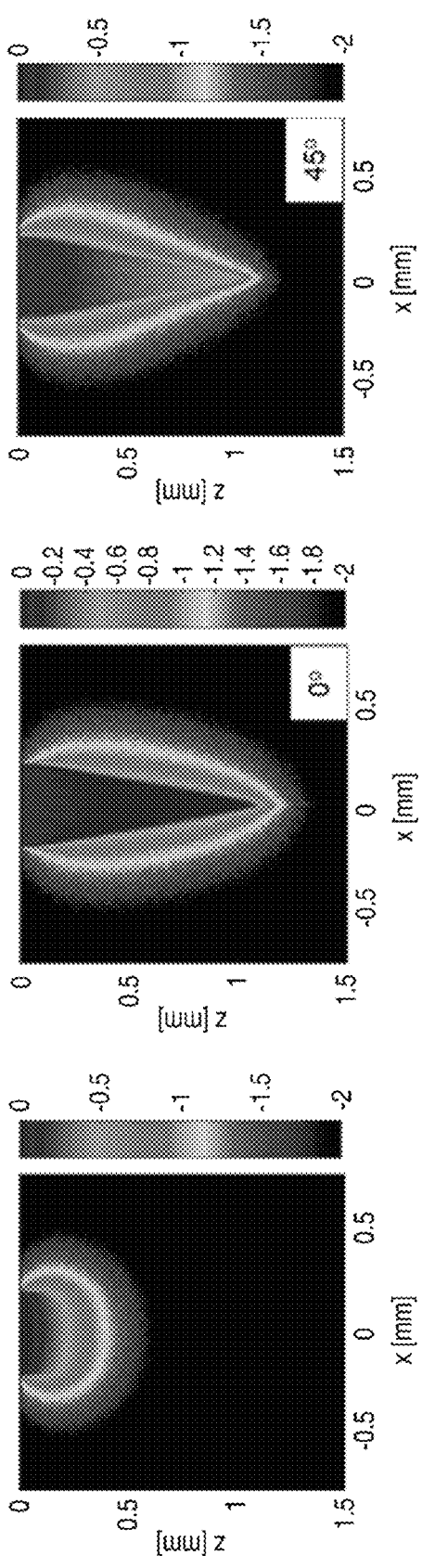
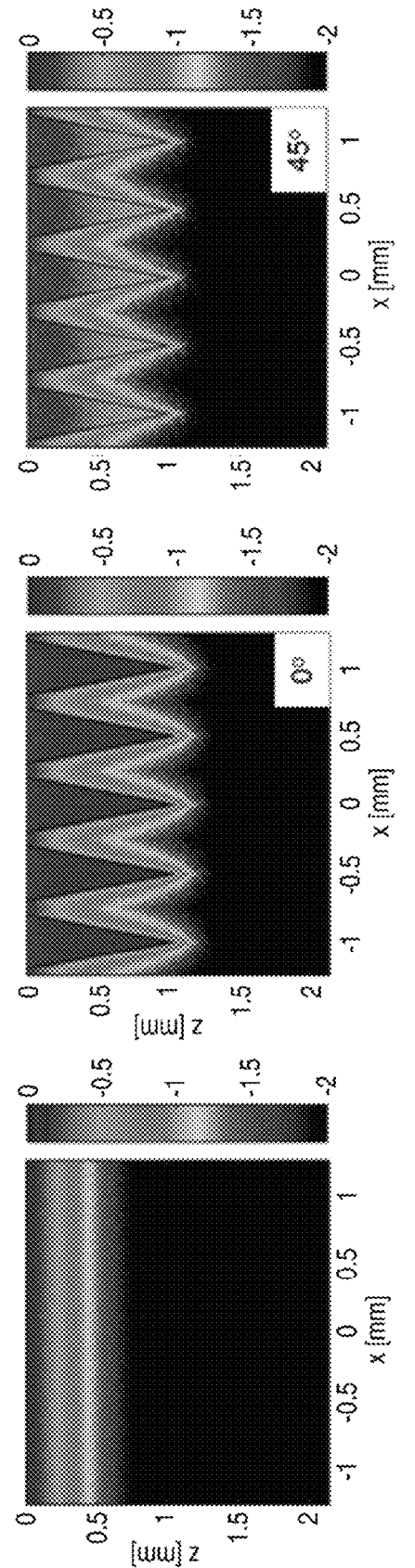
FIG. 5A FIG. 5B FIG. 5C
FIG. 5D FIG. 5E FIG. 5F

| Region | Specimens (n) | Epidermis (μm) | Dermis (μm) | E + D (μm) | E/(E + D) (%) |
| --- | --- | --- | --- | --- | --- |
| Forehead | 14 | 93.6 ± 22.3 | 788.2 ± 145.6 | 865.9 ± 136.8 | 10.6 |
| Eyelid | 28 | 54.4 ± 9.6 | 469.2 ± 119.7 | 521.2 ± 115.8 | 7.5 |
| Cheek | 28 | 98.2 ± 26.7 | 1,076.6 ± 225.0 | 1,141.1 ± 292.3 | 8.3 |
| Chin | 15 | 84.0 ± 23.3 | 763.9 ± 317.1 | 857.1 ± 247.8 | 9.9 |
| Postauricular r. | 18 | 67.9 ± 15.1 | 645.1 ± 215.3 | 712.9 ± 213.1 | 9.5 |
| Neck (anterior) | 14 | 91.1 ± 21.8 | 1,318.2 ± 364.2 | 1,408.0 ± 362.1 | 6.4 |
| Supraclavicular r. | 6 | 62.9 ± 16.1 | 706.8 ± 211.7 | 770.0 ± 220.5 | 8.1 |
| Axilla | 12 | 70.6 ± 24.7 | 940.3 ± 176.2 | 1,011.1 ± 178.1 | 6.9 |
| Chest | 18 | 98.5 ± 37.2 | 1,337.9 ± 332.3 | 1,438.5 ± 319.7 | 6.8 |
| Abdomen | 29 | 79.4 ± 33.9 | 1,248.4 ± 262.5 | 1,331.6 ± 254.2 | 6.0 |
| Back | 23 | 76.8 ± 25.9 | 1,941.6 ± 321.1 | 1,976.9 ± 395.1 | 3.7 |
| Inguinal r. | 19 | 77.8 ± 33.5 | 548.0 ± 266.2 | 625.9 ± 273.4 | 12.4 |
| Buttock | 14 | 137.7 ± 54.5 | 1,585.5 ± 536.3 | 1,721.4 ± 555.1 | 7.9 |
| Penis | 11 | 31.2 ± 5.7 | 514.8 ± 145.0 | 546.0 ± 141.9 | 5.7 |
| Front of arm | 11 | 69.2 ± 21.9 | 943.4 ± 235.6 | 1,012.6 ± 233.3 | 6.8 |
| Back of arm | 14 | 83.5 ± 36.2 | 1,030.4 ± 327.8 | 1,171.8 ± 379.3 | 7.4 |
| Front of forearm | 17 | 74.1 ± 25.4 | 1,020.4 ± 208.5 | 1,133.1 ± 214.7 | 6.7 |
| Back of forearm | 8 | 102.1 ± 34.0 | 1,077.4 ± 161.5 | 1,182.0 ± 165.0 | 8.7 |
| Dorsum of hand | 12 | 189.2 ± 63.1 | 932.9 ± 121.9 | 1,065.0 ± 130.4 | 16.8 |
| Palm | 11 | 600.9 ± 96.8 | 745.6 ± 163.5 | 1,349.4 ± 189.5 | 44.6 |
| Front of thigh | 17 | 87.4 ± 27.7 | 1,058.1 ± 147.6 | 1,144.0 ± 156.2 | 8.2 |
| Lateral thigh | 18 | 94.8 ± 23.6 | 1,217.6 ± 318.3 | 1,331.9 ± 333.5 | 7.2 |
| Back of thigh | 14 | 102.3 ± 48.6 | 1,006.5 ± 219.7 | 1,118.5 ± 178.1 | 9.2 |
| Anterior leg | 20 | 91.2 ± 25.8 | 921.5 ± 194.3 | 1,016.0 ± 219.8 | 9.0 |
| Lateral leg | 22 | 109.2 ± 18.3 | 1,013.4 ± 307.2 | 1,122.8 ± 208.4 | 9.7 |
| Back of leg | 15 | 129.6 ± 44.1 | 981.6 ± 148.2 | 1,052.4 ± 261.3 | 11.6 |
| Dorsum of foot | 13 | 163.1 ± 18.6 | 1,001.1 ± 259.2 | 1,164.4 ± 280.9 | 14.0 |
| Sole | 11 | 637.1 ± 186.0 | 931.9 ± 411.2 | 1,569.0 ± 582.7 | 40.6 |

FIG. 25

Heat insulated and opaque at the top (0.1 mm) of the needle with thicker silicone coating -> protects epidermis from injury and post-inflammatory hyperpigmentation Heat conductive and transparent bottom (0.1 - 0.5 mm) without coating -> allows light delivery Length: 1 mm; Size: 400 µm; Pitch: 600 µm

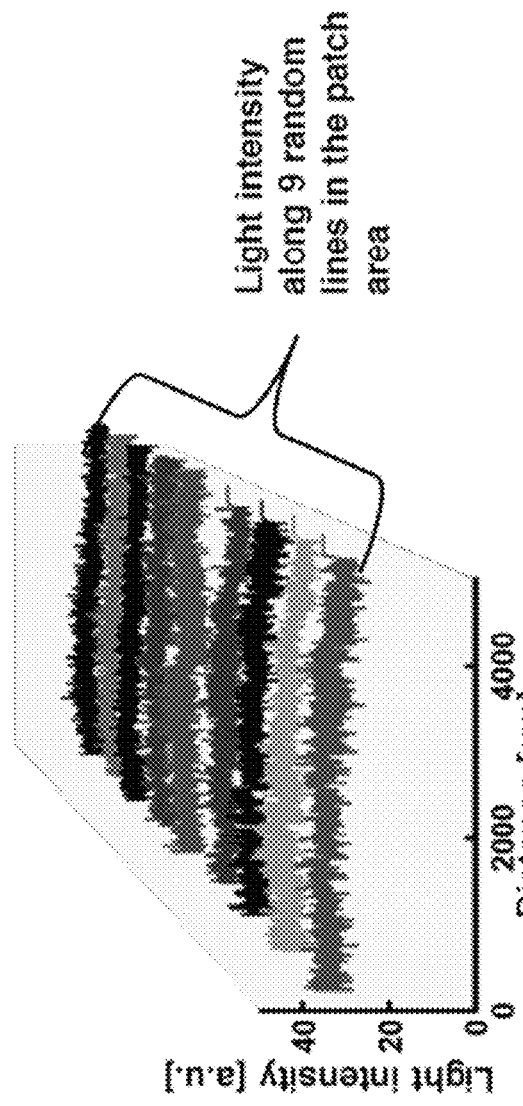
FIG. 41B
FIG. 41A
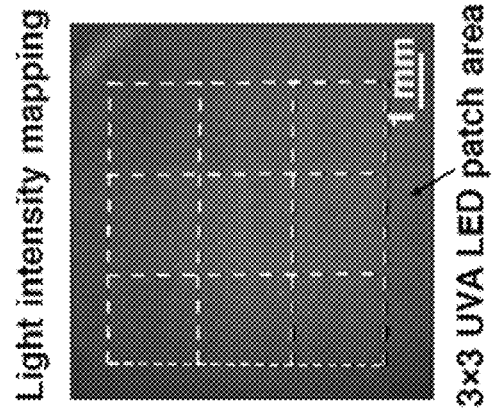
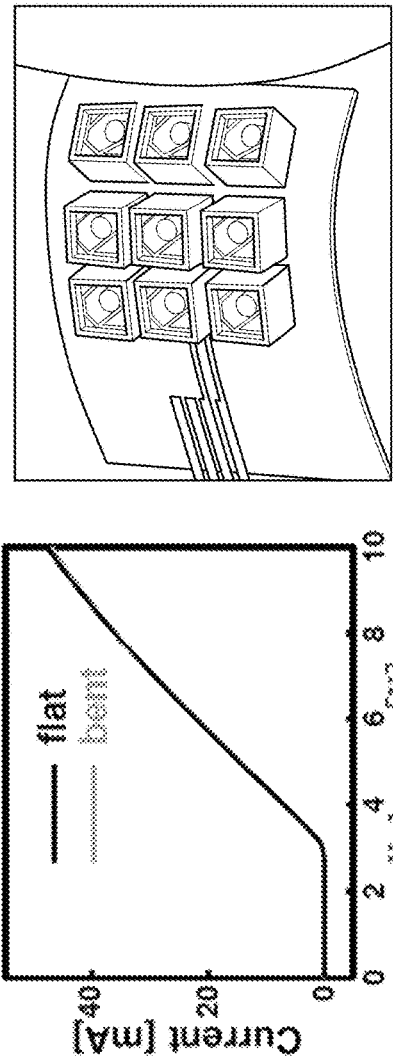
FIG. 41E
FIG. 41D
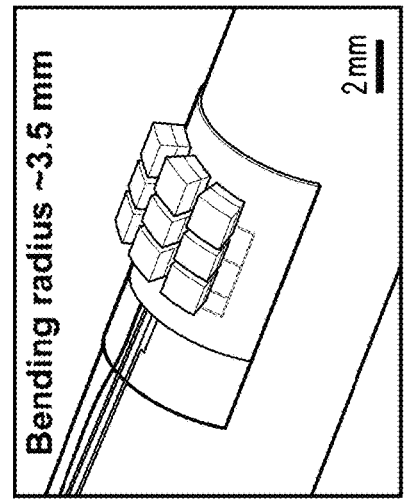
FIG. 41C

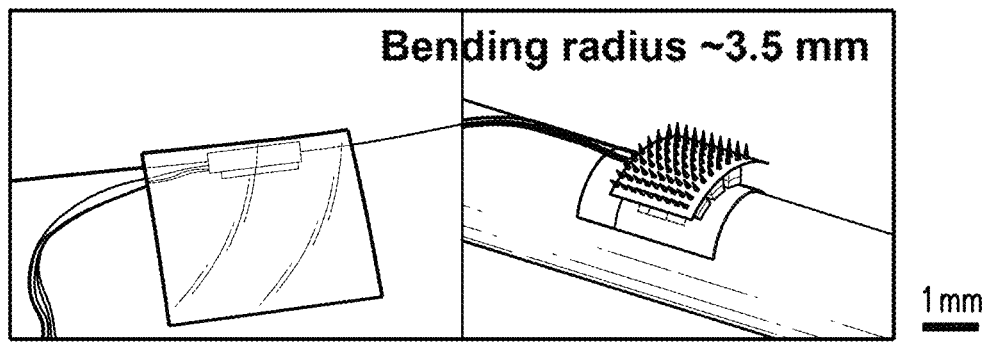
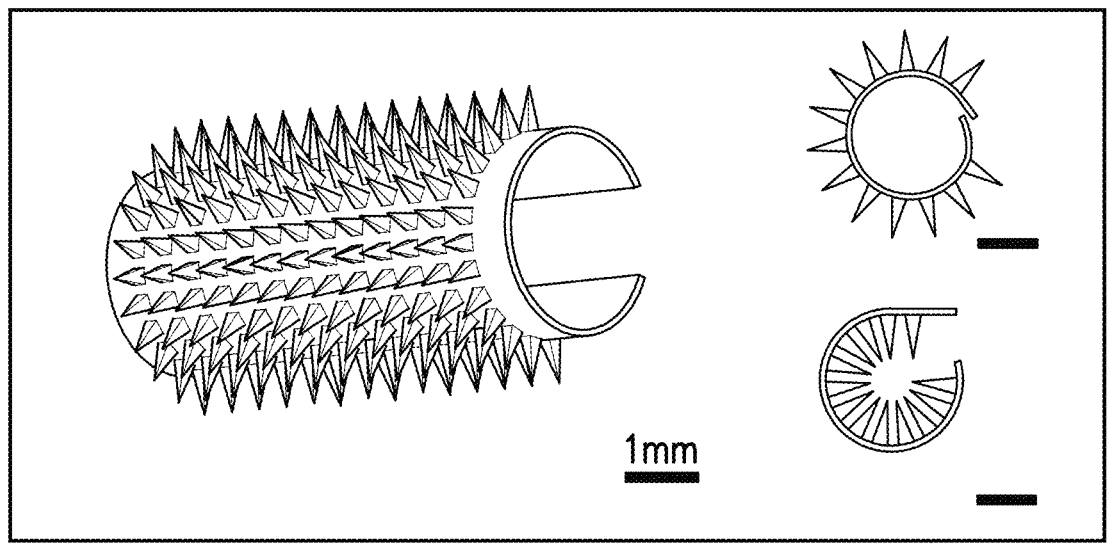
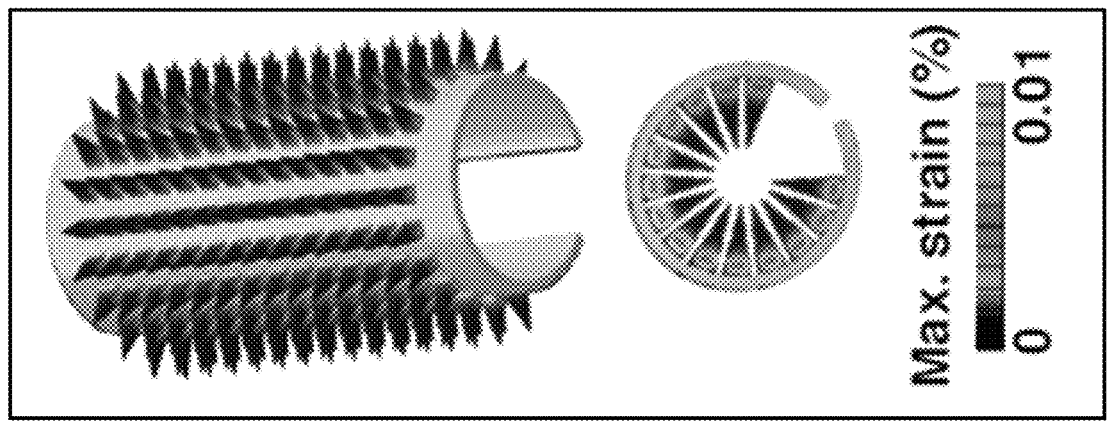
FIG. 42

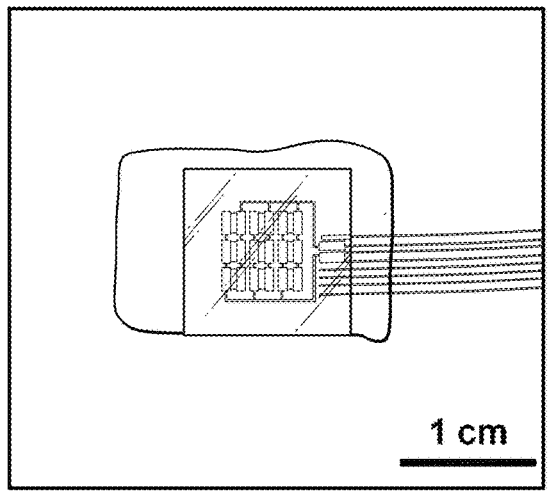
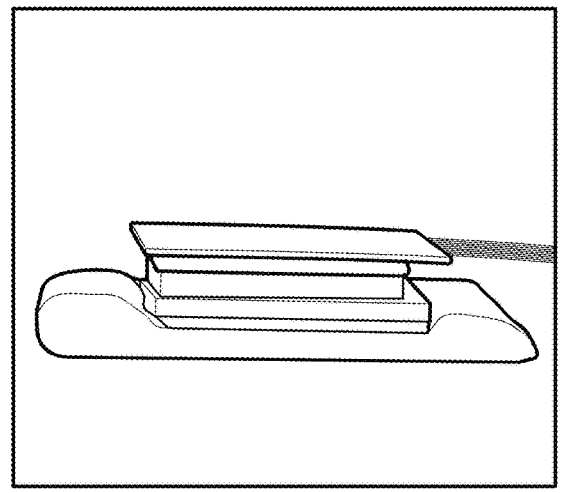
FIG. 46A
FIG. 46B
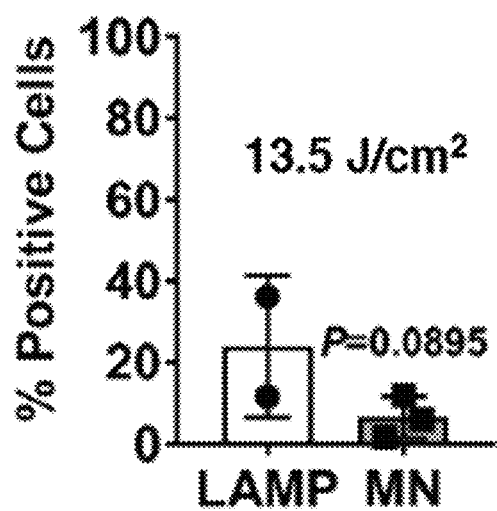
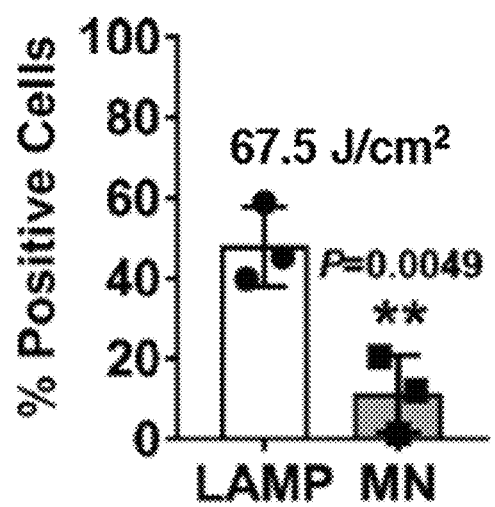
FIG. 46C
FIG. 46D

DEVICES AND METHODS FOR LIGHT DELIVERY

CROSS-REFERENCE TO RELATED APPLICATIONS

This application is a continuation application of U.S. patent application Ser. No. 17/056,094, filed Nov. 17, 2020, now allowed, which is a U.S. national entry of PCT Patent Application Serial No. PCT/US2019/032831, filed May 17, 2019, which itself claims priority to and the benefit of U.S. Provisional Patent Application Ser. No. 62/673,305 filed May 18, 2018, which are incorporated by reference in their entireties.

BACKGROUND OF INVENTION

Provided herein are various devices and methods for providing controlled light delivery in a manner that increases light penetration depth relative to a surface, including in biological tissues. It can be particularly challenging to provide reliable and uniform light intensity beneath a tissue surface without surgical implantation and/or invasive introduction of light sources, particularly as the desired optical wavelengths may tend to have extremely limited penetration depth. Furthermore, biological surfaces tend to have complex surface shapes, including time-dependent and force-dependent shapes, such as for the skin.

There are other applications where controlled light delivery is desired. For example, in the context of interventional cardiology—UVA-1 or visible light LEDs have the potential to offer therapeutic value. For instance, UVA-1 and red-light LEDs (wavelength 600-700 nm) have been shown to cause vasodilation in blood vessels. Thus, deployment of micro-LEDs on balloon catheters, guidewires, and stents (peripheral, venous, arterial) would hold potential value as new therapeutic modality to prevent vessel stenosis or to increase flow transiently in the setting of acute ischemia.

Furthermore, phototherapy is the standard of care for a wide range of dermatological conditions, with an estimated (as of 2016), total market/device size of about $500 million USDs. The opportunity here is to provide a significant improvement over existing phototherapy systems to enable the faster and more efficacious treatment of skin diseases. In addition, the ability to deliver therapeutic light deeper—conditions previously not conducive to phototherapy (e.g. scars, keloids) is relevant.

For at least these reasons, there is a need for augmented forms of light therapy that is more efficacious, faster in delivering therapeutic response, affordable, and that can be used outside the clinical setting, such as for home use. Such a system provides a significant therapeutic advance, including ensuring reliable and relatively deep light delivery in a package that is easy-to-use and comfortable, thereby increasing the likelihood of patient protocol adherence.

SUMMARY OF THE INVENTION

The devices provided herein address the above problems by providing specially configured light waveguides in the form of tissue penetrating members that can conform to various curvilinear systems. For example, flexible optical light sources may be supported by a top surface of a flexible substrate. The bottom surface of the flexible substrate may support a microarray of tissue penetrating members. The optical light sources may be in optical communication with the microarray of tissue penetrating members, so that during use the activated light sources provide light to the penetrating members, which in turn provide light to the surrounding tissue.

The devices provided herein may be described as having a light source component and a microarray of tissue penetrating member component. The light source component may be reusable, and the tissue penetrating member component single use or disposable, such as by a removable connection to the substrate that supports the components.

The devices and methods are particularly suited for providing light penetration through otherwise optically challenging surfaces, including the skin, an internal tissue, a blood vessel, and any other tissue where controlled light intensity is desired.

The devices provided herein offer a completely new treatment modality for a range of medical conditions by allowing for deeper delivery of therapeutic light. The technology can be utilized as a single standalone system (therapeutic LEDs in the UV, visible light, IR, and NIR spectrums) or as an adjuvant (microneedles alone) to enhance light penetration from a separate light source. Thus, this technology can be used as a disposable component for single phototherapy sessions.

The underlying concepts can be deployed in interventional cardiology or implantable systems to treat various conditions where deeper delivery of therapeutic light would be beneficial.

Unique aspects of the devices and methods provided herein include relatively stiffer needles, such as made of PLGA, to facilitate enhanced penetration in disease, thickened skin. Furthermore, UV delivery is enhanced; although the devices and methods provided herein are compatible with a range of wavelengths, including visible light. UV light, however, has demonstrated far higher dissipation with depth compared to light in the visible portion of the spectrum.

In addition, the devices provided herein are flexible—where the PLGA microneedles can bend allowing conformable contact with the skin and can be described as being an integrated system. For example, a top layer of LEDs embedded within a flexible substrate that rests on top of the microneedles. This enables a complete end-to-end system.

Provided is a conformable light delivery device for increasing light penetration depth comprising: a microarray of tissue penetrating members, each member having a distal end and a proximal end, wherein the tissue penetrating members are at least partially optically transparent to provide optical transmission through a surface that extends between the distal and proximal ends of each tissue penetrating member; and a substrate that supports the tissue penetrating members. any of the substrates described herein may be characterized as a flexible substrate to Also provided is a conformable light delivery device for increasing light penetration depth comprising: a microarray of tissue penetrating members having a distal end and a proximal end, wherein the tissue penetrating members are at least partially optically transparent over a range of wavelengths to provide optical transmission through a surface that extends between the distal and proximal ends of each tissue penetrating member; a flexible substrate having a top surface and a bottom surface, wherein the bottom surface supports the tissue penetrating members; a plurality of optical sources supported by the flexible substrate top surface; an electronic circuit electrically connected to the plurality of optical sources; and an encapsulation layer that at least partially encapsulates the plurality of optical sources and the electronic circuit.

Also provided is a method of using any of the devices described herein to provide light to a tissue. Also provided is a method of making any of the devices described herein.

Representative examples of the instant invention include, but are not limited to:

1. A conformable light delivery device for increasing light penetration depth in a tissue comprising: a microarray of tissue penetrating members, each member having a distal end and a proximal end, wherein the tissue penetrating members are at least partially optically transparent to provide optical transmission through a surface that extends between the distal and proximal ends of each tissue penetrating member; and a substrate that supports the tissue penetrating members, wherein the substrate is optionally a flexible substrate.

2. The light delivery device of example 1, further comprising an optical source in optical communication with the microarray of tissue penetrating members.

3. The light delivery device of example 2, wherein the optical source comprises a plurality of LEDs.

4. The light delivery device of any of examples 2 or 3, wherein the optical source has an emission maximum in a visible range of the electromagnetic spectrum.

5. The light delivery device of any of examples 2 or 3, wherein the optical source has an emission maximum in a UV range of the electromagnetic spectrum.

6. The light delivery device of example 5, wherein the emission maximum is between 100 nm and 400 nm.

7. The light delivery device of any of examples 2-6, wherein the optical source delivers at least 0.1 mW/cm$^2$ and/or at least 10 mJ/cm$^2$ to a tissue during use.

8. The light delivery device of any of examples 1-7, wherein the microarray and optical source are integrated or removably connected to each other.

9. The light delivery device of any of examples 2-8, wherein the optical source is at least partially encapsulated in a transparent encapsulation layer.

10. The light delivery device of any of examples 1-9, wherein the microarray of tissue penetrating members are configured to penetrate skin during use and to increase a penetration depth of UV light into tissue by at least a factor of 1.1 compared to UV light exposed to the skin without the microarray of tissue penetrating members.

11. The light delivery device of any of examples 1-10, wherein each tissue penetrating member transmits at least 90% of ultraviolet light or a desired subrange thereof.

12. The light delivery device of any of examples 1-11, wherein the microarray of tissue penetrating members corresponds to an array of microneedles 13. The light delivery device of example 12, wherein the microneedles have a geometrical shape that is tetrahedral, square, pyramidal or conical.

14. The light delivery device of any examples 1-13, wherein the tissue penetrating members have a length that is greater than or equal to 100 µm and less than or equal to 10 mm and/or a pitch distance that is greater than or equal to 100 µm and less than or equal to 1 mm.

15. The light delivery device of any of examples 1-14, wherein the tissue penetrating members have an optical property that is optically matched to an optical light source, wherein the optical property is selected from the group consisting of: optical transmission/output light spectrum; index of refraction; scattering, absorption, emissivity, fluorescence, heat generation; and thermal relaxation time of tissue.

16. The light delivery device of any of examples 1-15, wherein the tissue penetrating members are tapered, with a maximum width at the proximal end and a minimum width or a tip at the distal end.

17. The light delivery device of example 16, wherein the minimum width is between 5 µm and 50 µm and the maximum width between 100 µm and 1 mm 18. The light delivery device of any of the above examples, wherein ultra-violet light is transmitted from the tissue penetrating members through all side surfaces and the distal end to tissue surrounding the tissue penetrating members.

19. The light delivery device of any of the above examples, wherein the tissue penetrating members are formed of a biocompatible material, wherein the biocompatible material optionally comprises a polymer.

20. The light delivery device of any of the above examples, wherein the tissue penetrating members are formed of a material selected from the group consisting of: poly(D,L-lactide-co-glycolide) (PLGA), polylactic acid, poly-methyl-methacrylate, PDMS, and carboxymethyl cellulose.

21. The light delivery device of any of the above examples, wherein the device is flexible with a bulk bending stiffness selected so that the device is capable of conforming to a tissue surface during a light therapy application to reduce surface reflection and increase light delivery to a target.

22. The light delivery device of example 21, wherein the reduced surface reflection is by the substrate having a composition that provides and index of refraction that is within 10% of an index of refraction of a material from which the tissue penetrating members are formed.

23. The light delivery device of any of the above examples, further comprising an optical dispersion element in optical communication with the tissue penetrating members to increase light dispersion and increase light intensity uniformity to a tissue that surrounds the tissue penetrating members during use, wherein the optical dispersion element comprises one or more of: a roughened tissue penetrating member surface; an optical coating; a diffraction grating; a waveguide; a chemically-modified tissue penetrating member surface; a patterned optically opaque layer; lenses; or upconverting or downconverting phosphors.

24. The light delivery device of any of the above examples, having a light transmission footprint that is greater than or equal to 0.2 cm$^2$.

25. The light delivery device of any of the above examples, wherein the substrate has a bottom surface that supports the microarray of tissue penetrating members and a top surface that supports a plurality of optical sources.

26. The light delivery device of example 25, wherein the microarray of tissue penetrating members are optically aligned with the plurality of optical sources to provide substantially uniform light intensity to a tissue that surrounds the microarray of tissue penetrating members.

27. The light delivery device of any of the above examples, wherein the microarray of tissue penetrating members is formed from a microarray material having an index of refraction that is matched to an index of refraction of the substrate.

28. The light delivery device of any of the above examples, wherein the tissue penetrating members are solid.

29. The light delivery device of any of 1-27, wherein the tissue penetrating members are: hollow; solid with cavities; or solid with embedded liquid.

30. The light delivery device of any of examples 1-29, further comprising a bioactive agent.

31. The light delivery device of example 30, wherein the bioactive agent comprises a coating on at least a portion of a surface of the penetrating members.

32. The light delivery device of any of the above examples, having a tissue penetrating member occupancy fraction (area of member base to area of substrate) that is greater than or equal to 10%.

33. The light delivery device of any of the above examples, wherein the tissue penetrating members have an effective Young's modulus selected to withstand stresses during insertion through a tissue surface without substantial deformation in a direction that decreases penetration depth in the tissue.

34. The light delivery device of any of the above examples, wherein the device further comprises a bioactive agent releasably connected to the microarray of tissue penetrating members, wherein the bioactive agent is activated by light transmitted by the microarray of tissue penetrating members.

35. The light delivery device of any of the above examples, wherein the device is integrated in a stent, a guidewire, a catheter, a balloon catheter for use in a blood vessel; a subdermal implant; an orthopedic implant, a prosthesis, or a neurological implant.

36. The light delivery device of example 35, wherein the device is a conformable intra-arterial or intra-venous device and comprises a plurality of LEDs in optical communication with the microarray of tissue penetrating members.

37. The light delivery device of example 36, wherein the LEDs are UV-emitting LEDs.

38. The light delivery device of example 37, wherein UV light emitted by the UV-emitting LEDs is able to cause vasodilation in blood vessels.

39. The light delivery device of example 36, wherein the tissue penetrating members have a length that is greater than or equal to 10 μm and less than or equal to 100 μm, a pitch distance that is greater than or equal to 100 μm and less than or equal to 500 μm, and a maximum width between 50 μm and 100 μm.

40. The light delivery device of any of the above examples, further comprising a light intensity modulator for controlling light intensity as a function of depth from a tissue surface.

41. The light delivery device of example 40, wherein the light intensity modulator comprises a non-transparent coating extending from the tissue penetrating members' proximal end to reduce optical light intensity to a tissue surface region.

42. The light delivery device of example 41, wherein the non-transparent coating reduces UV light transmission and the tissue surface region corresponds to an epidermal layer.

43. The light delivery device of example 40, wherein the light intensity output is focused toward or at the distal end of the tissue penetrating members.

44. The light delivery device of any of the above examples, wherein the substrate is formed of a therapeutically-beneficial material or of a therapeutic agent connected to, or supported by, the substrate.

45. The light delivery device of example 44, wherein the therapeutically-beneficial material comprises silicone and the therapeutic benefit is improvement in scar appearance.

46. The light delivery device of any of the above examples, wherein the substrate further comprises a substrate component that improves light delivery, wherein the substrate component comprises one or more of glycerol or perfluorodecalin.

47. A conformable light delivery device for increasing light penetration depth in a material comprising: a microarray of tissue penetrating members having a distal end and a proximal end, wherein the tissue penetrating members are at least partially optically transparent over a range of wavelengths to provide optical transmission through a surface that extends between the distal and proximal ends of each tissue penetrating member; a flexible substrate having a top surface and a bottom surface, wherein the bottom surface supports the tissue penetrating members; a plurality of optical sources supported by the flexible substrate top surface; an electronic circuit electrically connected to the plurality of optical sources; and an encapsulation layer that at least partially encapsulates the plurality of optical sources and the electronic circuit.

48. The conformable light delivery device of example 47, wherein the microarray and flexible substrate are disposable and replaceable.

49. A method of providing light to a tissue, the method comprising the steps of: providing any of the devices of examples 1-48; conformally contacting the microarray with a tissue surface; inserting at least a portion of the microarray of tissue penetrating members into the skin; transmitting light through the flexible substrate and the microarray of tissue penetrating members to a tissue that surrounds the microarray of tissue penetrating members.

50. The method of example 49, wherein the tissue surface corresponds to a skin surface.

51. The method of example 49 or 50, wherein the tissue surface comprises a curved surface.

52. The method of any of examples 49-51, wherein the transmitting step comprises: energizing a plurality of LEDs connected to the substrate surface, wherein the LEDs have an emission maximum in the UV range or a visible portion of the electromagnetic spectrum.

53. An injectable therapeutic light delivery device comprising: a substrate; a tissue penetrating member having a proximal end and a distal end, wherein the proximal end is supported by the substrate; a plurality of light sources optically dispersed along a member wall that extends between the member proximal and distal ends; wherein the tissue penetrating member and plurality of light sources are configured to penetrate a tissue to provide controlled subsurface light intensity to tissue that surrounds the tissue penetrating member.

54. The device of example 53 wherein the tissue penetrating member comprises a needle.

55. The device of example 54, wherein the needle comprises an optically non-transparent material, including a metal, and the optical light sources are LEDs that are distributed on a tissue-facing surface of the needle.

56. The device of example 55, wherein the LEDs are UV-emitting LEDs.

57. The device of any of examples 53-56 configured to treat cancer, including cutaneous T-cell lymphoma.

58. The device of any of examples 53-57, wherein the light delivery is of UVA or UVB light at a tissue depth that is greater than or equal to 1 cm.

59. The device of any of examples 53-58, comprising a plurality of tissue penetrating members, wherein each tissue penetrating member has a plurality of light sources optically dispersed along the member wall that extends between the member proximal and distal ends.

60. A light delivery device for delivering light to a tissue of a patient, comprising: a tissue penetrating member having a distal end and a proximal end, the tissue penetrating member configured to penetrate the tissue of the patient to be inserted into the tissue, wherein the tissue penetrating member is at least partially optically transparent along a surface of the tissue penetrating member positioned between the distal end of the tissue penetrating member and the proximal end of the tissue penetrating member to provide optical transmission of at least a portion of the light through the surface of the tissue penetrating member, thereby allowing at least the portion of the light to be delivered into the tissue of the patient when the tissue penetrating member is inserted into the tissue; and a substrate that supports the tissue penetrating member.

61. The light delivery device of example 60, comprising: a plurality of tissue penetrating members comprising the tissue penetrating member, the plurality of tissue penetrating members being configured to penetrate the tissue of the patient and being at least partially optically transparent.

62. The light delivery device of example 61, comprising: an array of microneedles comprising the plurality of tissue penetrating members.

63. The light delivery device of example 62, further comprising: an array of optical sources optically aligned with the array of microneedles.

64. The light delivery device of example 62, wherein a microneedle of the array of microneedles has a geometrical shape that is tetrahedral, square, pyramidal, or conical.

65. The light delivery device of example 61, wherein a tissue penetrating occupancy fraction of the plurality of tissue penetrating members is between 0.05 and 0.9.

66. The light delivery device of example 60, further comprising: an optical source in optical communication with the tissue penetrating member, the optical source configured to emit the light.

67. The light delivery device of example 66, wherein the optical source has an emission maximum in a visible range or an ultraviolet range of the electromagnetic spectrum.

68. The light delivery device of example 66, wherein the optical source is removably connected to the tissue penetrating member.

69. The light delivery device of example 68, comprising: a tissue contacting unit comprising the tissue penetrating member and the substrate, wherein the tissue contacting unit is disposable.

70. The light delivery device of example 60, wherein the tissue penetrating member has a length that is no less than 100 µm and that is no more than 10 mm and/or a pitch distance that is greater than or equal to 100 µm and less than or equal to 1 mm.

71. The light delivery device of example 60, wherein the tissue penetrating member is tapered, the tissue penetrating member having a maximum width at the proximal end of the tissue penetrating member and a minimum width at the distal end of the tissue penetrating member.

72. The light delivery device of example 71, wherein the maximum width of the tissue penetrating member is no less than 100 µm and is no more than 1 mm.

73. The light delivery device of example 60, wherein the tissue penetrating member is formed of a biocompatible material, wherein the biocompatible material comprises a polymer.

74. The light delivery device of example 60, wherein the tissue penetrating member is solid.

75. The light delivery device of example 60, further comprising: an optical dispersion element in optical communication with at least one tissue penetrating member, the optical dispersion element comprising at least one of: (i) a roughened tissue penetrating member surface; (ii) an optical coating; (iii) a diffraction grating; (iv) a waveguide; (v) a chemically-modified tissue penetrating member surface; (vi) a patterned optically opaque layer; (vii) lenses; or (viii) upconverting or downconverting phosphors.

77. The light delivery device of example 60, further comprising: a light intensity modulator for controlling an intensity of at least the portion of the light transmitted through the tissue penetrating member as a function of a depth of the distal end of the tissue penetrating member from a surface of the tissue.

78. The light delivery device of example 77, wherein the light intensity modulator comprises a non-transparent coating extending from the proximal end of the tissue penetrating member to a tissue surface region of the tissue penetrating member.

79. A method of delivering light to a tissue of a patient, comprising: contacting one or more tissue penetrating members of a light delivery device with the tissue of the patient; inserting the one or more tissue penetrating members into the tissue of the patient; and delivering the light through the one or more tissue penetrating members to the tissue of the patient while the one or more tissue penetrating members are inserted into the tissue of the patient.

80. The method of example 79, wherein: the light delivery device comprises an array of tissue penetrating members and an optical source; inserting the one or more tissue penetrating members into the tissue of the patient comprises: inserting the array of tissue penetrating members into the tissue of the patient; and delivering the light through the one or more tissue penetrating members to the tissue of the patient comprises: operating the optical source of the light delivery device to deliver the light through the array of tissue penetrating members.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIGS. 1A-1F. Scheme and design of an integrated wearable light (including for UVA-1) therapy device. FIG. 1A: Exploded scheme of the integrated wearable device combining a UVA LED patch with an array of tissue penetrating members formed of PLGA microneedles as a light guide. The LED patch comprises a 3 by 3 UVA LED array on a flexible polyimide substrate printed with copper circuits. The PDMS encapsulated LED patch is integrated with the biocompatible PLGA microneedle array. FIG. 1B: A photograph of the integrated device with an active area (i.e., with LED and microneedles) of about 7 by 7 mm. FIG. 1C: The cross-sectional view of the integrated device with LEDs powered on (bottom) or off (top). Scale bar is 5 mm. FIG. 1D: Schematic close up (not to scale) of a side-view cross-section of the substrate and tissue penetrating members, with various optional optical components to control optical parameters. FIG. 1E: Schematic of a top-down view cross-section at the substrate surface illustrating an array whose geometry and configuration provides for a desired footprint, in both an optical aspect and a physical aspect. FIG. 1F: schematic illustration of various geometry of the microneedles, including tetrahedral, square, pyramidal and conical. A common feature is the distal end of the microneedle goes to a minimum to facilitate tissue penetration and minimize tissue damage. The taper angle of the microneedles are exaggerated for clarity, and can be much more gentle, like a hypodermic needle, with a distal portion that tapers and a proximal portion that has substantially uniform cross-sectional dimensions.

FIGS. 2A-2D. Optical characterization of the LED patch. FIG. 2A: A photograph of the compact 3 by 3 array of optical sources, in this example UVA-1 LEDs. FIG. 2B: The dependence of output optical irradiance and temperature increase on driving current of the UVA-1 LED patch. FIG. 2C: An optical image of a 1 mm-thick Dylight 350-containing Agarose gel placed on top of the LED patch. The dashed boxes indicate the location of the 3 by 3 LED array. FIG. 2D: Measured light intensity distribution along 9 randomly selected lines inside the LED area (the boxed area in FIG. 2C), indicating a substantially uniform light intensity over the whole LED patch.

FIG. 3A: Microscopic images of pyramidal PLGA microneedle arrays with 1 mm length and various combinations of base size and spacing. From left to right, the base size (μm) and spacing (μm) for the arrays are 200/100, 400/200, 300/100, and 400/200, respectively. The MN tip radius is 10-20 μm. Scale bar=1 mm. FIG. 3B: A microscopic image of the trypan blue stained pig skin after PLGA MN insertion. FIG. 3C: Cross sectional magnetic resonance imaging (MRI) of PLGA MNs inserted in pig skin. FIG. 3D: The statistics of insertion depth of MNs (0.73±0.04 mm, n=10) in pig skin based on MRI image analysis (FIG. 3C). The MNs used for (FIGS. 3B-3D) are pyramidal shaped needles with base size=400 μm, spacing=200 μm, and length=1 mm.

FIG. 4A: (Left) A photograph of a gelatin skin phantom block placed on top of a PLGA plate without MNs. (Right) An image taken without ambient light to visualize the dissipation of 400 nm light (from a collimated LED light source placed underneath) in skin phantom. FIG. 4B: (Left) A photograph of a gelatin skin phantom block with a PLGA MN array inserted. (Right) An image visualizing the dissipation of 400 nm light (from a collimated LED light source placed underneath) in skin phantom. Inset shows the microscopic image of the same sample. Scale bar=1 mm. Each white arrow indicates a single needle.

FIGS. 5A-5F. Monte Carlo simulation of light dissipation in skin. In silico experiment of normalized light irradiance distribution (in $mW/cm^2$) in a single microneedle unit cell (FIGS. 5B, 5C) and an array of microneedles (FIGS. 5E, 5F), as well as the standard care approach without needles (FIGS. 5A, 5D). The light irradiance at the top of skin is 20 $mW/cm^2$ and the incident angle is either 0 deg. (FIGS. 5B, 5E) or ±45 deg. (FIGS. 5C, 5F). The microneedles have dimensions of 0.7 mm length, 400 μm base size and 200 μm spacing. In (FIGS. 5A-5C), the light enters the microneedles or skin from a 400 μm by 400 μm area.

FIG. 7A: A photograph of an array of UVA-1 LEDs on a thin (12.5 μm), flexible polyimide substrate. FIG. 7B: Photographs of PLGA MNs with a highly flexible handling layer as well as rigid needles. Scale bar=1 mm. FIGS. 7C, 7D: Photographs of a prototype, integrated light therapy device on the arm of a human subject.

MSH, melanocyte-stimulating hormone; mRNA, messenger RNA; TGF, transforming growth factor.

Figure 19:
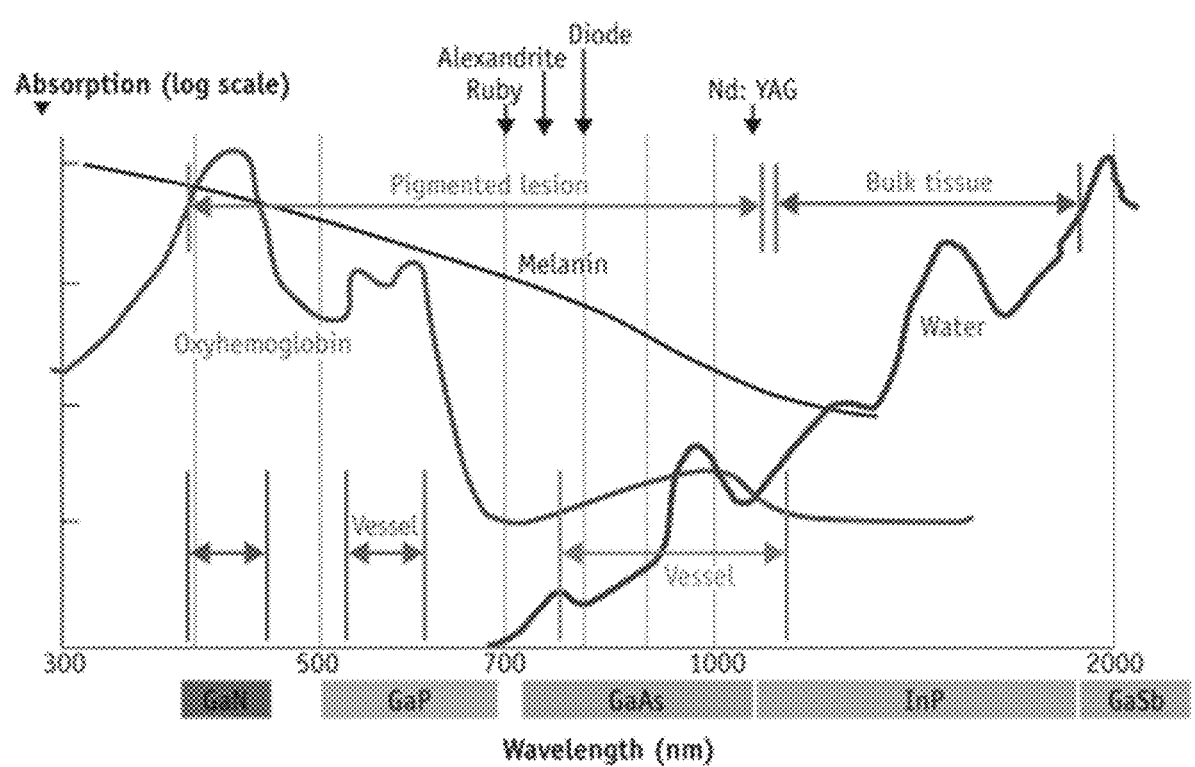

FIG. 19. Absorption wavelength ranges for various biological constituents and corresponding LED composition.

Figure 20:
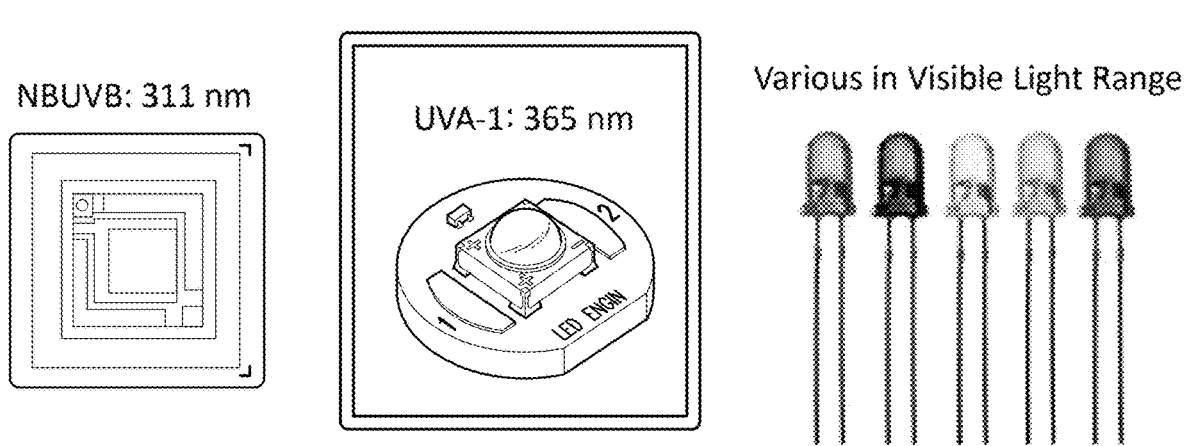

FIG. 20. Illustration of various optical light sources, including in the UVB (left—311 nm), UAA (right—365 nm) and visible (right) wavelengths.

Figure 21:
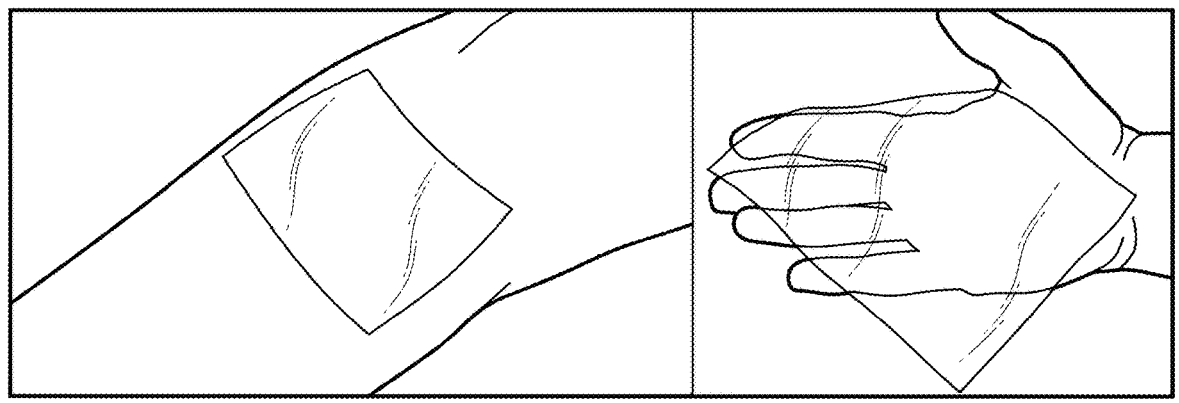

FIG. 21. Silicone Sheeting: as a substrate that can facilitate improved biological outcome, such as for wound/scar healing.

Figure 22:
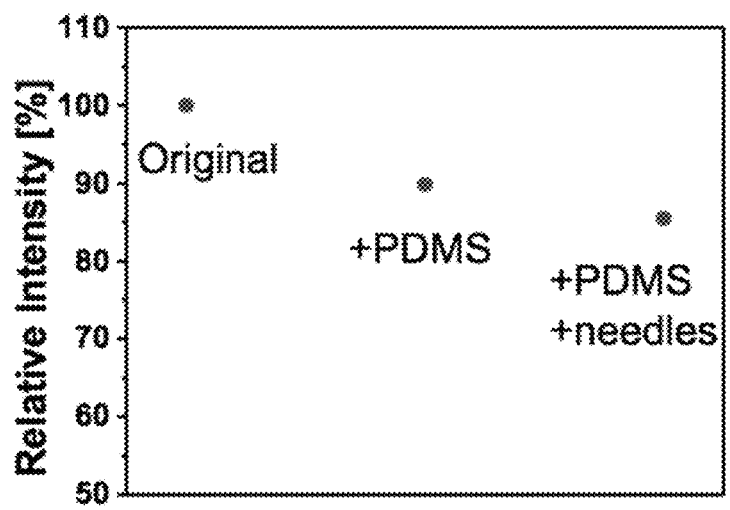

FIG. 22. Plot of relative light intensity for UV light, with PDMS and with PDMS and needles, with a corresponding reduction in light intensity of less than 15%, driven by 20 mA DC, compliance 4.0V.

Figure 23:
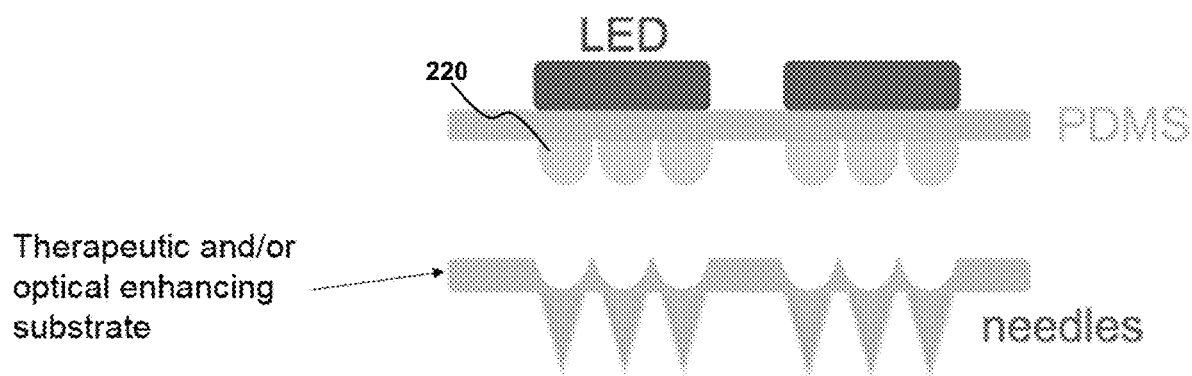

FIG. 23. Therapeutic and/or optical enhancing substrate, including with optical components to improve directed optical path for light between the lights sources and underlying tissue penetrating members; UVC and UVB do not pass through the epidermis, and UVA only partially penetrates the dermis.

Figure 24:
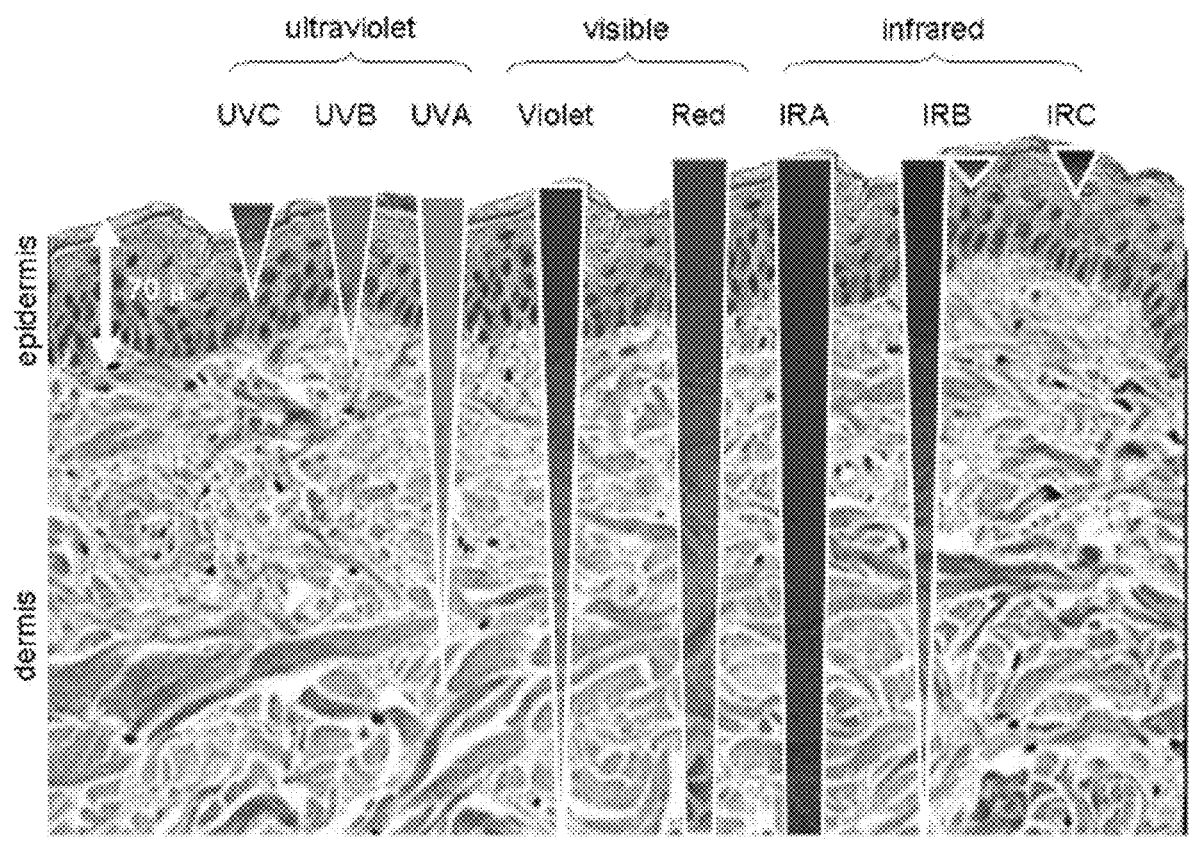

FIG. 24. Depth and Spread of light of various wavelengths in tissue that is the skin and underlying dermis.

FIG. 25. Table showing the average depth of the epidermis and dermis layers in various locations.

Figure 26:
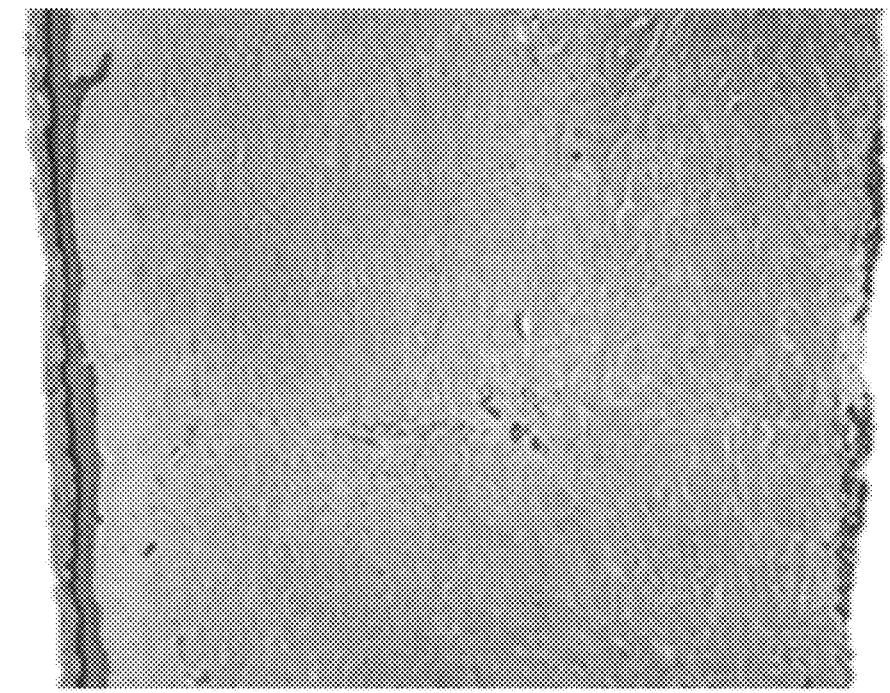

FIG. 26. UVA-1: Morphea penetration depth of 0.5 mm is less than typical lesion depths of about 3 mm.

Figure 27:
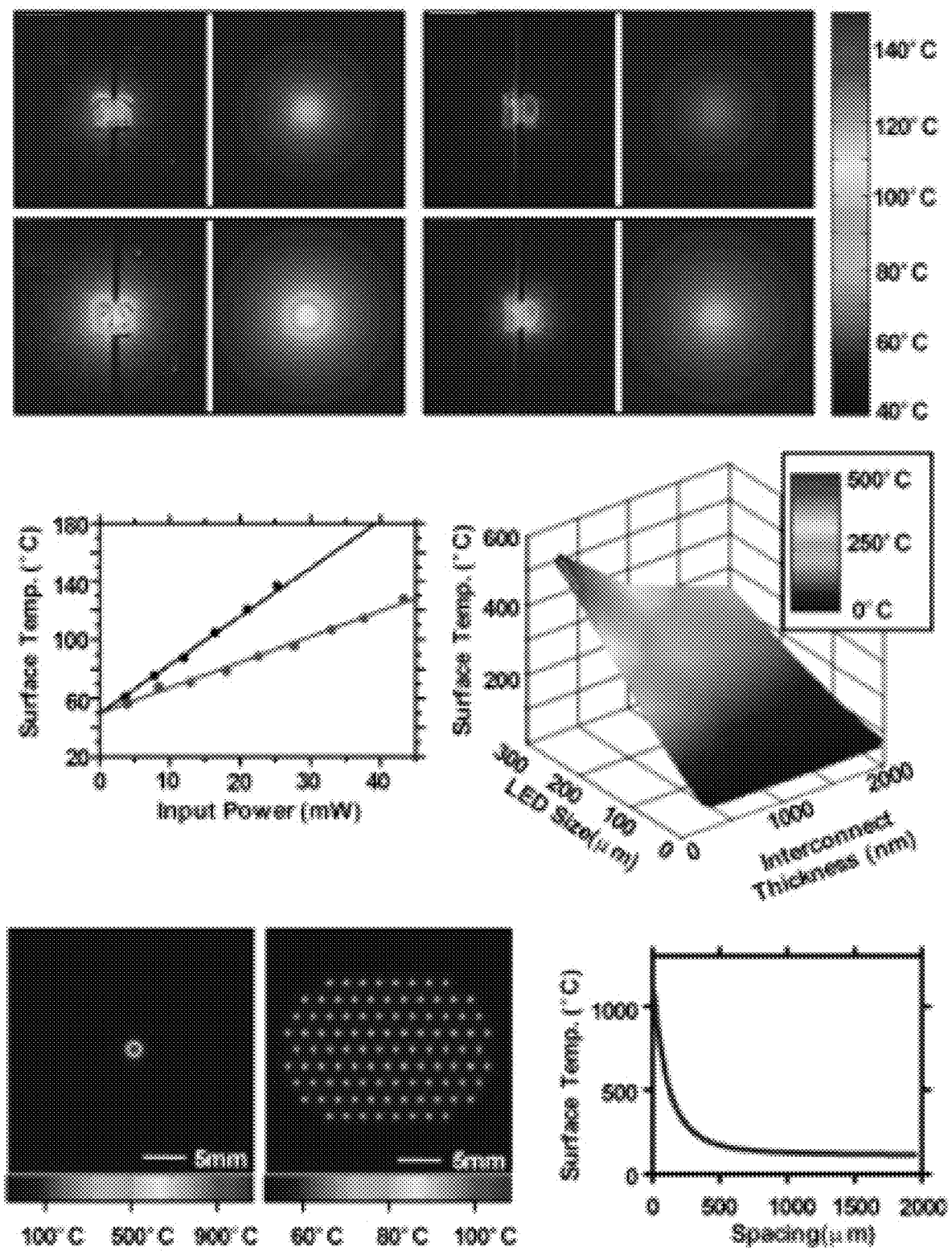

FIG. 27. Unusual strategies for using indium gallium nitride grown on silicon (111) for solid-state lighting.

Figure 28:
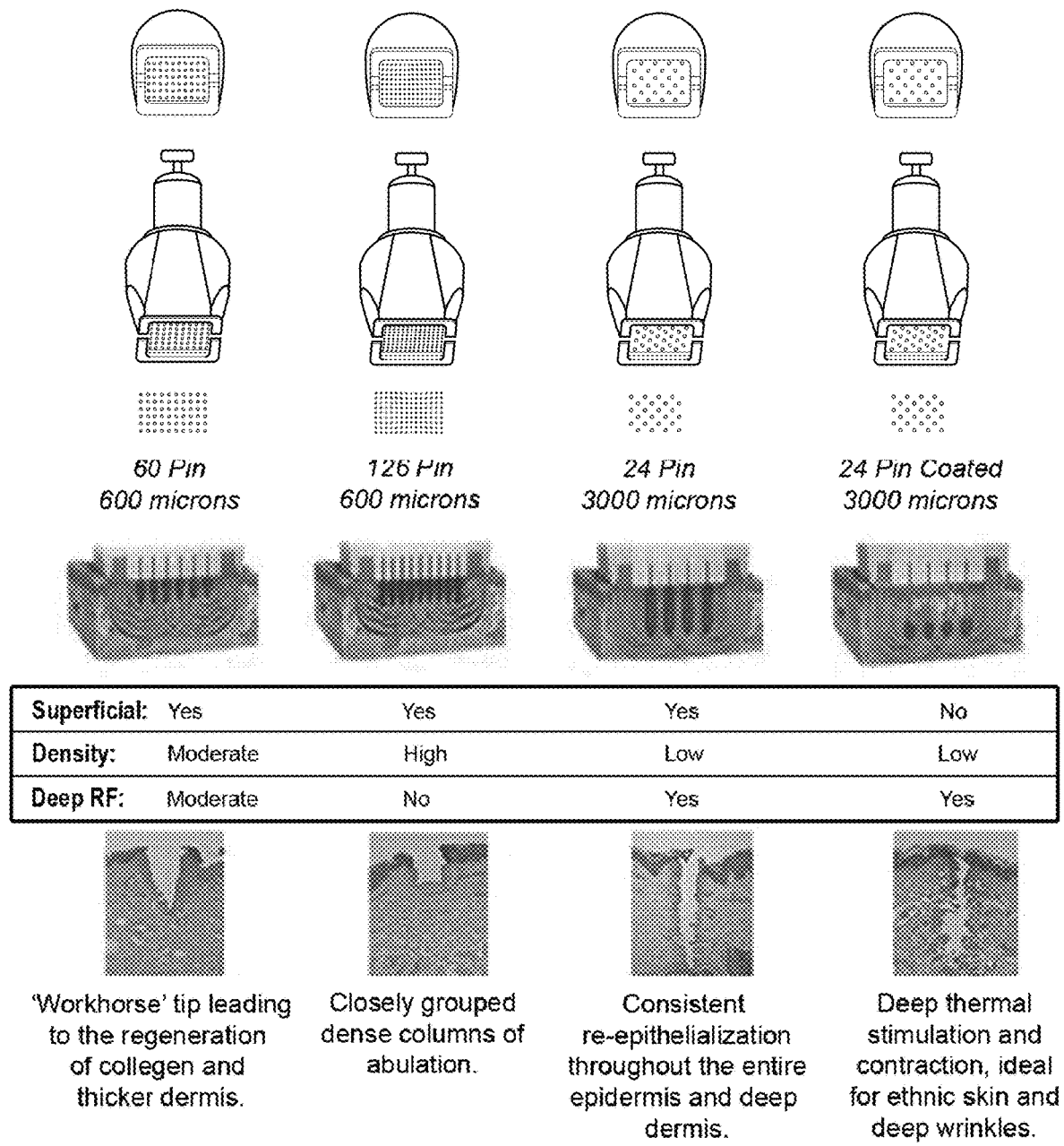

FIG. 28. Selective depth-dependent heating.

Figure 29:
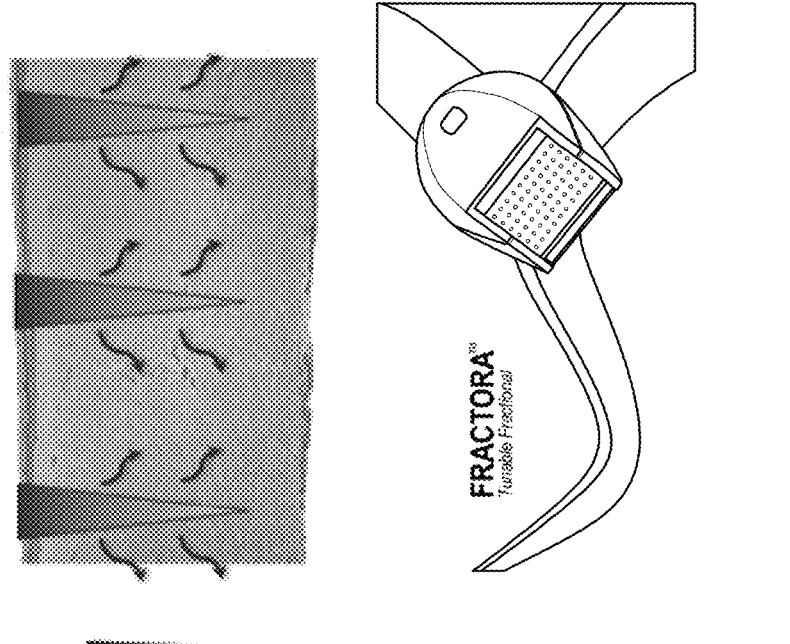
Figure 30A:
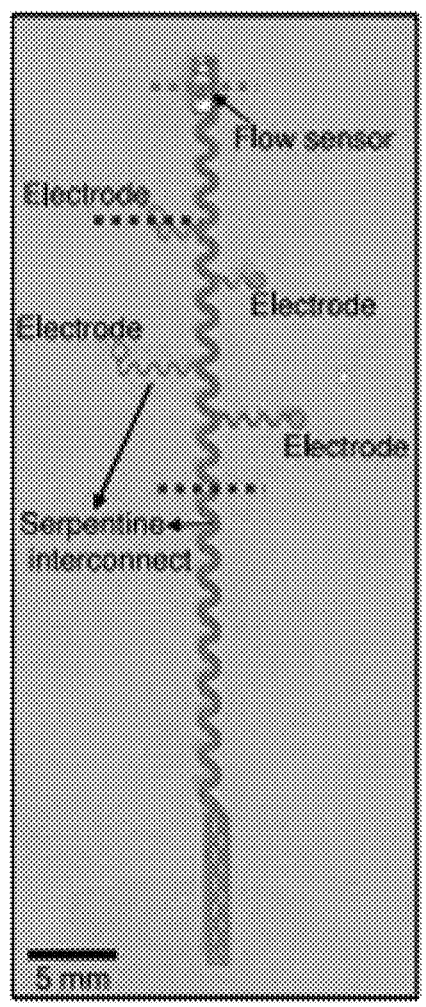
Figure 30B:
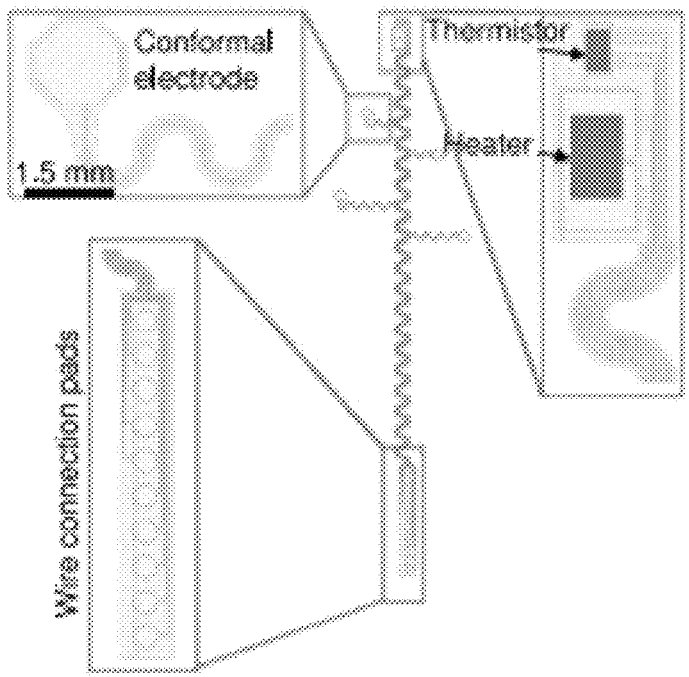
Figure 30C:
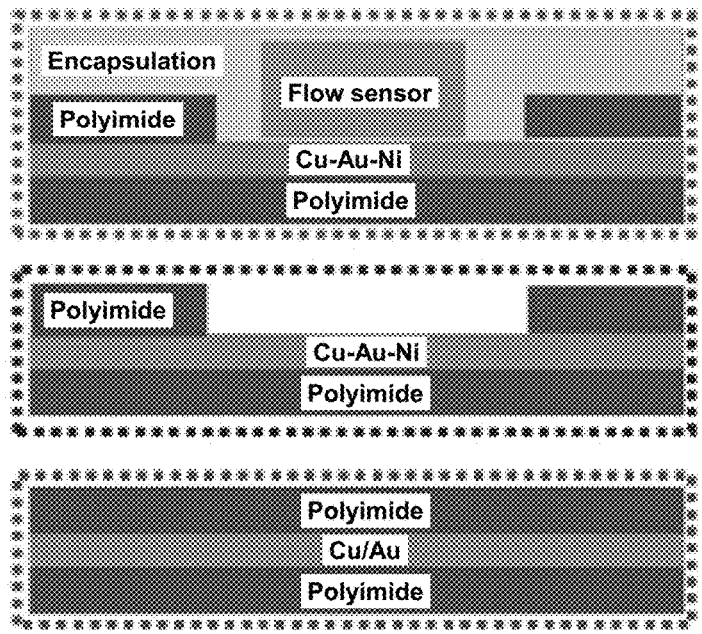
Figure 30E:
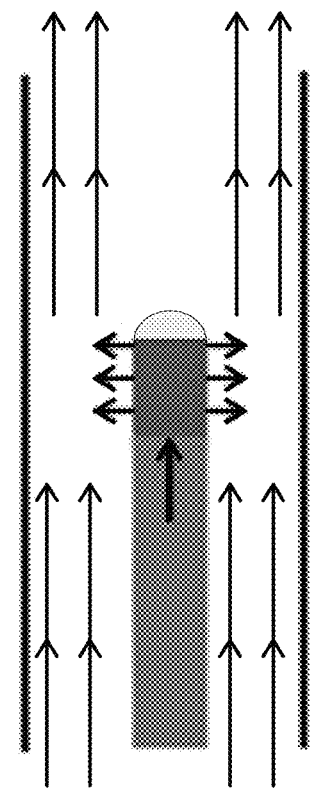
Figure 30D:
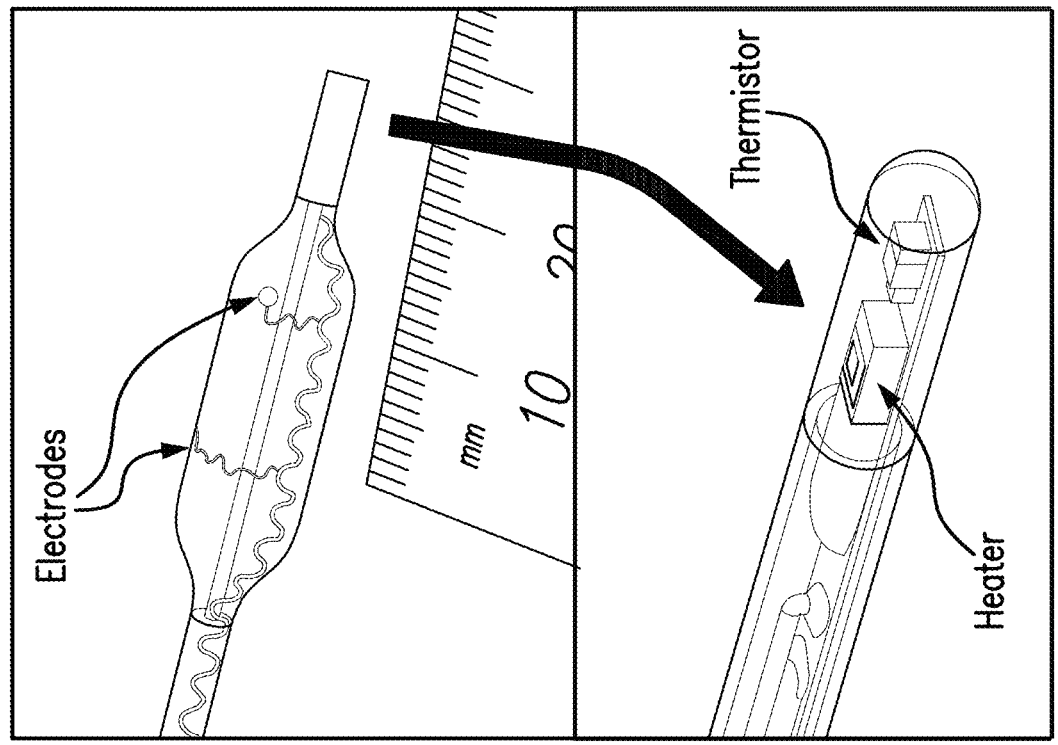

FIG. 29. Microneedle designs.

FIGS. 30A-30E. Interventional Cardiology: UVA.

Figure 31:
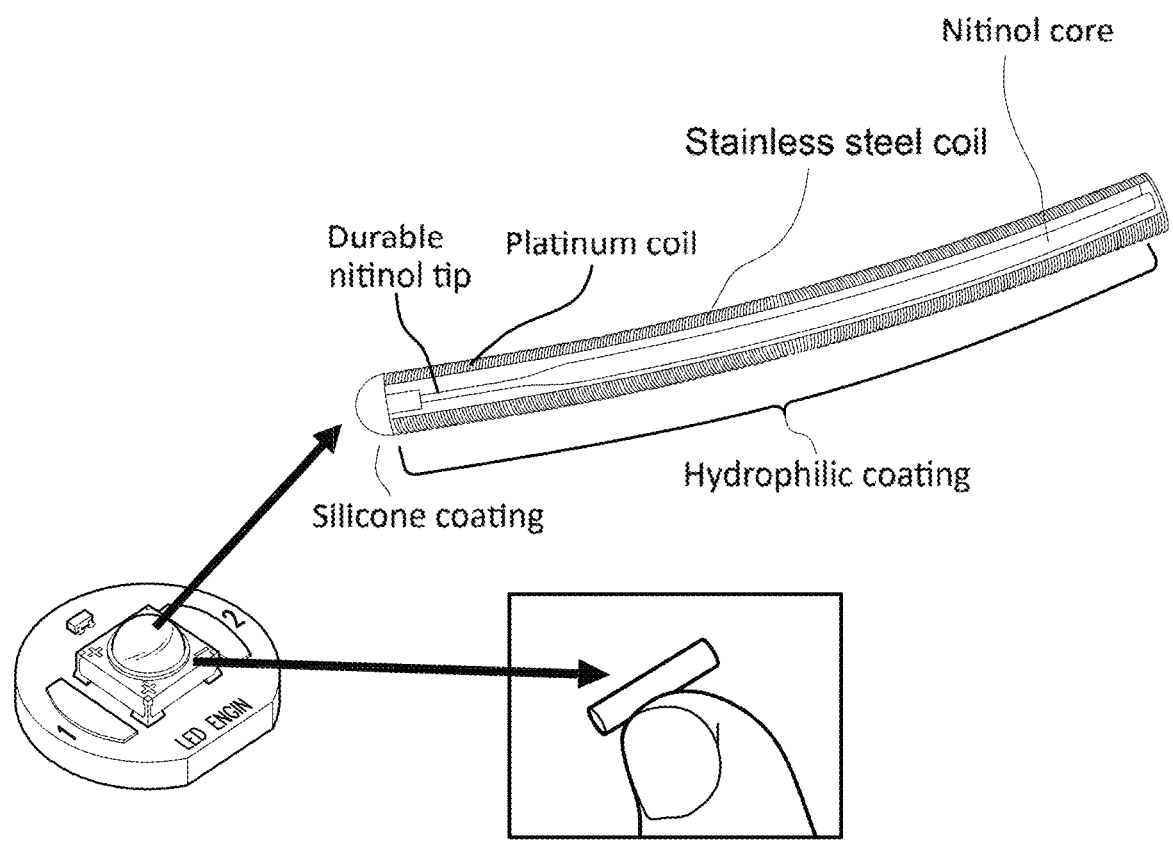

FIG. 31. The Runthrough NS (Terumo Interventional Systems, Somerset, New Jersey).

Figure 32:
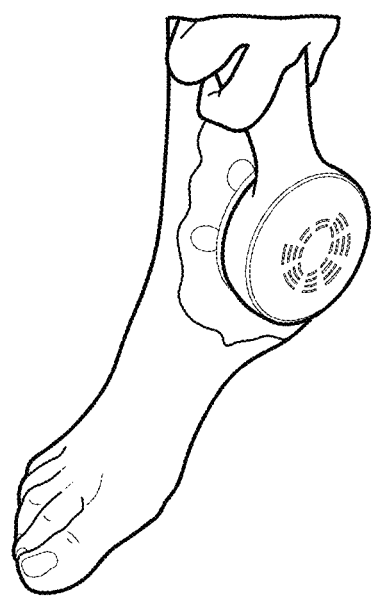
Figure 33A:
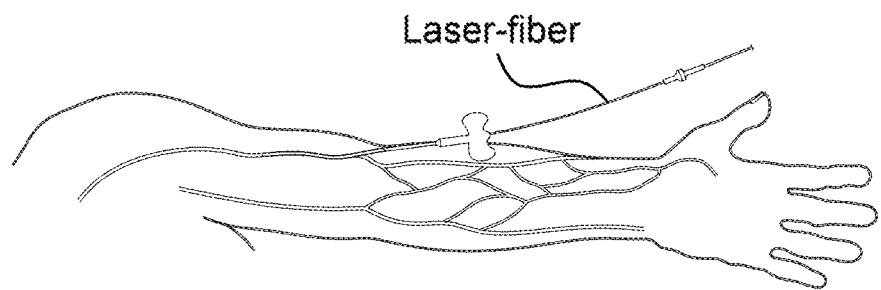
Figure 33B:
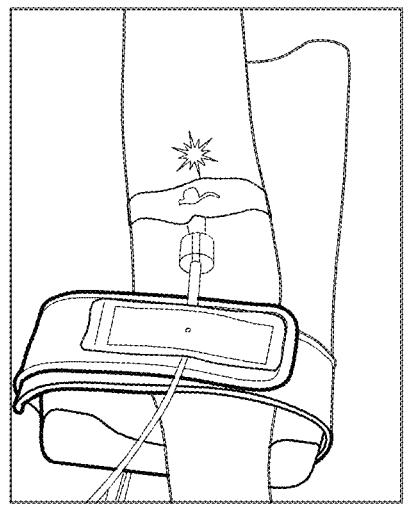
Figure 33C:
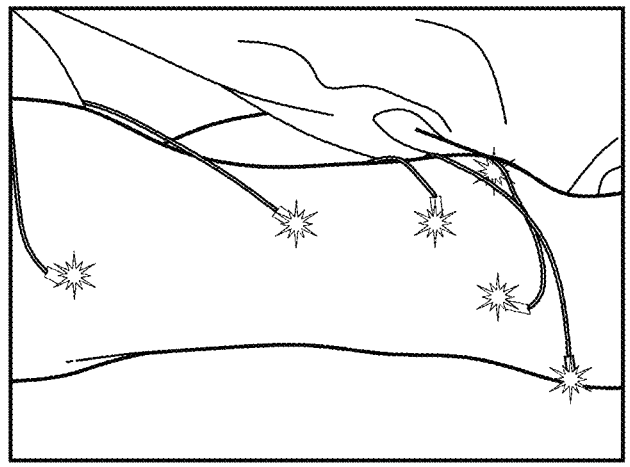
Figure 33D:
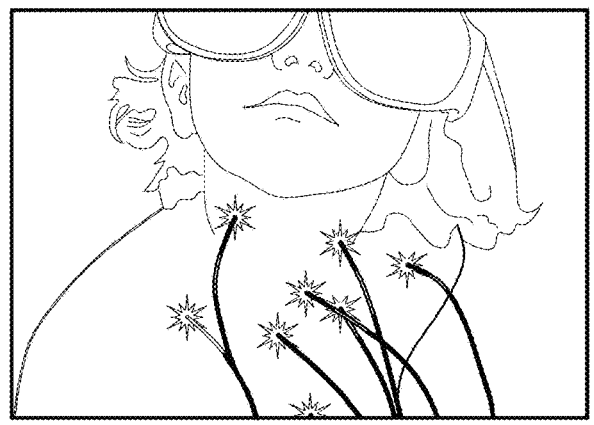
Figure 33E:
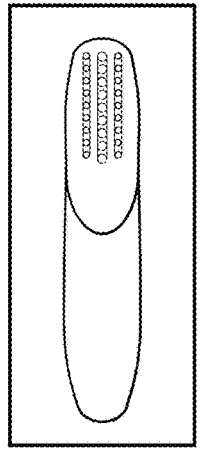
Figure 33F:
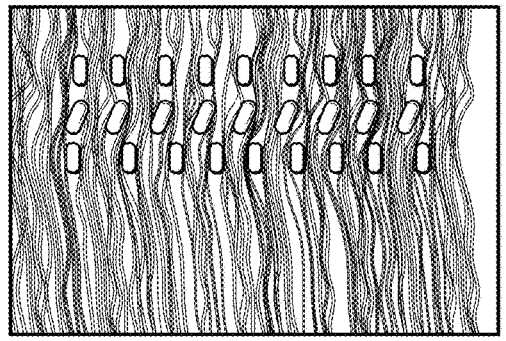
Figure 33G:
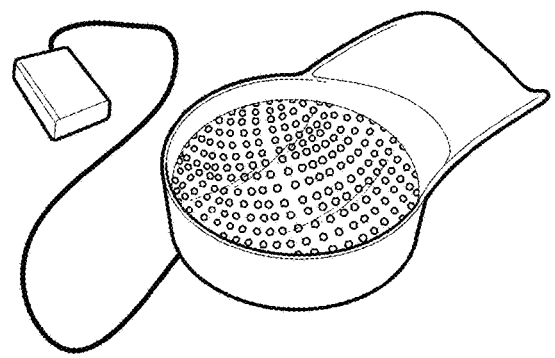

FIG. 32. LLLT+Waveguides+Heat: Pain—demonstration on ankle.

FIGS. 33A-33G. LLLT+Waveguides+Heat: Pain.

Figure 34:
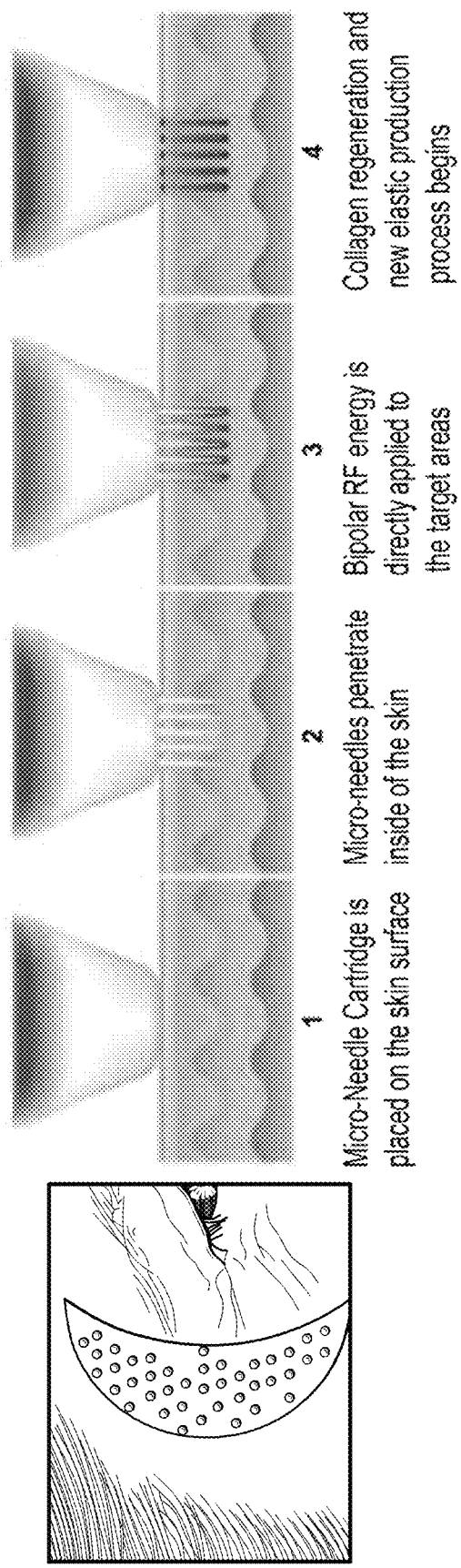

FIG. 34. Low Level Light Therapy: Periorbital Rhytides.

Figure 35:
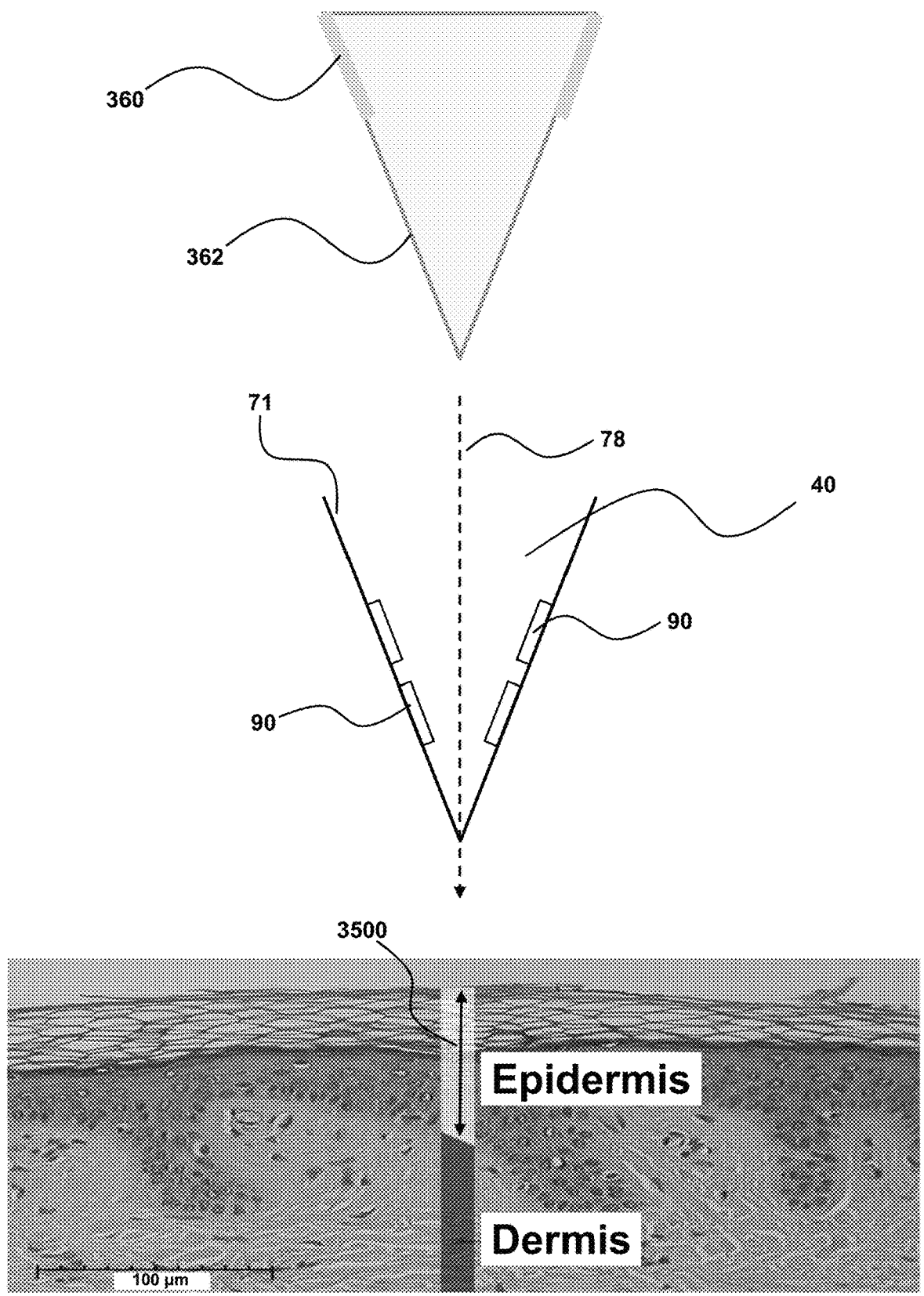

FIG. 35. Use of optical modulator (top panel) to avoid UV exposure to the proximal region of the penetrating member without impacting UV exposure at more distal regions, such as for the epidermis and dermal layers, respectively. Distribution of optical sources over a microneedle surface (middle panel). The bottom panel illustrates sizes of the epidermis and dermis, and the need for the devices and methods of the instant invention with respect to skin and underlying tissue.

Figure 36:
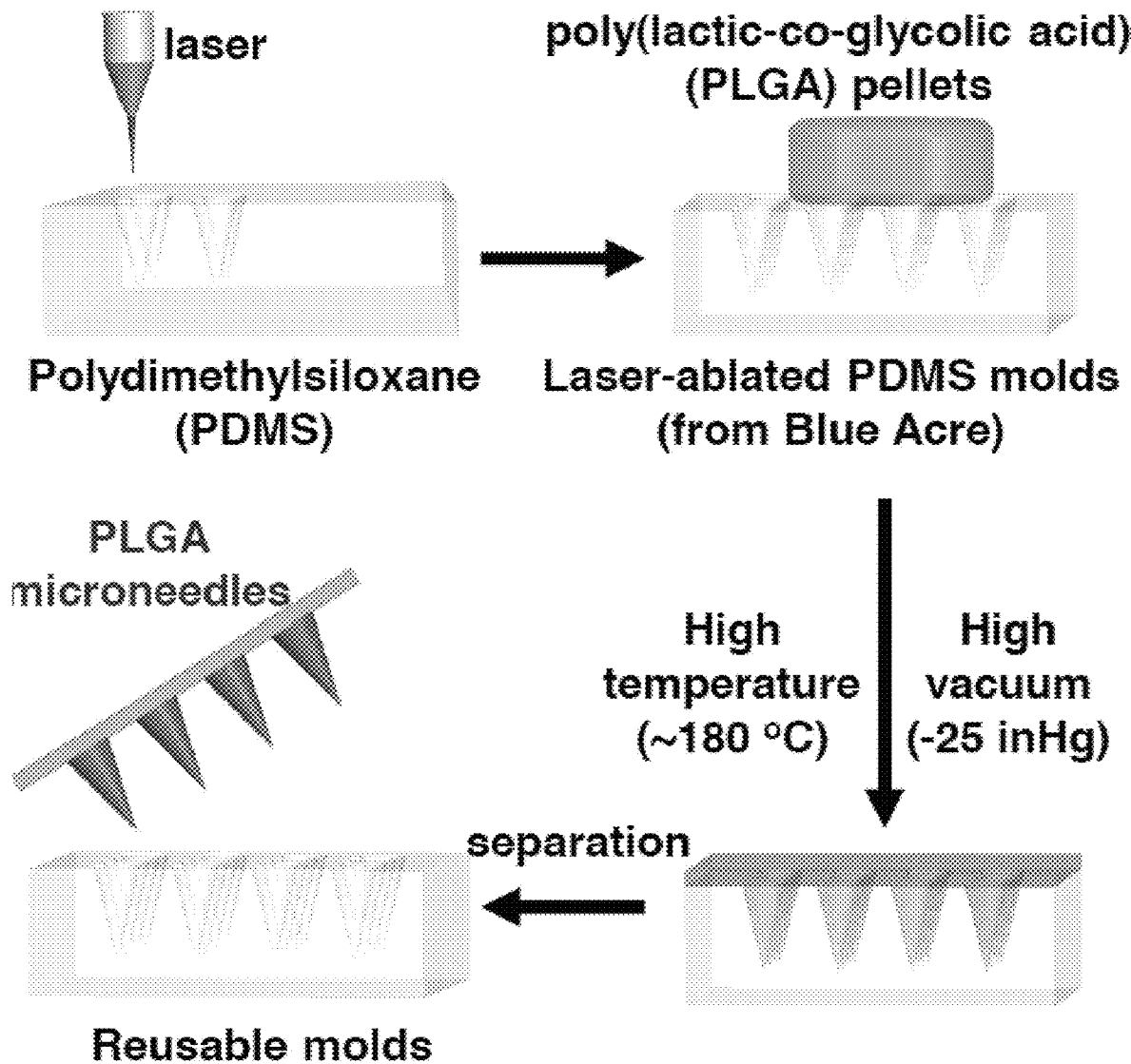

FIG. 36. Fabrication scheme for an array of polymeric microneedles.

Figure 37:
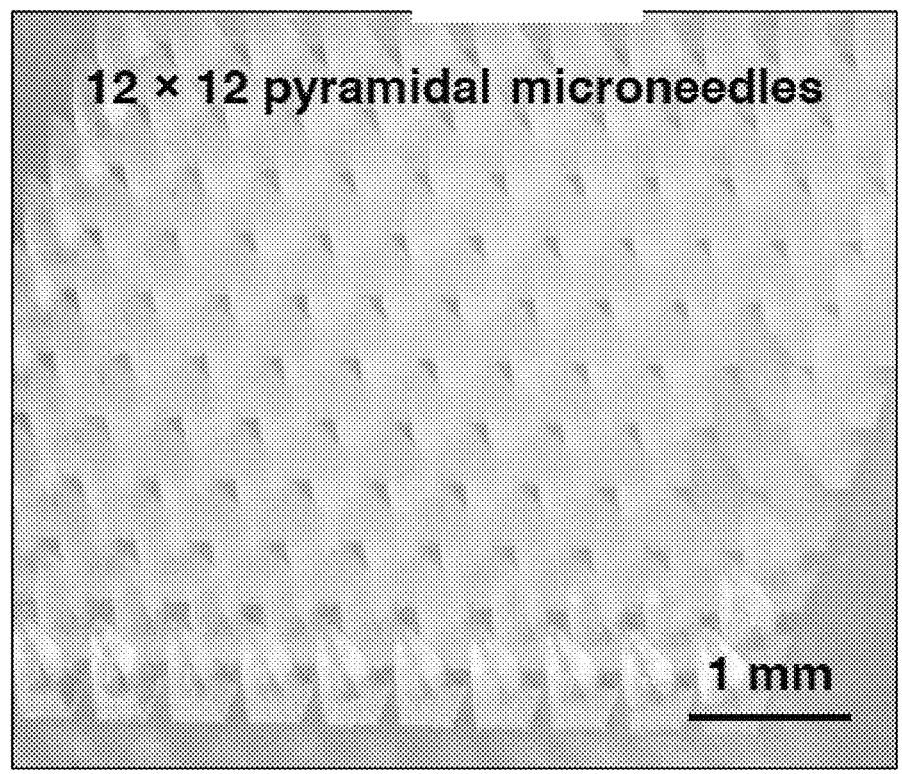

FIG. 37. Image of a 12×12 array of pyramidal microneedles, having a length of 1 mm, size of 400 µm, pitch 600 µm.

Figure 38:
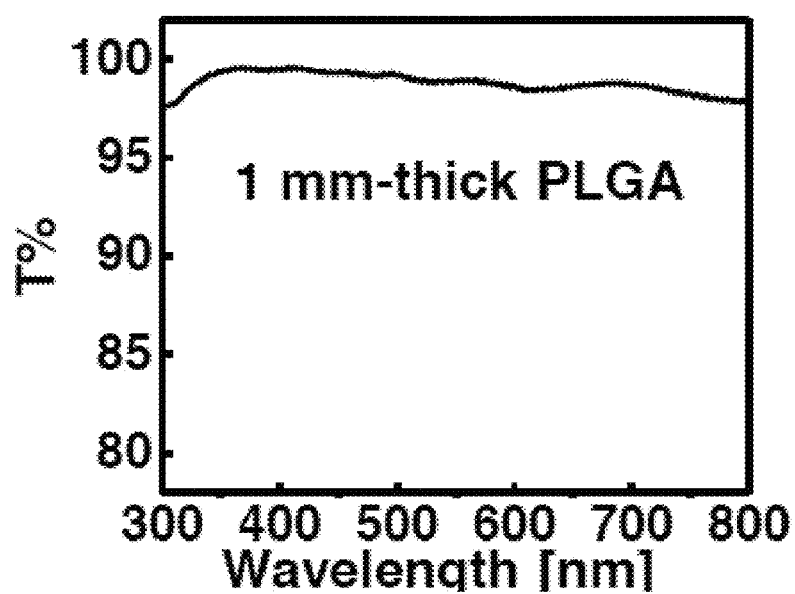

FIG. 38 is a plot of optical transmission as a function of wavelength (nm) for a 1 mm thick PLGA substrate.

Figure 39:
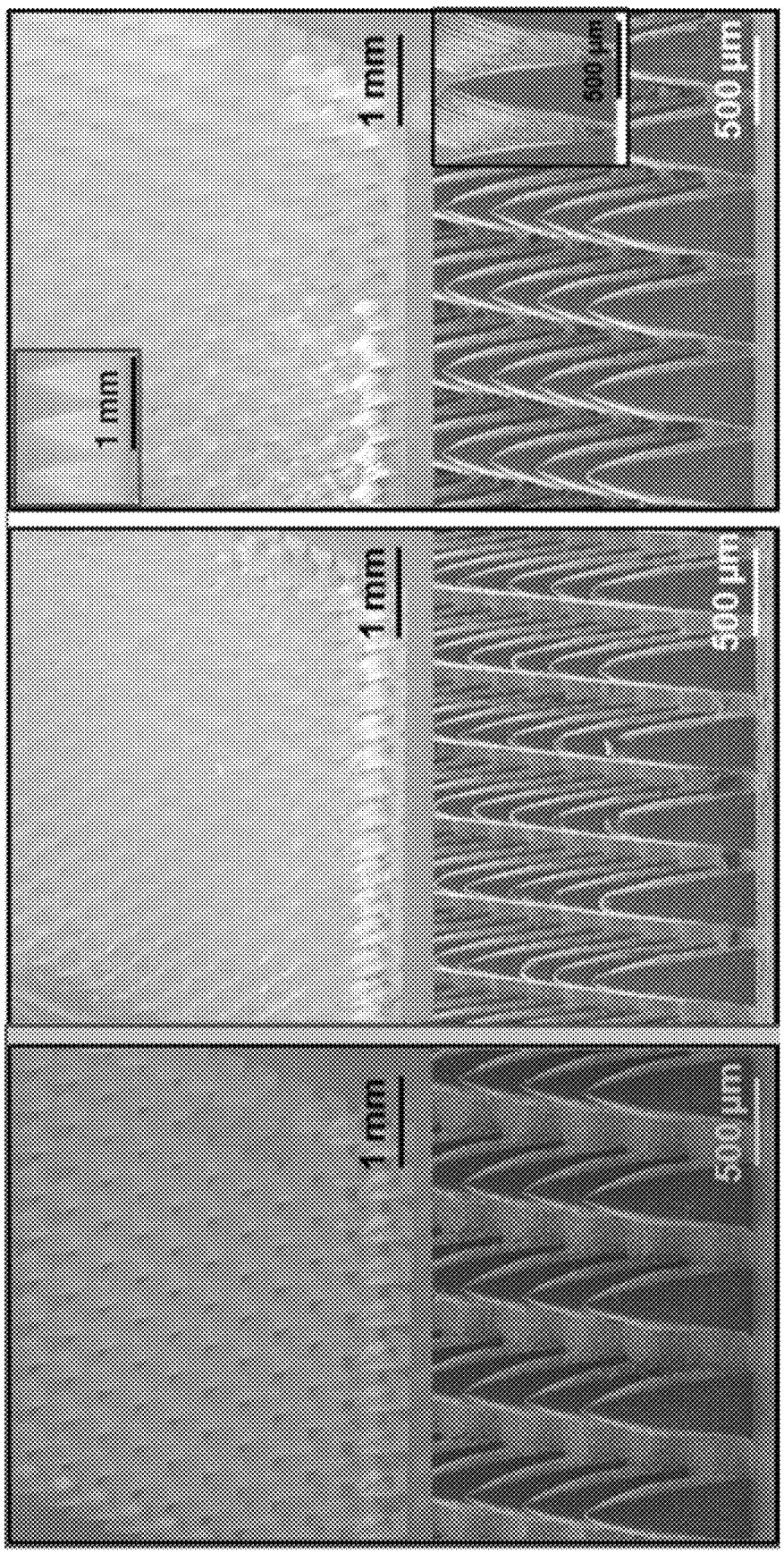

FIG. 39 are images of arrays of microneedles having different geometrical configurations, with microneedle footprint fractions of 44%, 56% and 64%.

Figure 40:
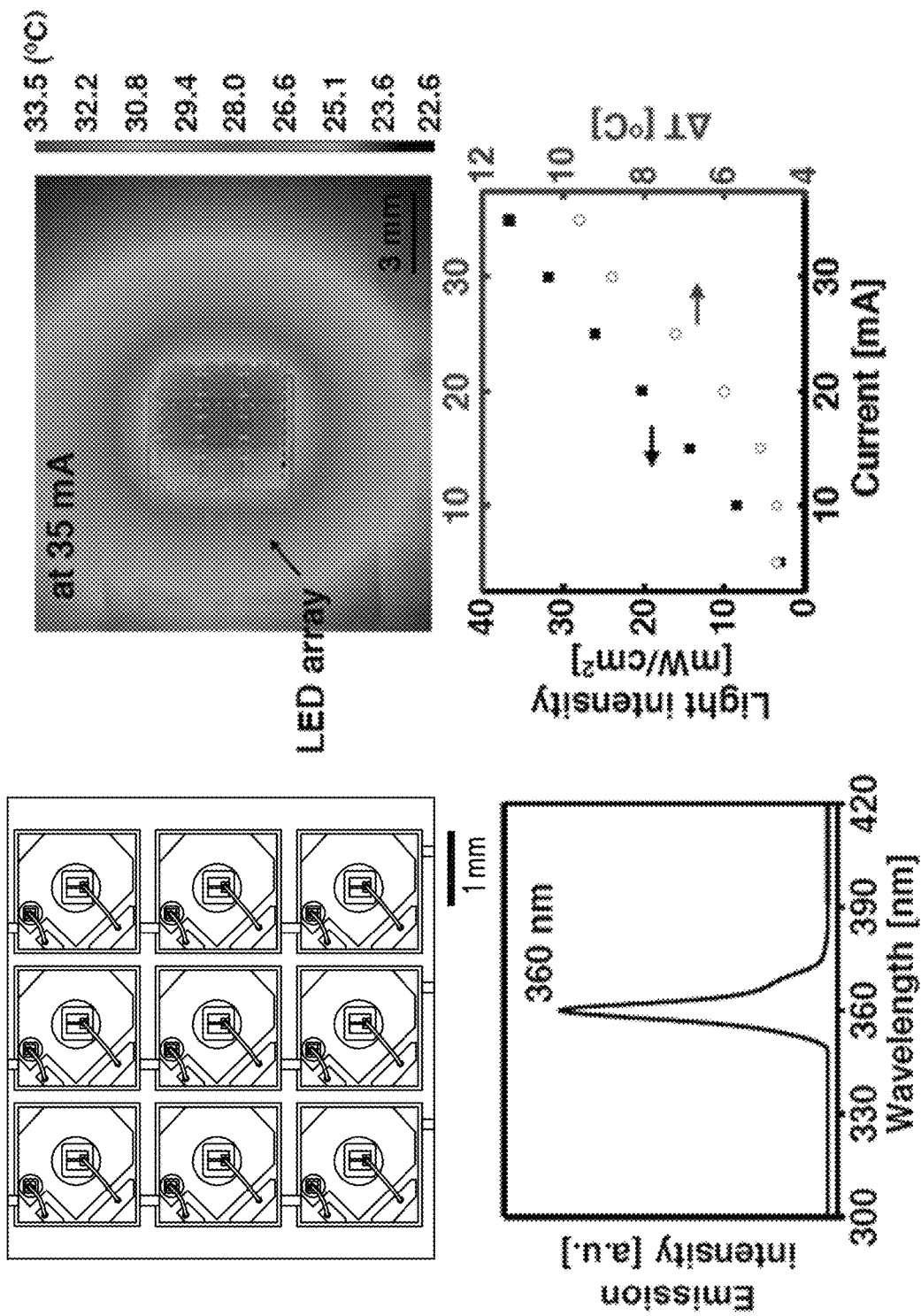

FIG. 40 characterizes a UVA LED patch comprising 3×3 LEDs (1.6×1.6×1.4 mm) (top left panel) having an emission spectrum illustrated in the bottom left panel. The top right panel is a temperature distribution plot. The bottom right panel is a plot of light intensity or temperature change as a function of current.

FIG. 41A is a light intensity map for a device having 3×3 array of LEDs over the footprint (scale bar is 1 mm). FIG. 41B is a plot of light intensity along nine random lines in the patch area. FIG. 41C is a photograph of the device accommodating a bending radius of about 3.5 mm without fracture. FIG. 41D is a plot of current versus voltage for a flat and a bent configuration (lines overlap), indicating bending does not affect electronic characteristics. FIG. 41E is a photograph of the device illustrating conformal characteristics, even to a curvilinear surface.

FIG. 42 illustrates the extreme flexibility of the device, with low strains even in the curved conformation.

Figure 43A:
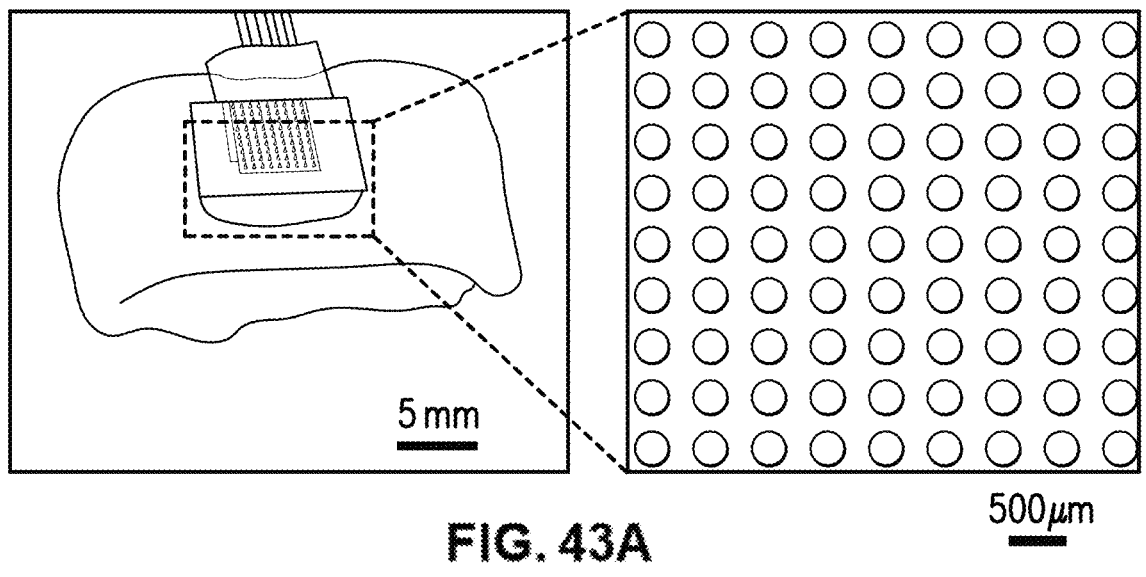
Figure 43B:
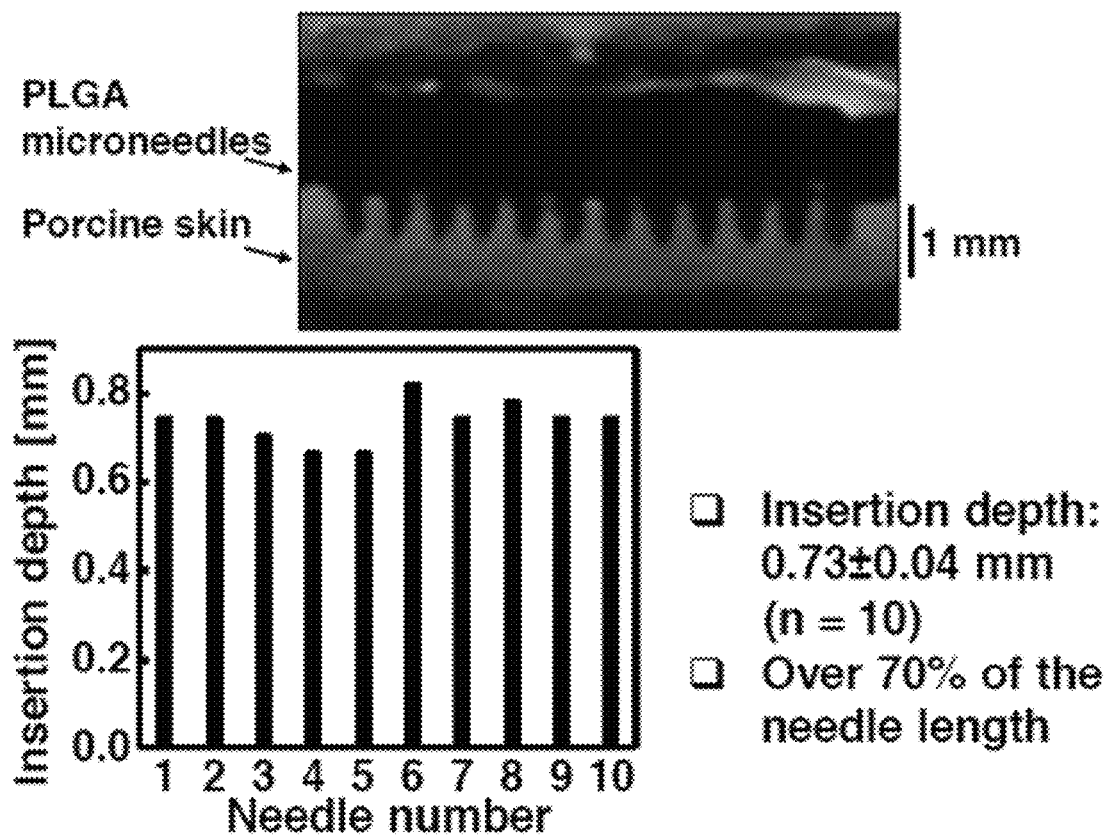

FIG. 43A is a photograph of the device on tissue (left panel—scale bar 5 mm) with a close up view of the needle array (right panel—scale bar 500 µm). FIG. 43B illustrates microneedle penetration in porcine skin (top panel) and the measured insertion depth for various microneedles within the array (bottom panel).

Figure 44:
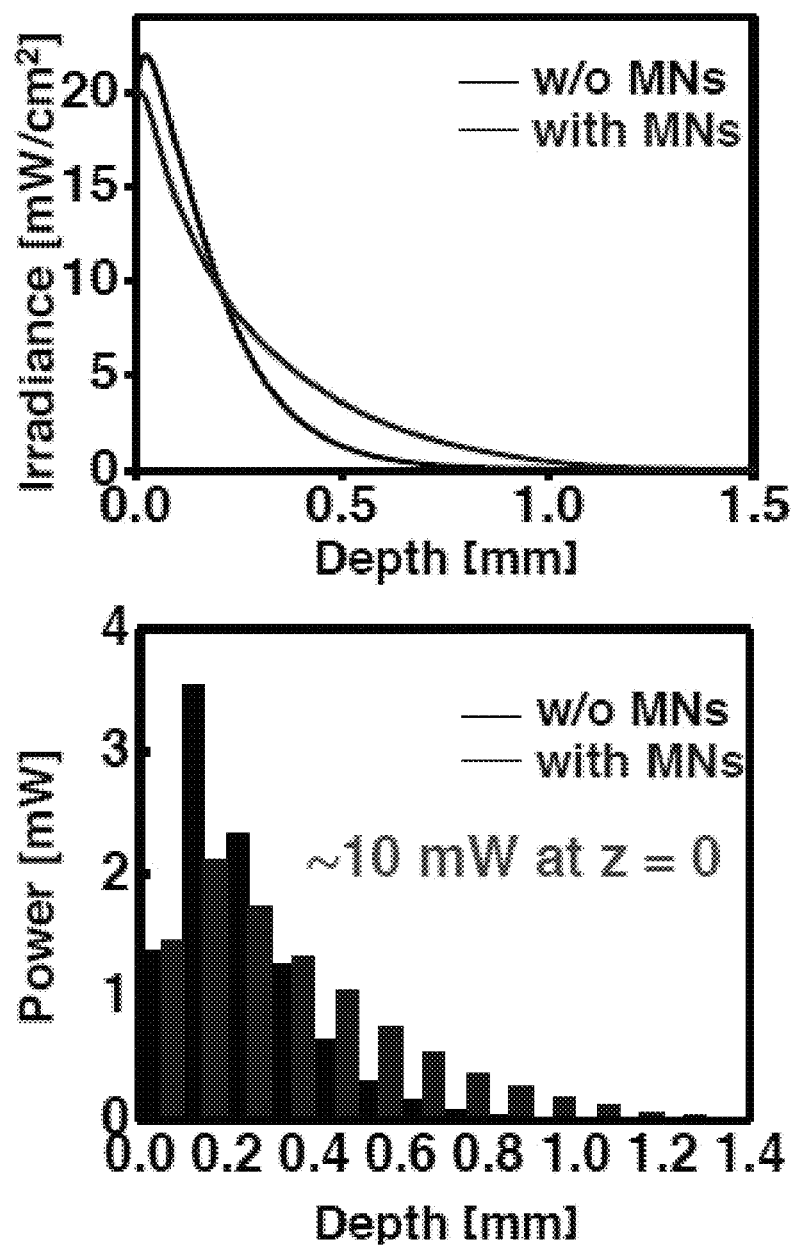

FIG. 44 Monte Carlo simulations of illumination with and without microneedles (irradiation area 400 µm×400 µm; needle length 1 mm (single microneedle) and length/size/pitch of 1000/400/600 µm for a microneedle array. The top panel is a plot of irradiance as a function of tissue depth and the bottom panel a plot of power as a function of depth, without and with microneedles (MN).

Figure 45B:
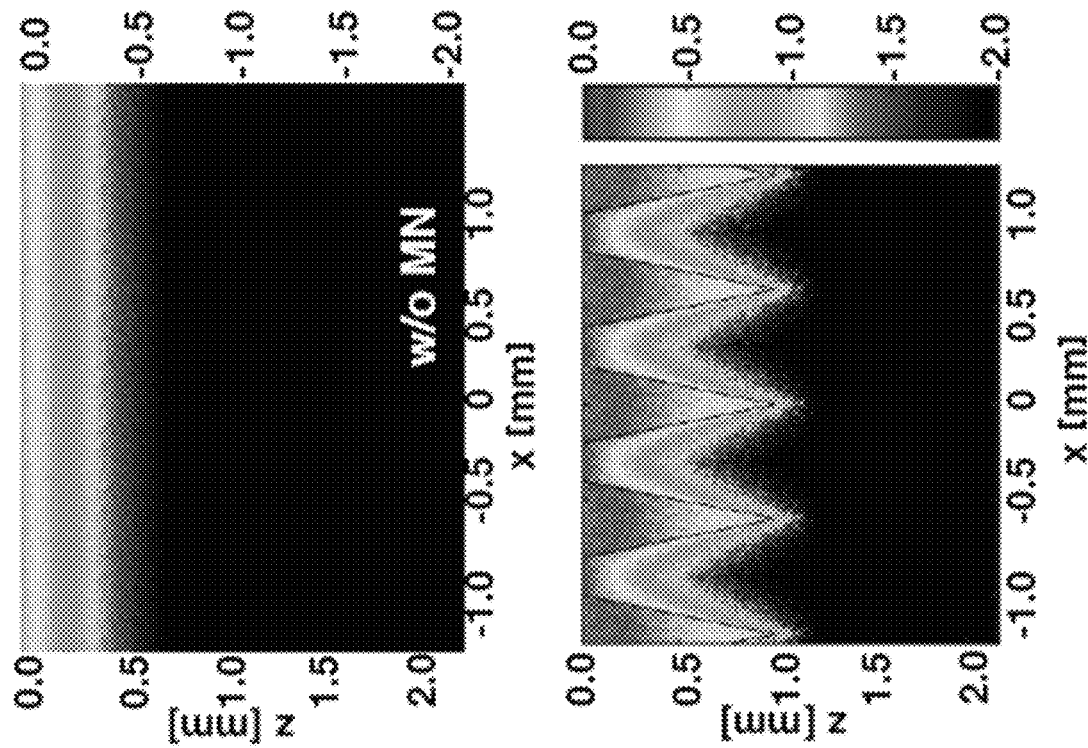
Figure 45A:
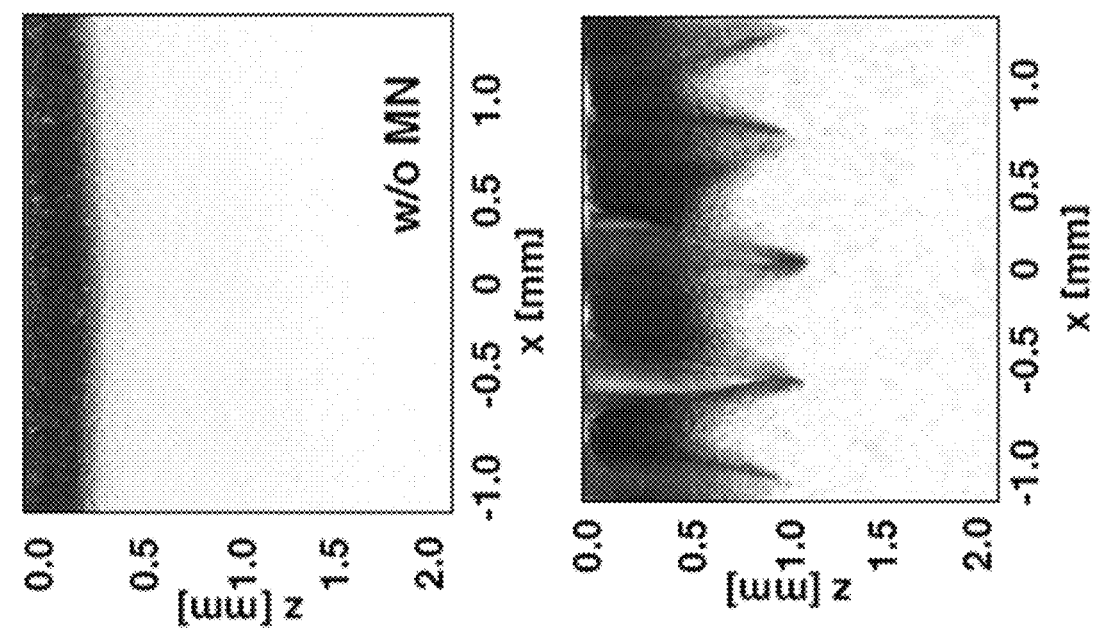

FIG. 45A is an experimental result of UV dye activation using UV light in a gel skin phantom without (top panel) and with (bottom panel) a microneedle array. FIG. 45B is an equivalent result with Monte Carlo simulations, thereby validating the computational model without (top panel) and with (bottom panel) microneedle array.

FIG. 46A is a top view of a device laminated on ex-plant human skin tissues. FIG. 46B is a side view of FIG. 46A. FIG. 46C-46D is a plot of percentage of cells positively identified as damaged as a function of power (13.5 J/cm$^2$ and 37.5 J/Cm$^2$, respectively) for a conventional device (Lamp) and the instant microneedles (MN).

DETAILED DESCRIPTION OF THE INVENTION

In general, the terms and phrases used herein have their art-recognized meaning, which can be found by reference to standard texts, journal references and contexts known to those skilled in the art. The following definitions are provided to clarify their specific use in the context of the invention.

"Conformable" refers to the ability of a device to undergo macroscopic deformation so as to maintain intimate contact with a curvilinear surface without generating substantial deformation forces on the underlying surface. Such conformal contact is particularly challenging in the context of soft biological tissue that is readily deformed, even under relatively mild forces, including the skin. Such unwanted deformation-generating forces can cause discomfort and irritation to the underlying tissue. Such problems are avoided in the instant technology by specially constructing the penetrating members, optical sources, and supporting substrate, so that the device as a whole is flexible and able to accommodate a wide range of complex shapes, thereby ensuring conformal contact is maintained. Such conformal contact may be further quantified in terms of no significant separation distance between the device and underlying surface. This helps ensure maximum light delivery to the desired location, and avoids unwanted light leakage. Conformability may also be described in terms of the device being "flexible" and having a suitable bending modulus to provide desired curvature under an applied force. Conformable may be further described in terms of desired mechanical properties such as bending stiffness and Young's modulus such that air gaps are not present, thereby maximizing light transfer to underlying tissue.

"Microarray" refers to a plurality of members, with each member having at least one dimension that is less than 1 mm.

"Penetrating member" refers to a waveguide capable of being inserted into tissue. As the devices presented herein are compatible with a range of tissues, the term "dermal penetrating member" can be anywhere replaced with the term "tissue penetrating member" (or vice versa), a reflection that the penetrating members need not be limited to penetrating a dermal layer.

"Penetrating depth" refers to the distance beneath a surface that light can effectively travel.

"Optically transparent" refers to a material where light can pass. Depending on the application of interest, the light may be UV light, such as UVA or UVB light, or visible light, such as blue, red, green or any other color as desired. For example, in PDT applications, the desired wavelength may correspond to the excitation wavelength of an optically active agent.

"Encapsulation layer" refers to a material that at least partially covers another component, thereby protecting it and/or providing a desired mechanical parameter, such as bending stiffness, flexibility or softness.

"Substantially uniform" refers to, in the context of light intensity, no significant hot spots of light intensity. The may be quantified, as a maximum light intensity that is less than 20% different from the average light intensity over the entire device illumination footprint.

Figure 10:
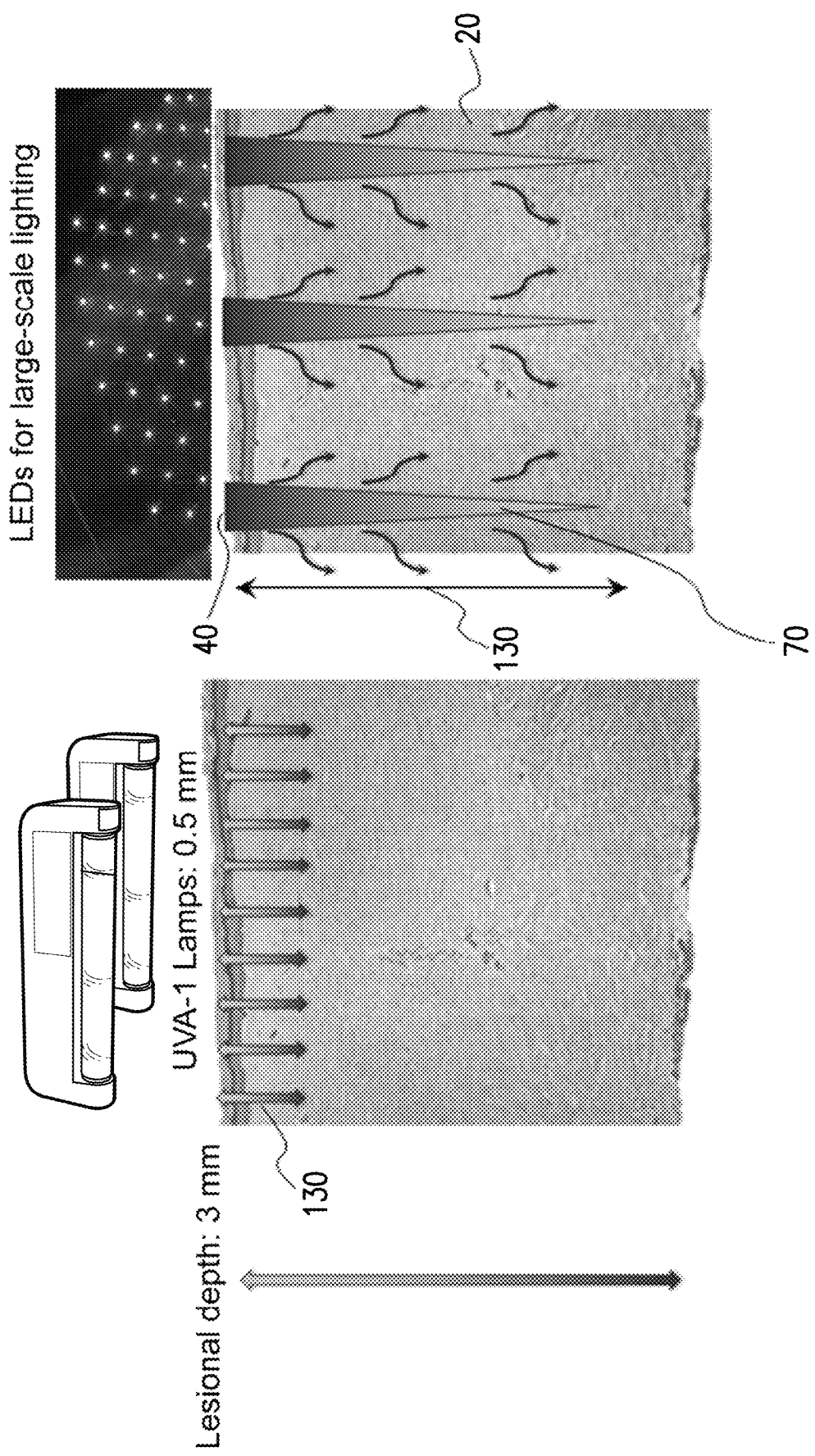
FIG. 10. Illustration of traditional UV phototherapy limited by penetration depth compared to a device provided herein having tissue penetrating members. The top layer of the LEDs of the device delivers uniform UV light but with the added advantage of microneedle waveguides enabling deeper penetration of light when desired, as reflected by increased penetration depth 130 between left and right panels. Arrays of light sources, such as LEDs, facilitates controlled light exposure surface area and also can provide very large surface area exposure, with controlled activation of the light sources also providing the ability to reliably illuminate relatively small surface areas.

Referring to the figures, FIG. 1A illustrates a conformable light delivery device 10 that can increase light penetration depth 130 in a tissue 20 (see, e.g., FIG. 10, left panel without the instant device having less penetration depth 130 compared to right panel where the penetrating members significantly increase penetration depth 130). A microarray 30 of tissue penetrating members 40 that are at least partially optical transparent facilitate increased penetration depth of light into tissue. Each penetrating member has a proximal end 60 and a distal end 50, where the distal end is directed toward deeper in the tissue and the proximal end extends from or is connected to a substrate 80 that supports the microarray 30 of penetrating members 40. Between the proximal and distal ends, a surface 70 can be configured to continuously transmit length over the longitudinal length or to modulate and control light delivery as a function of position along the longitudinal length, such as increased light intensity introduced to surrounding tissue toward the distal end compared to the proximal end.

Figure 15:
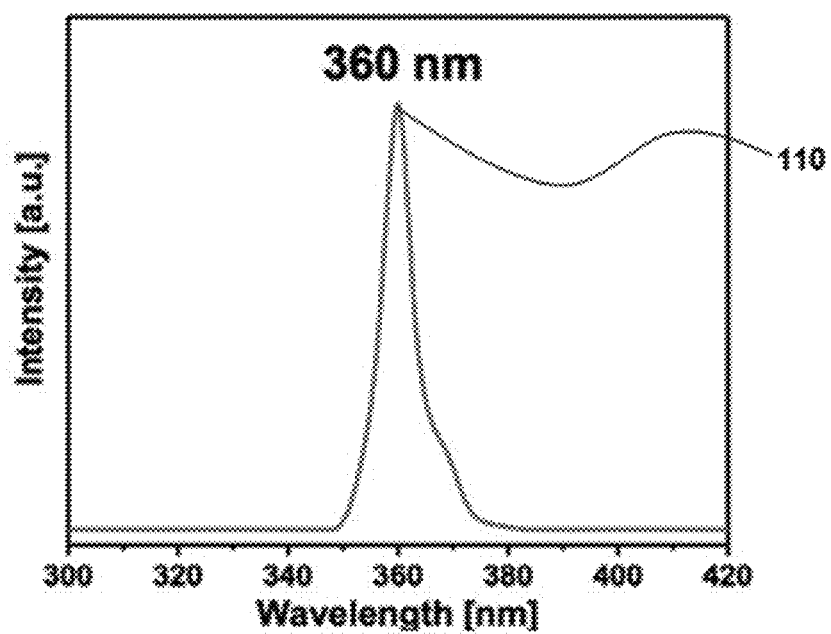
FIG. 15. Spectral results based on bench testing of Vishay UVA1 LEDs indicate the desired peak output of 360 nm.
Figure 17:
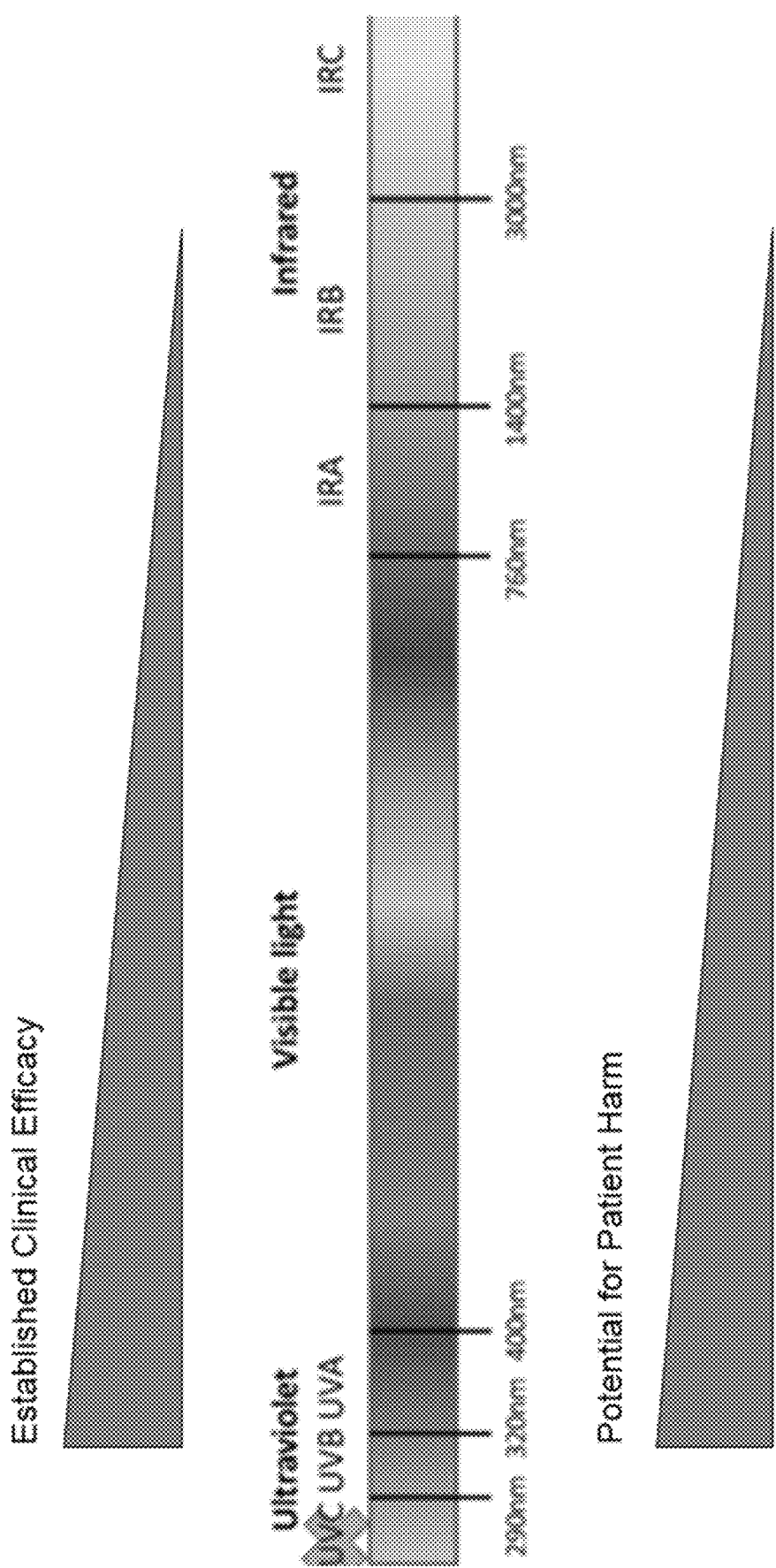
FIG. 17. Phototherapy: Wide Spectrum of Biological Activity over various wavelengths, with associated potential harm.
Figure 18:
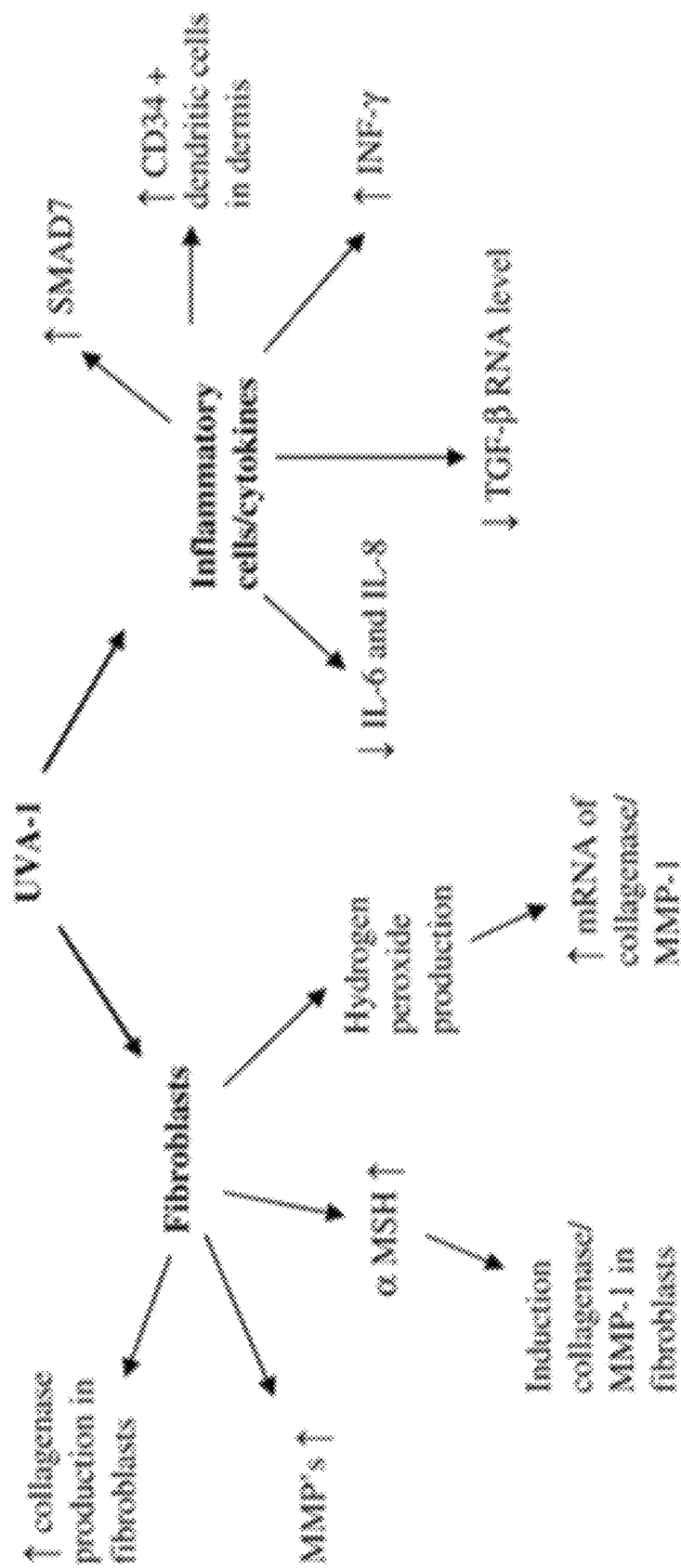
FIG. 18. Schematic reproduction of biological effects of ultraviolet A (UVA)-1 on sclerotic skin diseases. IL, Interleukin; INF, interferon; MMP, matrix metalloproteinase.

An optical source 90 generates electromagnetic radiation over a desired wavelength (FIGS. 17-19), including at an emission maximum 110 (see, e.g., FIG. 15). The optical light source 90 may comprise a plurality of LEDs 100, including UVA and/or UVB LEDs, depending on the application of interest. The microarray of members 40 maybe integrated with the optical light source 90 and corresponding electronic circuit 430. Alternatively, the portion of the device that comes into contact with biological material (e.g., members 40 and substrate 80) may be removably connected to other portions of the device (e.g., light source 90 and electronics 430), for reuse of the optical portion, and disposal of the member/substrate portion. The connection may be via a removable adhesive, geometrical mating contact, and/or mechanical connector.

One or more encapsulation layers 120 may be used to protect underlying components, increase mechanical robustness and/or facilitate conformability with underlying tissue.

Figure 1D:
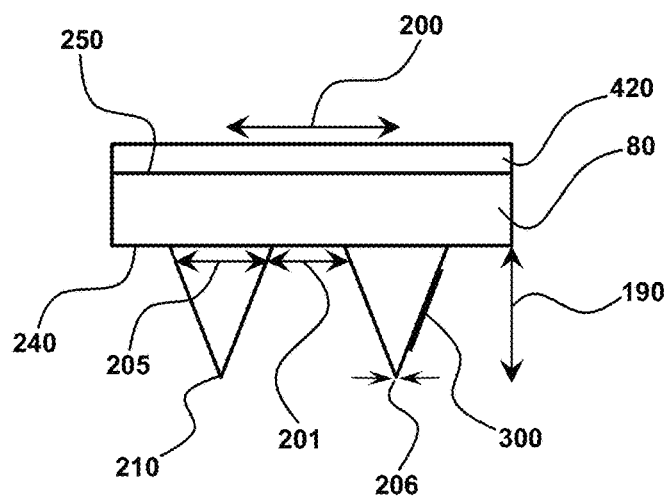

FIG. 1D is a cross-section of the device portion corresponding to the substrate 80 and penetrating members. The substrate 80 has a bottom surface 240 that supports the penetrating members and an opposed top surface 250 that faces toward optical source, such as the optical source 90 illustrated in FIG. 1A. Members 40 may be defined in terms of a length 190, a pitch 200 (between center points of adjacent members) 201 (between edges of adjacent members), a maximum width 205, a minimum width 206 or tip 210. The devices and related methods are compatible with application of a bioactive agent 300, illustrated in FIG. 1D as a coating on at least a portion on the surface of the penetrating member. The bioactive agent is accordingly in intimate contact with tissue adjacent the members, and can be a reliable means of introducing bioactive agent to tissue. The bioactive agent is optionally photoactive, so that light from the optical light source can be used to activate the agent into an active agent. One example is a photodynamic therapy application, where an agent in combination with light having an actuating wavelength results in, for example, thermal generation, free radical generation, isomerization, or release of an agent that can have an impact on a biological cell, bacteria or virus. The coating may coat the entire outer surface 70 of the members, and may also be coated on the substrate bottom surface. A substrate component 420 may be used to improve light delivery. The substrate component is illustrated as supported by the top surface 250 of substrate 80, but may also be positioned on the bottom surface 240, within the substrate 80 and/or in or on the member surface 70. For configurations where member is hollow, a component may be supported on an inner-facing and/or outer-facing wall of surface 70.

Figure 1E:
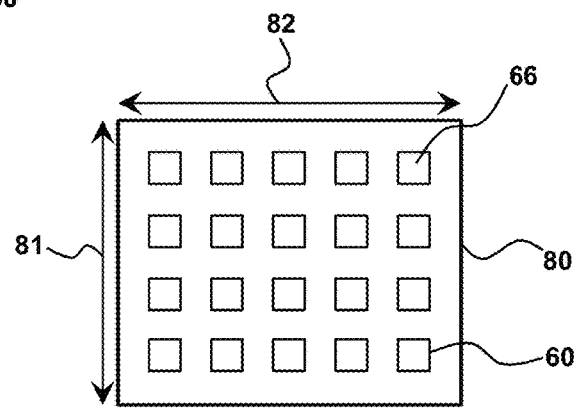
Figure 1F:
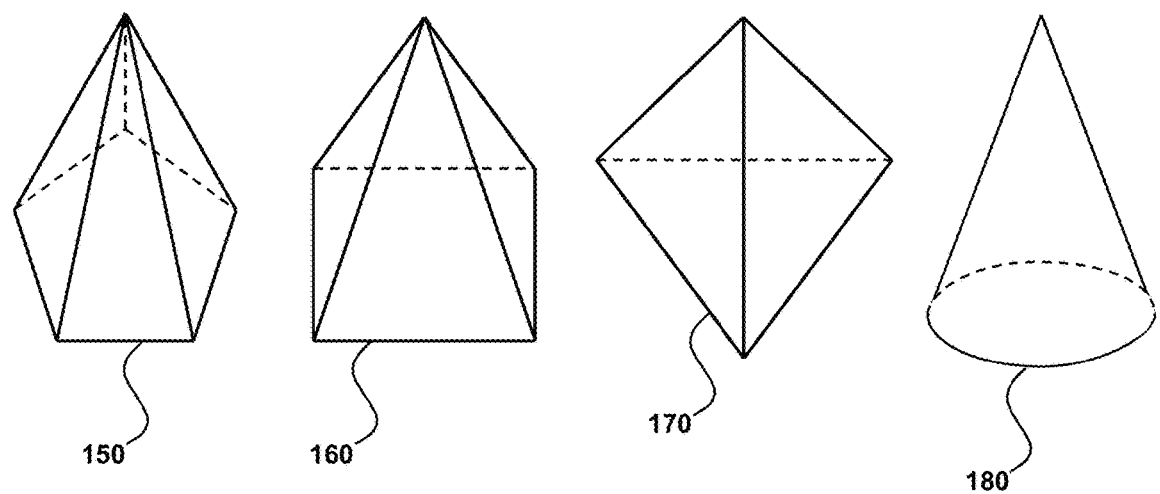

FIG. 1E is a schematic of a bottom view cross-section at the bottom surface 240 of substrate 80. The proximal portion 60 of member 40 may be described in terms of a member surface area 66. The substrate 80 may also be described in terms of a surface area, with, for convenience, FIG. 1F illustrated as rectangular with width 81 and length 82. Of course, the invention is compatible with any of a wide range of cross-sectional shapes of substrate 80 and members 40, with FIG. 1F illustrating tetrahedral 150, square 160, pyramidal 170 and conical 180 needles. The geometry may be described in terms of a "tissue penetrating member occupancy fraction"=n*(proximal member surface area)/(surface area of substrate bottom surface), where n is the number of penetrating members in the array of microneedles, such as ranging from a relatively sparse array (e.g., about 0.05 to 0.2) to a relatively dense array (e.g., from about 0.5 to 0.9), and any subranges thereof.

FIG. 23 illustrates an optical dispersion element 220 configured for optical communication with the tissue penetrating members (e.g., "needles") and optical light source (e.g., LEDs). The optical dispersion elements may be lenses positioned in optical alignment with underlying members 40 to maximize light delivery to the members 40 and minimize light that is directed to areas of substrate not having a corresponding underlying member 40. Although FIG. 23 illustrates optical dispersion element 220 as lenses, other types of dispersion elements are compatible, including roughening (e.g., recess and/or relief features) of members and/or substrate, coatings, diffraction grating, waveguides, patterned optically opaque layer, phosphors. The optical dispersion elements can be positioned in the device (in an optical sense) between the tissue and the light source, between the tissue and the members and/or between the light source and the members.

FIG. 35 (top panel) illustrates a light intensity modulator 360 (e.g., U.V. blocking coating) 362 (e.g., UV transparent coating). In this manner, light intensity may be controlled as a function of distance from the bottom surface of the substrate. This can be useful, for example, where UV light is not desired at a skin surface, but is desired deeper in the tissue.

FIG. 35 (middle panel) illustrates a plurality of light or optical sources 90 optically dispersed along the member wall an inner-facing member wall surface 71. In this manner, further control of light intensity as a function of position along a longitudinal axis 78, e.g., tissue depth, is provided, such as so that only a distal portion, e.g., a buried tissue layer physically separated by distance 3500 from the tissue surface, is exposed to light from the optical light source. The devices and methods provided herein can be configured to provide any of a range of light exposure depths 3500, such as between 10 μm and 5 mm, 20 μm and 4 mm, and any subranges thereof, such as between 20 μm and between 1 mm-2 mm.

Example 1: Devices and Methods for Light Delivery

The lack of availability, non-targeted nature, and inadequate light delivery into deep dermis of current light therapy devices underscore the need for more accessible, selective, and high-efficacy light therapy devices. Using advanced techniques in flexible electronics, provided herein is a soft, conformable, and depth-modulated phototherapy device. The device's top layer has an array of light emitting diodes of various wavelengths (e.g. UVA-1 LEDs with a spectral peak output of 360-nm), fully embedded within a substrate, including a flexible silicone. The bottom layer includes a dense array of tissue penetrating members, such as microneedles from bioresorbable poly-lactic-co-glycolic-acid (PLGA), a polymer enabling 99% of UVA transmittance, which create micro-channels 700 μm for deeper UVA-1 delivery into the skin. Optical modeling, confirmed by confocal microscopy in agarose, demonstrates that the PLGA microneedle waveguides increase light transmission in deep skin below 500 μm. The conformable nature of the device means the device can conform to any curvilinear body surface shape and be tailored specifically of any shape or size.

The methods and devices are compatible with a wide range of applications, including: Skin Diseases—Fibrotic diseases: morphea, keloids, scars; Neoplastic: cutaneous T-cell lymphomas, actinic keratoses, skin cancers (non-melanoma) Rheumatology: Systemic sclerosis; Cosmetic Dermatology: Skin rejuvenation; Collagen rejuvenation; Hair rejuvenation; Cardiology—Deployment of therapeutic LEDs (UVA-1, red light, blue light) on cardiac stents, cardiac guidewires, cardiac catheter balloons; Photodynamic Therapy—The microneedles may be impregnated with photosensitizing topical medications that is then activated with light. For instance, one embodiment includes microneedle elution of amino-levulinic acid that is then subsequently activated by blue light.

The integrated wearable device is designed for augmented skin therapy, including in the comfort of a user's home. The flexible design allows for conformal contact with curvilinear skin. The device exposes light limited to the affected area, thereby decreasing or avoiding exposure to unwanted skin regions. Furthermore, the microneedle array facilitates deeper light delivery in the skin.

Broadly, the methods and devices provided herein augment the delivery of therapeutic light. The primary mechanism is by increasing depth penetration. Specifically, we demonstrate microneedles that are engineered specifically to enhance optical light delivery from an integrated annealed top layer of LEDs embedded within a flexible substrate. We have constructed a wearable phototherapy device for several sclerotic skin diseases such as morphea (localized scleroderma). This device combines a flexible array of UVA-1 LEDs (360 nm) and a bioresorbable poly-lactic-co-glycolic-acid (PLGA) microneedle patch. Compared to the standard UVA-1 treatment of morphea by using mercury gas lamps with spectra filters, this wearable device provides more affordable therapy together with more effective light delivery in deep skin. It conforms to the curvilinear skin surface with a uniform output dosage of 20 J/cm$^2$. The tunable shape and form factor of the patch avoids the exposure to unaffected area. Moreover, the PLGA microneedle array, as light delivery device, delivers ~400% more light into deep skin below 500 μm, whereas the standard care only treats superficial lesions due to the limited UVA-1 penetration depth. Such integrated devices combining an LED array having any range of a specific wavelength and bioresorbable microneedle light guides present a versatile and potent platform for advanced skin therapy treatment, photodynamic therapy (including through the introduction of drug elution, such as from any of the tissue penetrating members), as well as fundamental photochemical study of biomolecules and living cells.

The photochemical and photobiologic process of biomolecules, cells, and tissues at specific wavelengths has laid the foundation of phototherapy in dermatology, oncology, and others.[1] For instance, UVA-1 (340-400 nm) has shown significant therapeutic benefits in treating several sclerotic skin diseases such as morphea, systemic sclerosis and lichen sclerosis.[2] Morphea is a localized scleroderma characterized by excessive collagen deposition and thickened dermis (up to 2.6 mm)[3]. The underlying mechanism for the light therapy is that UVA-1 leads to the upregulation of collagenase and IFNγ, leading to decreased collagen I, collagen III, and TGF-β expression.[4] While considered as an effective approach, the conventional UVA-1 light therapy (or standard care) is conducted by using mercury gas lamps with spectral filters. These apparatus, either physician office-based or home unit, are not widely available or cost-effective, and unable to selectively treat the affected area. Thus light dose is applied to both target skin lesions as well as normal skin, introducing a potential risk of undesirable photodamage of tissues. More importantly, the limited light penetration depth of UVA-1 in skin (<150 μm) presents a grand challenge in light therapy,[5] prohibiting efficient treatment of morphea in deep skin.

The lack of availability, non-targeted nature, and inadequate light delivery into deep dermis underscore the need for more accessible, selective, and high-efficacy light therapy devices. We propose an integrated, wearable device combining a flexible UVA-1 LED array with the peak emission at 360 nm and a microneedle patch serving as light guide. Taking advantage of the flexible design, it fits the curvilinear nature of human skin and can be readily used at home. The form factor of the whole device is comparable to the typical lesion size of morphea, which allows for treatment only at the target area. We deploy a compact array of LEDs to achieve a uniform and tunable irradiance, depending on the driving current. The use of bioresorbable poly-lactic-co-glycolic-acid (PLGA) microneedles (MNs) was inspired by the recent progress on microneedle based transdermal drug delivery.[6] Instead of being a transferring media for drugs, the PLGA MNs are highly transparent in the UVA region (transmittance >98%) with a refractive index similar to those of epidermis and dermis, acting as a light guide to distribute more light into deeper skin. As suggested by Monte Carlo simulation, compared to the standard care, the new device with MN light guides is expected to deliver 4 times more dosage to deep tissues from 500 μm to 1 mm. The UVA-1 dosage on both superficial, shallow skin layers as well as deep tissues would significantly enhance the therapeutic efficacy on morphea and other localized scleroderma diseases. In addition, the integrated device combining the LED light source as well as the bioresorable light engineering unit in a flexible form is a versatile platform for a broad range of light therapy and photomedicine related applications.

FIG. 1A shows an exploded scheme of the integrated device containing two functional units: i) a 3 by 3 array of light sources (UVA-1 LEDs) and ii) the bioresorbable PLGA MNs as light guide (e.g., microarray of tissue penetrating members). The LEDs are assembled on a polyimide substrate (75 μm thick) with 18 μm-thick copper circuits and encapsulated with an encapsulation layer (such as a thin layer of polydimethylsiloxane (PDMS, <10 μm)) for electrical insulation. Uncured PDMS was also used as the adhesive to bond the LED array and PLGA MNs. The refractive indices for PDMS encapsulation/adhesive layer and PLGA are about 1.43 and 1.45, respectively.[7-8] Such an index-matching results in negligible reflection loss when UVA light from the LED patch transmits into the PLGA MNs. FIGS. 1B and 1C show the photographs of the integrated device, which connects to custom-printed circuit board as an interface via ACF flexible cable to power source. Moreover, PLGA is highly UV transparent (measured transmittance >98% in the UVA wavelength range).

Recent progress on the integration of light-emitting devices with biological systems has been translated into clinical technologies such as sensing[9] and optogenetics.[10-11] Two optical parameters are crucial for the efficacy of light therapy, light intensity (irradiance) and the uniformity. In the standard care of morphea treatment, the mercury UVA lamp provides a uniform output with a typical light intensity of about 20 mW/cm² (can be as high as 80 mW/cm²,[12] depending on the treatment strategy). In the newly designed LED array, each LED has an area of 1.6 mm by 1.6 mm and a thickness of 1.0 mm (FIG. 2A). The minimal spacing between adjacent LEDs (~0.15 mm), together with the radiant pattern, leads to homogeneous light intensity distribution at ~1 mm above the top surface of the LED patch (FIG. 2C). The uniform light irradiation was confirmed by imaging the fluorescence of a commercial fluorophore (Dylight 350) dispersed in 4 wt. % Agarose gel. This fluorophore features with the emission between 400 and 500 nm under UVA-1 irradiation. Instead of directly imaging the UVA-1 light (challenging for most regular optical microscopes), by analyzing the fluorescence intensity in the visible light regime, one can extrapolate the intensity distribution of the excitation UVA-1 light (FIG. 2C). Within the LED array area (indicated by the dashed boxes in FIG. 2C), we analyzed the fluorescent intensity distribution along 9 randomly distributed lines and found the intensity remained largely unchanged (FIG. 2D). The highly uniform light intensity can reduce the chance of high intensity "hot spots", as potential risk for skin cancers, during the treatment. On the other hand, the light dose (radiant energy per area) and irradiance (radiant power per area) are important parameters for practical light therapy and photomedicine. A decent irradiance (e.g., 20 mW/cm²) is imperative to deliver adequate dosage within a reasonable amount of time. The high wall plug efficiency (~20%, defined as the percentage of LED converting electrical power into radiant power) of the UVA-1 LED results in light intensity (>20 mW/cm²) at a direct current as low as 20 mA. When outputting light intensity below 40 mW/cm², the LED array only induces a tolerable temperature increase (lower than 10 C, measured by a FLIR infrared camera).

Figure 3A:
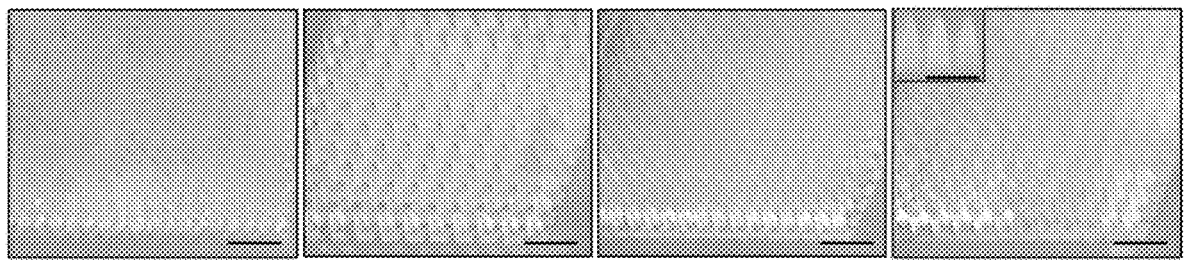
FIGS. 3A-3D. Configurations of the PLGA microneedle arrays and their penetration in real skin samples.
Figure 3B:
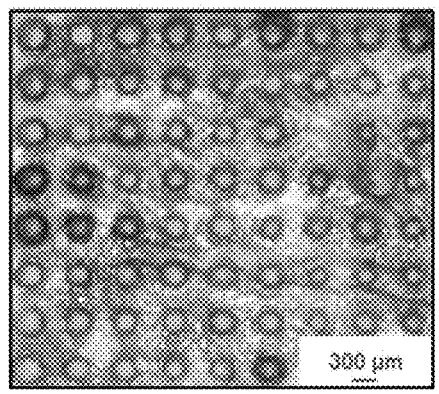
Figure 3D:
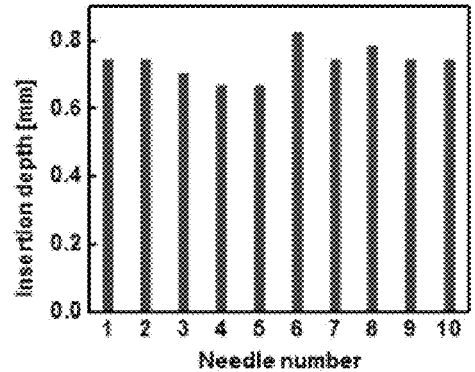
Figure 3C:
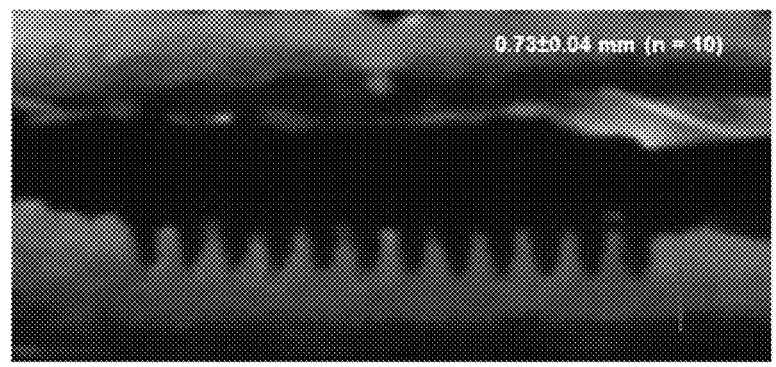

We deployed a bioresorbable copolymer, PLGA, in the preparation of MN light guide. PLGA is highly UV transparent. Thus we assume there is negligible light loss when UVA light propagates in the PLGA needles. The refractive index of PLGA (1.46)[7] is similar to those of epidermis (~1.49) and dermis (~1.40)[13-14], which dictates the light dissipation at the interface (see Monte Carlo simulation). Following a melt molding method in previous reports[6], we made high needle density PLGA MN arrays with several configurations. As shown in FIG. 3A, the pyramidal needles have 1 mm length and various combinations of base size (μm) and spacing between the edges of adjacent needles (μm). From left to right, the base size/spacing of the four arrays are 200/100, 400/200, 300/100, and 400/200, respectively. Such close packing translates to high occupancy (defined by the area of the base of needles divided by the area of the whole MN array) of 44%, 44%, 56%, and 64%, respectively. A high occupancy of MNs would allow more UVA-1 light delivered to deep skin if the needles can easily penetrate the skin. The high Young's modulus (1.4 GPa)[6] of PLGA and the sharp tips of the MNs (10-20 μm) allows for an efficient insertion into pig skin (as an alternative to human skin, the Young's modulus of skin is in the order of 100 kPa)[15], as visualized by the stained skin punctured by 1 mm long MNs (FIG. 3B, base/spacing=400/200 μm). The insertion depth is quantified by MRI imaging a PLGA MN array inserted in pig skin and sandwiched with another piece of skin (FIG. 3C). Due to the difference in water content/moisture of the MNs and the skin, the outlines of the inserted MNs were obvious from a cross-sectional view (FIG. 3C). The statistical analysis of the insertion depth of 10 selected needles showed an average insertion depth of 0.74±0.04 mm, which corresponds to ~75% of the length of needles. In addition to the listed configurations, conical MN arrays with needle lengths from 500 μm to 2 mm and occupancy as high as 44% can also be made using corresponding PDMS molds.

Figure 4A:
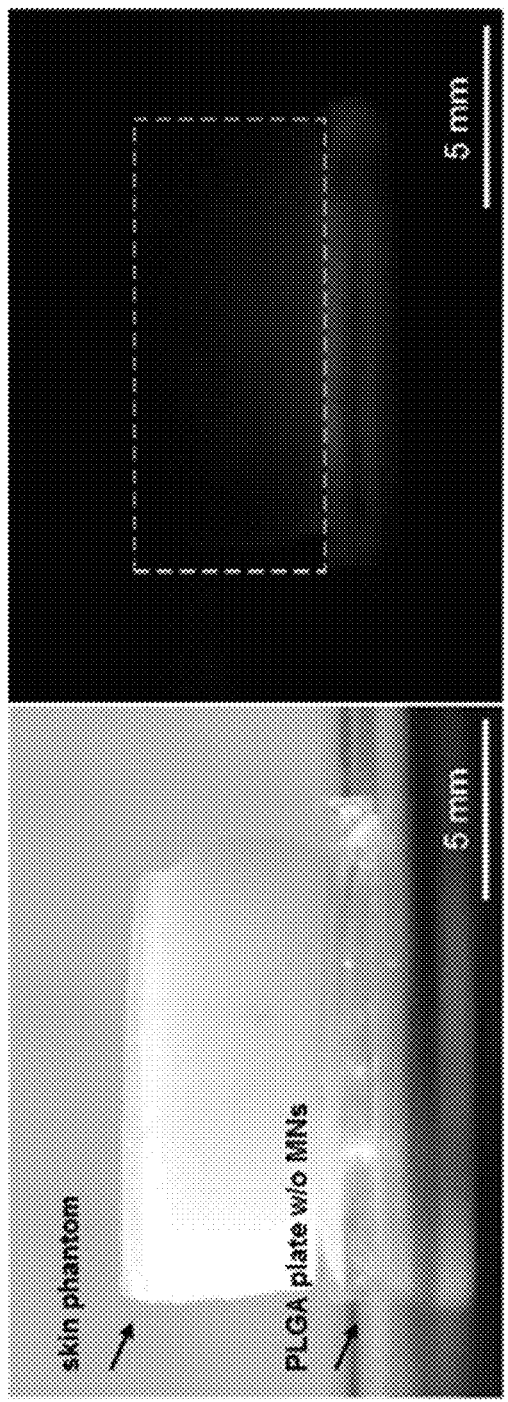
FIGS. 4A-4B. Optical visualization of the enhanced light dissipation in skin mimicking phantom via PLGA MNs.
Figure 4B:
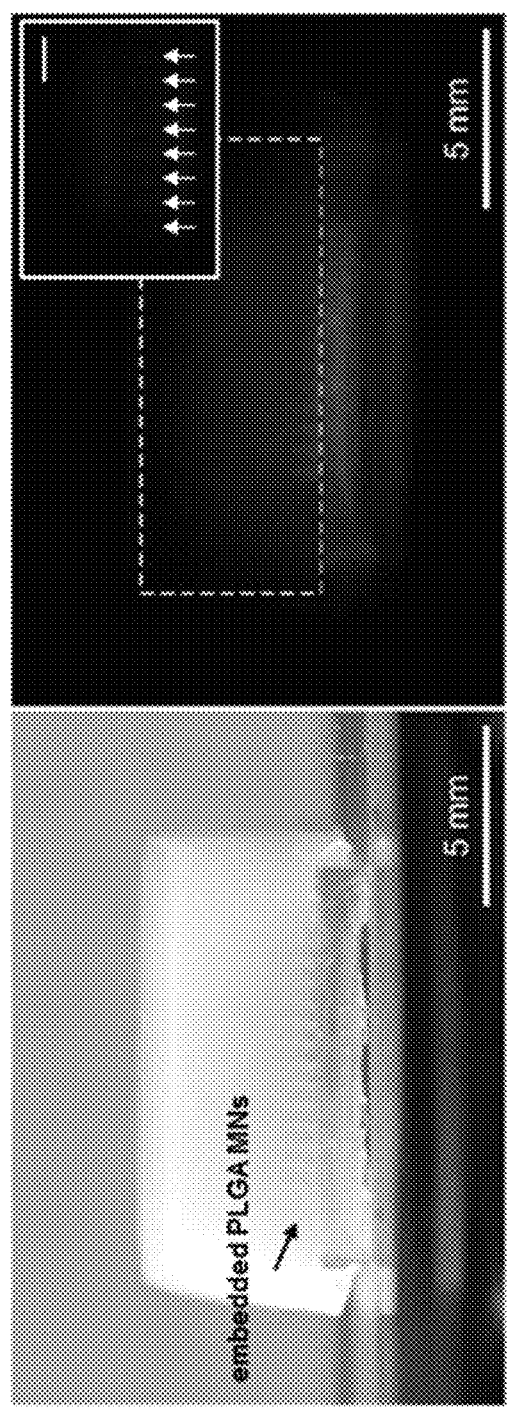
Figure 6:
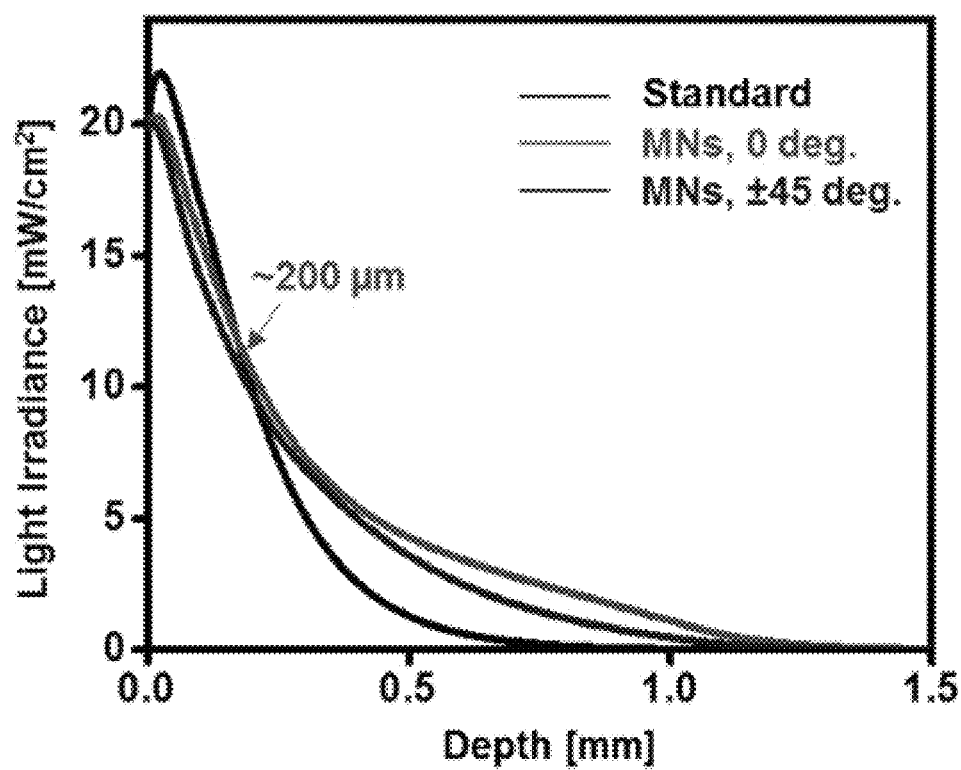
FIG. 6. Light irradiance (in $mW/cm^2$) at various depths in the skin (standard care versus microneedle (MN) case) calculated based on Monte Carlo simulation. The light intensity at the top of skin is set as 20 $mW/cm^2$ and the incident angle is either 0 deg. or ±45 deg. The MNs have dimensions of 1 mm length, 400 μm base size and 200 μm spacing. Note the crossover occurs at around 200 μm depth.

The key of the proposed integrated device for UVA-1 therapy is the enhanced delivery in deep skin via the tissue penetrating members (including microneedles or MN) light guide. To prove this concept, we performed both optical measurements and Monte Carlo simulation. A gelatin-based phantom with several additives (e.g., intralipid) was prepared to simulate the optical properties of skin.[16] A collimated 400 nm-light source was used to evaluate the light transport in skin mimicking phantom. In the scenario with PLGA MN light guides, there is an obvious increase in the light transport distance (FIGS. 4A-4B). To quantify the UVA-1 light dissipation in human skin with epidermis and dermis layers, we performed Monte Carlo simulation. This technique has proven the capability to estimate radiation dosages, such as light, in complex media where photons are subject to absorption as well as multiple scattering events.[17] As shown in FIGS. 5A-5F, the introduction of microneedles redistributes the light intensity and allows higher irradiance in deep skin, regardless of the illumination conditions: without divergence (i.e., incident angle=0 degree) or and sweeping with divergence (from divergence angle of ±45 degree). Beside the local light intensity distribution around each needle and an array, we can also obtain several other important information, including 1) irradiance (in mW/cm²) applied to skin at various depths; 2) dosage (in mW) delivered to skin at different depth intervals. FIG. 6 compares the irradiance at various depths in skin by standard care without MNs and the protocol with MNs (length=1 mm, base=400 μm, spacing=200 μm). The introduction of MNs leads to similar irradiance to the standard care in epidermis and slightly higher irradiance in dermis from 100 to 300 μm. Higher irradiance is expected in thicken dermis, especially below 500 μm. Clinically, morphea (localized scleroderma) has been shown to be as large as 2.6 mm in thickness (SC/E/Dermis) compared to 1.3 mm in thickness (SC/E/Dermis) of unaffected skin.[3] Therefore the enhanced light irradiance in thicken dermis would benefit the therapeutic response. Table 1 compares the dosage delivered at various depth intervals in skin by standard care and the protocols with microneedles. The total power is 9.8 mW. In the standard UVA-1 treatment, most of the light dose (~60%) is applied to the top 300 μm thick skin, while less than 10% energy can reach to thicken skin below 500 μm. Considering the typical thickness of morphea, most of the thicken dermis remained mostly untreated. In comparison, ~80% and ~40% (i.e., 4 times compared to standard care) of the light dose can be delivered to dermis layer (below 100 μm) and thicken skin below 500 μm, respectively, with the assistance of MNs.

TABLE 1

Dosage power (in mW) delivered at various depth intervals in the skin. The highlighted rows correspond to dose in epidermis and the top dermis.

| Depth intervals [μm] | Standard UVA-1 [mW] | UVA-1 with MNs (0 deg.) [mW] | UVA-1 with MNs (±45 deg.) [mW] |
|---|---|---|---|
| 0-200 | 4.91 | 2.79 | 3.59 |
| 200-300 | 2.33 | 1.70 | 1.73 |
| 300-400 | 1.26 | 1.29 | 1.35 |
| 400-500 | 0.66 | 1.00 | 1.06 |
| 500-600 | 0.32 | 0.77 | 0.75 |
| 600-700 | 0.16 | 0.66 | 0.55 |
| 700-800 | 0.08 | 0.54 | 0.38 |
| 800-900 | 0.04 | 0.45 | 0.27 |
| 900-1000 | 0.02 | 0.37 | 0.18 |
| 1000-1100 | 0 | 0.26 | 0.12 |
| 1100-1200 | 0 | 0.15 | 0.06 |
| 1200-1300 | 0 | 0.07 | 0.03 |
| 1300-1400 | 0 | 0.04 | 0.02 |
| 1400-1500 | 0 | 0.02 | 0.01 |

Figure 7A:
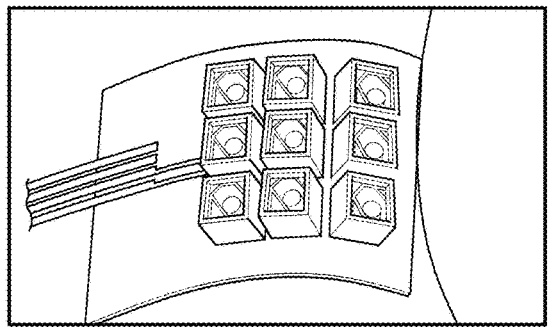
FIGS. 7A-7D. Demonstration of the flexible, wearable integrated light therapy device.
Figure 7B:
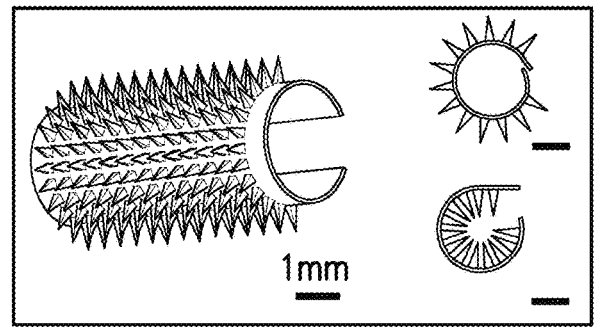
Figure 7C:
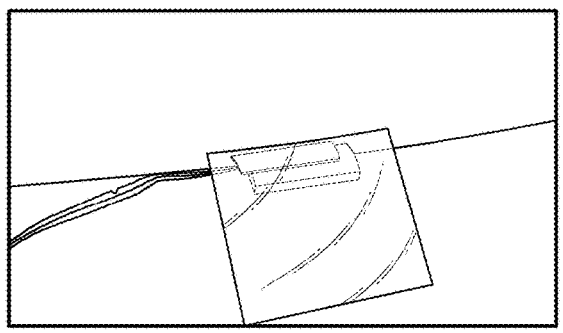
Figure 7D:
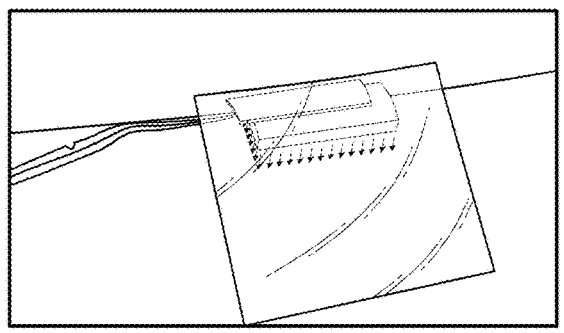

Finally, in view of the curvilinear nature of human skin, a flexible light therapy device is preferred, especially when treating morphea lesions in regions with high curvature such as elbows or joints. The LED patch on a 12.5 μm-thick polyimide substrate conforms to the curvature of a human finger without sacrificing the electrical/optical performance (FIG. 7A). Chemical modification of the handling layer of PLGA MN array leads to rigid MNs on a highly flexible handling layer (FIG. 7B). The bendability of PLGA MN arrays is high enough to accommodate most curvatures or surface roughness on human skin. FIGS. 7C and 7D show an operational, integrated flexible device applied to the arm of a human subject.

In conclusion, we provide a flexible, wearable integrated light therapy device utilizing dense microneedle arrays as a light guide to facilitate light delivery into deep skin. This provides a promising solution to treating skin disease such as morphea. Moreover, this technology could serve as a versatile platform for various light therapy, with different wavelength, light intensity, penetration depth, etc.

Fabrication of UVA-1 LED patch. The UVA LEDs with commercial packing (peak emission at 360 nm, VLMU1610-365-135) were purchased from Digikey. The flexible electronic circuit was defined by LPKF Contac S4 from DuPont Pyralus AP8535R (18 μm copper/75 μm polyimide/18 μm copper). The LEDs were mounted by low temperature solder (IndiumCorp). The LED patch was encapsulated with a thin layer of PDMS (DOW corning Sylgard 184, part A: part B=10:1). The device was powered by a precise direct current source meter (Keithley 6220, USA). Under a voltage compliance (5 V), a constant current was applied to achieve a desirable optical radiant power. The connection between the LED patch and the source meter was through a flexible ACF cable to a custom printed circuit board as an interface. The radiant power was measured by using a commercial UVA light meter (SPER Scientific 850009). The UVA light meter was calibrated with a UVA lamp with known light intensity. The temperature increase during the operation of LEDs was monitored by an IR camera.

Preparation of PLGA microneedles. Poly(D,L-lactide-co-glycolide) (PLGA, 430471-5g) was purchased from Sigma-Aldrich. We used laser-ablated molds made from PDMS (purchased from BlueAcre Technology, Ireland) with the negative patterns of the microneedles. PLGA pellets were placed in the mold and heated at 200° C. for 1 h in a vacuum oven (~25 mmHg). Under vacuum, the molten PLGA filled the cavities of PDMS molds. After cooled to room temperature, a couple of PLGA pellets were added to fill the uncovered area of the mold, followed by heated at 200° C. for 1 h under vacuum. After several cycles, the mold fully filled with molten PLGA was cooled in a refrigerator (−20° C.) for 30 min. The solidified PLGA array was then carefully separated from the mold. To make PLGA MNs with a highly flexible handling layer, prior to the separation between MNs and PDMS mold, several drops of ethyl acetate or acetone were carefully casted on the handling layer, followed by solvent evaporation in the fume hood. After several drop-cast/solvent evaporation cycles, the handling layer became high flexible while the needles remained rigid.

Characterization techniques. The microscopic images of Dylight 350 containing Agarose gel (1 μg of dye in 3 g of 4 wt. % Agarose gel) placed on top of the UVA-1 LED patch were taken on a Leica DM6B Widefield Fluorescent Microscope. The light intensity distribution of UVA LEDs was extrapolated by analyzing the fluorescence of Dylight 450. To visualize the light transport distance, gelatin-based phantom was prepared according to previous reports[16] to simulate the optical properties of skin. The insertion of MNs was visualized on Trypan blue (T8154, Sigma-Aldrich) stained pig skin after punctured by MNs. MRI was performed on a 9.4T Bruker Biospec MRI system with a 30 cm bore, a 12 cm gradient insert, and an Autopac automated sample positioning system (Bruker Biospin Inc., Billerica, MA).

Monte Carlo simulation. We performed Monte Carlo simulation to evaluate the light dosage in the skin, especially the dermis. The simulation consists of a light source (20 mW/cm$^2$) impinging on the skin in the presence of the microneedle array under two illumination conditions: without divergence (i.e., incident angle=0 degree) and with divergence (divergence angle of ±45 degree); and in the absence of the microneedles as a comparative frame. As described above, the closely packed UVA LED patch likely emits light with very narrow incident angles (<5 deg.). Nonetheless, we simulate both cases for better comparison. The total power coming from the LED patch is $P_{Total}=I_T*A_T=9.8$ mW, where $I_T=20$ mW/cm$^2$, $A_T$ is the area with microneedles (7 mm by 7 mm). Power per microneedle (MN) unit cell can be calculated as $P_{MN}=I_T*A_T/n_{Tip}$, where $A_{MN}$ is the area of the MN unit cell and also contains the spacing (d) and $n_{MN}$ is the number of unit cells. To simulate the optical properties of different skin layers, we adopt the absorption and scattering coefficients and the anisotropy factor from previous reports for the UVA wavelength band and assume a 100 μm epidermis layer on top of the dermis. The simulations were performed on a single unit cell. From that unit cell the total power and power outside the needle (the actual power introduced to the skin) were calculated. Then, the total contribution (power intensity or dosage in the skin) was calculated by adding (i) the power outside in each needle unit cell multiplying to the total number of MNs in the array and (ii) the power in the gaps between the needle unit cells (data obtained from the standard care cases where there are no microneedles). Based on the simulations, we can obtain several important information comparing the standard care and the proposed protocol with microneedle arrays, including 1) irradiance (in mW/cm$^2$) applied to skin at various depths; 2) dosage (in mW) delivered to skin at different depth intervals; 3) local light intensity distribution around each needle and a needle array. For all cases, we compared the standard care with the microneedle approach (collimated irradiation or ±45 deg. divergence).

REFERENCES (FOR EXAMPLE 1)

1. Dougherty, T. J.; Gomer, C. J.; Henderson, B. W.; Jori, G.; Kessel, D.; Korbelik, M.; Moan, J.; Peng, Q., Photodynamic Therapy. J. Nat. Cancer Inst. 1998, 90, 889-905.
2. Group, A. A. o. D. W.; Menter, A.; N. J., K.; Elmets, C. A.; Feldman, S. R.; Gelfand, J. M.; Gordon, K. B.; Gottlieb, A.; Koo, J. Y.; Lebwohl, M.; Leonardi, C. L.; Lim, H. W.; Van Voorhees, A. S.; Beutner, K. R.; Ryan, C.; Bhushan, R., Guidelines of Care for the Management of Psoriasis and Psoriatic Arthritis: Section 6. Guidelines of Care for the treatment of Psoriasis and Psoriatic Arthrits: Case-Based Presentations and Evidence-Based Conclusions. J. Am. Acad. Dermatol. 2011, 65, 137-174.
3. Serup, J., Localized Scleroderma (Morphoea): Thickness of Sclerotic Plaques as Measured by 15 MHz Pulsed Ultrasound. Acta. Derm. Venereol. 1984, 64, 214-219.
4. Wong, T.; Hsu, L.; Liao, W., Phototherapy in Psoriasis: A Review of Mechanisms of Action. J. Cutan. Med. Surg. 2013, 17 (1), 6-12.
5. Meinhardt, M.; Krebs, R.; Anders, A., Wavelength-Dependent Penetration Depths of Ultraviolet Radiation in Human Skin. J. Biomed. Opt. 2008, 13, 044030.
6. Park, J. H.; Allen, M. G.; Prausnitz, M. R., Biodegradable Polymer Microneedles: Fabrication, Mechanics and Transdermal Drug Delivery. J. Control. Release 2005, 104, 51-66.
7. Butler, S. M.; Tracy, M. A., Adsorption of Serum Albumin to Thin Films of Poly(lactide-co-glycolide). J. Control. Release 1999, 58, 335-347.
8. Raman, K.; Srinivasa Murthy, T. R.; Hegde, G. M., Fabrication of Refractive Index Tunable Polydimethylsiloxane Photonic Crystal for Biosensor Application. Phys. Procedia 2011, 19, 146-151.
9. Kim, D.-H.; Lu, N.; Ghaffari, R.; Kim, Y.-S.; Lee, S. P.; Xu, L.; Wu, J.; Kim, R.-H.; Song, J.; Liu, Z.; Viventi, J.; de Graff, B.; Elolampi, B.; Mansour, M.; Slepian, M. J.; Hwang, S.; Moss, J. D.; Won, S.-M.; Huang, Y.; Litt, B.; Rogers, J. A., Materials for Multifunctional Balloon Catheters with Capabilities in Cardiac Electrophysiological Mapping and Ablation Therapy. Nat. Mater. 2011, 1, 316-323.
10. II Park, S.; Brenner, D. S.; Shin, G.; Morgan, C. D.; Copits, B. A.; Chung, H. U.; Pullen, M. Y.; Noh, K. N.; Davidson, S.; Oh, S. J.; Yoon, J.; Jang, K. I.; Samineni, V. K.; Norman, M.; Grajales-Reyes, J. G.; Vogt, S. K.; Sundaram, S. S.; Wilson, K. M.; Ha, J. S.; Xu, R. X.; Pan, T. S.; Kim, T. I.; Huang, Y. G.; Montana, M. C.; Golden, J. P.; Bruchas, M. R.; Gereau, R. W.; Rogers, J. A., Soft, Stretchable, Fully Implantable Miniaturized Optoelectronic Systems for Wireless Optogenetics. Nat. Biotechnol. 2015, 33, 1280-1286.
11. McCall, J. G.; Kim, T.-i.; Shin, G.; Huang, X.; Jung, Y. H.; Al-Hasani, R.; Omenetto, F. G.; Bruchas, M. R.; Rogers, J. A., Fabrication and Application of Flexible, Multimodal Light-Emitting Devices for Wireless Optogenetics. Nat. Protoc. 2013, 8, 2413-2428.
12. Hassani, J.; Feldman, S. R., Phototherapy in Scleroderma. Dermatol. Ther. (Heidelb) 2016, 6, 519-553.
13. Meglinski, I. V.; Matcher, S. J., Quantitative Assessment of Skin Layers Absorption and Skin Reflectance Spectra Simulation in the Visible and Near-Infrared Spectral Regions. Physiological Measurement 2002, 23, 741-753.
14. Salomatina, E.; Jiang, B.; Novak, J.; Yaroslaysky, A. N., Optical Properties of Normal and Cancerous Human Skin in the Visible and Near Infrared Spectral Range. J. Biomed. Opt. 2006, 11, 064026.
15. Liu, Y.; Pharr, M.; Salvatore, G. A., Lab-on-Skin: A Review of Flexible and Stretchable Electronics for Wearable Health Monitoring. ACS Nano 2017, 11, 9614.
16. Chen, A. I.; Baiter, M. L.; Chen, M. I.; Gross, D.; Alam, S. K.; Maguire, T. J.; Yarmush, M. L., Multilayered Tissue Mimicking Skin and Vessel Phantoms with Tunable Mechanical, Optical, and Acoustic Properties. Med. Phys. 2016, 43, 3117-3131.
17. Glinec, Y.; Faure, J.; Malkaa, V.; Fuchs, T.; Szymanowski, T.; Oelfke, U., Radiotherapy with Laser-Plasma Accelerators: Monte Carlo Simulation of Dose Deposited by an Experimental Quasimonoenergetic Electron Beam. Med. Phys. 2006, 33, 155-162.

Example 2: Phototherapy

Narrow-band ultraviolet-B radiation (NBUVB) phototherapy is effective, safe even for pregnant women and children, and affordable for psoriasis. However, NBUVB takes a long time to work (~3 months), is inconvenient, does not clear skin as well as newer injectable drugs, and only penetrates very shallowly. We propose a new 'patch-like' NBUVB technology. The device's top layer has micro-light-emitting diodes that emit NBUVB embedded within soft, flexible silicone that wraps around psoriasis lesions on curvy body surfaces. The second layer, attached to the skin, includes a microneedle patch with tiny needles (length: 100 μm) designed to guide NBUVB deeper into the psoriasis lesion. We think that tighter wrapping and depth enhancement will improve the speed and effectiveness of NBUVB. We have already shown that we can make a device to deliver a different type of light. The three goals of this example are to modify the system to deliver NBUVB with shorter microneedles. The second is to show the system works on the benchtop. The third is to show the device is safe and works in patients with psoriasis. The device is configured to be available for home-use that can be 'cut' to size to treat any psoriatic lesion.

Phototherapy is the standard of care for several moderate-to-severe immune-mediated skin disorders, among them psoriasis (inflammatory scaling disorder), vitiligo (pigmentary loss), and morphea (localized scleroderma). Topical anti-inflammatory medications—especially topical corticosteroids—have remained the treatment of choice for most immune-mediated skin disorders of milder severity or more localized disease for decades. However, these topical therapies often have limited efficacy, and patients adhere poorly to treatment regimens because of concerns about side effects and inconvenience. In severe cases, immunosuppressive agents can be effective but are costly, particularly in the case of biologics, and have systemic side effects. Thus, augmented forms of phototherapy that is more efficacious, faster in delivering therapeutic response, affordable, and suitable for home use would offer a significant therapeutic advance.

UVB (290-320 nm) and more specifically narrow-band ultraviolet light (NBUVB, 311 nm) have shown excellent efficacy for psoriasis on a par with injectable biologics therapy. Phototherapy has no systemic side effects such as immunosuppression, and is safe to use in pregnant women.[1] In psoriasis, NBUVB reverses the pro-inflammatory cytokine profile by shifting the immune response towards the Th2 axis and away from the Th1/Th17 axis that drives the disease; another key mechanism involves NBUVB's induction of apoptosis and depletion of T lymphocytes in psoriasis lesions.[2] Meta-analyses demonstrate that 75% of psoriasis patients have at least a 75% reduction in the Psoriasis Area and Severity Index (PASI) after 4-6 weeks of NBUVB treatment, making phototherapy one of the most efficacious therapies.[3] The annual economic disease burden is up to $35.2 billion USDs[4] with a prevalence of 3% among U.S. adults.[5] The psoriasis disease burden, coupled with the established efficacy of NBUVB phototherapy makes psoriasis an ideal test platform.

UVA1 (340-400 nm) has shown distinct biological effects from UVB. Given the longer wavelength, UVA1 penetrates deeper into tissue (dermis and superficial fat), delivering therapeutic benefit in sclerotic skin diseases with limited therapeutic options, such as morphea, systemic sclerosis and lichen sclerosis.[6] Phototherapy's therapeutic effect has been attributed to: i) reducing fibroblast expression of TGF-β, a key growth factor in propagating fibrosis; ii) increasing collagenase mRNA expression 20-fold; iii) causing apoptosis of infiltrating T-cells; and iv) inducing neo-vascularization.[6,7,8]

Existing NBUVB and UVA1 Phototherapy Systems: NBUVB is traditionally delivered via mercury gas lamps (Philips TL01) with spectral filters that are inherently inefficient and require high-energy input. In addition, these mercury gas lamps have limited shelf lives, requiring frequent replacement because of decreased performance with time. Furthermore, traditional NBUVB systems are limited in their ability to be selective in regards to treatment area. Thus, energy is delivered to both target psoriatic lesions and normal skin and, because of the lower tolerance to UVB radiation of normal skin (erythema and pain), must be slowly over weeks before a therapeutic dose is delivered to the psoriatic lesion.[9] NBUVB is typically first given to a patient in a physician's office to assess tolerance and skin response. Patients come to the office 2-3 times a week for therapy, leading to an untenable burden of both cost and inconvenience in comparison to other available treatment options:[10] Although home phototherapy units are effective, few patients are able to utilize home therapy; both insurance coverage issues and patient safety concerns dictate the need for a several month period of physician office-based phototherapy before home phototherapy units become an option.[11] The xenon-chloride excimer laser is able to deliver targeted NBUVB therapy to a smaller surface area.[12] With the advantage of higher energy delivery to only lesional skin, the excimer laser still exhibits significant limitations. The device is highly expensive, poses an ophthalmic risk, and not suitable for home use. Although UVA1 causes significantly less skin erythema compared to NBUVB and thus enables the delivery of more energy, UVA1 to unaffected skin leads to skin hyperpigmentation, premature photoaging, and an increased risk of cutaneous malignancy.[13] To avoid this, patients must put on layers of protective clothing. This can be uncomfortable, given the length of time necessary for UVA1 phototherapy (>15 minutes per session) and the heat generated by the systems. Finally, UVA1 remains challenging to obtain, given that few providers offer UVA1 phototherapy. Both UVA1 and NBUVB require titration of the light dose to accommodate skin tolerance. Since the wavelengths for UVA1 and NBUVB are relatively short, there is limited skin penetration, which precludes the ability to treat skin lesions more than 1 mm thick.

The development of aluminum gallium nitride and aluminum nitride materials has enabled the fabrication of light emitting diodes (LEDs) with emission wavelengths less than 400 nm,[14-15] which are commercially available. There are several advantages to the use of LEDs for UVB and UVA light delivery. First, LEDs exhibit significantly higher shelf life and robust performance over time, compared to gas lamp systems. Second, LEDs are much more affordable to manufacture than excimer laser systems. Third, LEDs can be specifically constructed to emit a narrow spectral band (e.g. 311 nm), negating the need for extraneous filters, which lead to heat generation and energy inefficiency. Lastly, LEDs can operate using direct current, enabling battery power for operation with no cool-down or warm-up necessary. Previous studies have demonstrated the preliminary clinical efficacy of NBUVB therapy with LEDs using a prototype device[9]; there are existing FDA-cleared LED phototherapy devices (e.g. Psoria-Shield™) approved for the treatment of psoriasis. However, new LED phototherapy devices simply recapitulate gas lamp systems without significant improvements in device wearability, patient convenience, and phototherapy efficacy. Currently, there is a need for more effective, more convenient, and wearable home UVB and UVA phototherapy systems. Innovation in this field will deliver significant patient benefit by augmenting the efficacy of phototherapy for a range of dermatological conditions.

Definitions of Optical Parameters: Irradiance ($mW/cm^2$): radiant energy flux per unit area. In assuming light is considered a therapeutic class, irradiance would effectively represent the 'medicine'. Radiant Exposure ($mJ/cm^2$): irradiance of a surface integrated over time of irradiation or simply the radiant exposure received by a surface per unit area. In assuming light is considered a therapeutic class, radiant exposure would effectively represent the 'dose'. Pulse configuration: describes the pulse characteristics of the light energy being delivered. This can represent either high intensity short pulses or low intensity sustained pulses. Dose time: relates to the time necessary to deliver a specific radiant exposure for a given irradiance.

Advantages of Flexible Electronics: The development of curvilinear, hyper-flexible epidermal electronics using inorganic semiconductor materials was pioneered by the Rogers group.[16] Through photolithographic patterning and chemical etching techniques, silicon ribbons and membranes with thicknesses in the nanoscale range can be created from a source silicon wafer. Through transfer printing, these nanoribbons and nanomembranes can be deployed on an elastomer such as (poly)dimethylsiloxane (PDMS) from their source wafer.[17] The ability to create bendable connections enables the development of novel flexible devices. Low profile silicon metal oxide semiconductor field-effect transistors (MOSFETs) can be deployed within the PDMS substrate and connected with nanoribbons to create devices of a myriad of functions. The relationship between the mechanics of the silicon ribbons and performance has been tested extensively in the lab. Serpentine ribbon configurations enable strain of up to 30% or more without deterioration in performance.[18] There is demonstrated robustness and high-performance of those devices in measuring a wide range of clinically useful parameters, including but not limited to: temperature, blood flow, stretch, ambient UVA and UVB exposure, EKG, EEG, and EMG.[19] Given the use of inorganic semiconductor materials and standard manufacturing techniques, flexible electronics offer both novel functions as well as a highly favorable cost profile.

Novel LED technologies (FIG. 9) have been developed, including inorganic μLEDs in flexible substrates.[20] The μLEDS can be created with a wide range of dimensions from as large as 1×1 $mm^2$ to as small as 25×25 $\mu m.^2$ The flexible μLEDs are fabricated using transfer printing on a flexible PDMS substrate. The thermal dissipation properties of μLEDs placed within flexible substrates have also been characterized within the lab. Through both experimental and theoretical monitoring techniques,[21] heat flow within these structures has shown passive cooling through direct thermal transport of flexible metallic wires. Alterations of LED density and geometric configurations can be optimized depending on the necessary irradiance of the LED and desired radiant exposure.

Novel Use of Microneedles as Optical Waveguides: Increasing Cutaneous Penetration Depth The optical power of an incident light at 311 nm (NBUVB) and 340 nm (shorter end of UVA1) is limited to 60 μm and 100 μm, respectively,[22] translating into limited penetration into the epidermis (NBUVB) and upper reticular dermis (UVA1). Sclerotic diseases such as morphea affect the entire dermis and subcutis, which are millimeters deep. There is an opportunity to tune penetration for thicker skin lesions or in applications that extend to the subcuticular tissue.

Research in flat planar microneedles has largely focused on the use of these tools for vaccine and drug delivery. In dermatology, microneedles have also been studied as aesthetic devices for treating facial wrinkles and acne scarring. As FDA-registered low-risk Class I medical devices, these are available for consumer purchase without a physician's prescription or supervision.[23] These devices involve rolling small needles of set length (0.5 mm to 4 mm) repeatedly over the skin treatment area to create painless micro-punctures that augment the efficacy of topical drugs. Microneedles may serve another purpose as useful conduits to enhance light delivery to the skin ("waveguides"). While implantable polymers have been developed to guide light, these devices require a surgical procedure to implant and are limited to the delivery of longer wavelength (visible light).[24]

Provided herein is a new medical device to deliver UV phototherapy capable of targeting deeper tissue depths. Through initial bench validation and optical simulations, a flexible microneedle light therapy system directly adhered to the skin provides advantages over existing clinical-standard phototherapy systems. To address the issue of light penetration, we provide coupling of a microneedle waveguides optically engineered to deliver short-wavelength light (UVB and UVA) with a flexible substrate embedded with UV LEDs, to enhance therapeutic effect.

Phototherapy is as efficacious as TNF-α inhibitor therapy and has an excellent safety profile (including as first-line therapy in pregnant women with psoriasis).[25] However, the utilization of light therapy has declined in popularity in comparison to biologics therapy[26] due to the difficulty in obtaining access and the longer time before clinical efficacy compared with biologics.[26-28] The development and validation of flexible microneedle light therapy system with optical microneedle waveguides would represent a new home-based therapeutic paradigm for phototherapy, especially for more localized lesions.

Beyond lower cost and greater convenience, a flexible microneedle light therapy device integrated on skin lesions offers the potential for increased clinical efficacy. This hypothesis is based on several fundamental physics laws governing light delivery. Traditional NBUVB and UVA1 gas-lamp systems require users to stand within a large booth. The distance between the gas-lamps and the user is at least 6 cm. Although LEDs contain a lens (in contrast to the gas lamp systems), experimental models have demonstrated that LED sources still follow a modified inverse square law[29], meaning that irradiance decreases proportional to the square of distance when assuming an isotropic radiator. Practically, a light therapy device intimately mated to the skin enables the same therapeutic effect by reducing surface reflection, and energy loss with distance.[30] The ability to intimately integrate with the skin through a flexible microneedle light therapy system will enable more precise and direct delivery of light. The reduction in distance between the irradiance source (UV-LED) and the target (psoriasis) by at least one order of magnitude will enable increase the effectiveness of the irradiance and/or reduce the power requirements to deliver the same effective irradiance to the skin.

For many inflammatory skin lesions and neoplasms, the lesion extends beyond the surface of the surrounding skin. For example, the histopathology of psoriasis is characterized by a thickened stratum corneum and hyperplasia of the epidermis. Thus, psoriatic lesions extend above the plan of normal skin. A flexible microneedle light therapy device has the advantage of allowing for targeted phototherapy across the entire area of the skin lesion, including the portion of the lesion that extends above the surface of unaffected skin (e.g. the sidewall of a thicker psoriatic lesion). Existing phototherapy systems only treat lesional skin perpendicular to the orientation of the lamps. Thus, a system able to deliver UV light along the surface area and height of any skin lesion (e.g. psoriasis) would enable superior efficacy.

FIG. 10 is a schematic that indicates how the microneedle tips augment the delivery therapeutic light for improved clinical efficacy and faster response. Therapeutic UVA1 is disseminated throughout the entire length of the microneedles as well as the tip. The ability to direct light delivery to various tissue depths provides a therapeutic advantage over existing systems. The significance of this research extends beyond improving phototherapy for dermatoses already known to be responsive to phototherapy (e.g. morphea or psoriasis). Skin lesions or growths that extend below the epidermis and upper dermis susceptible to UV therapy would potentially be treatable with phototherapy opening new opportunities for clinical applications and research.

The tissue penetrating member is compatible with additional optical components to provide a controlled light intensity profile to surrounding tissue, including as a function of penetration depth. For example, FIG. 42 illustrates an optical component that is a coating layer that blocks light, such as a UV blocker. In this manner, light intensity can vary as a function of penetration depth.

In Silico Experiments to Determine Optimal Microneedle Waveguide Geometries and LED Operation Using MatLab's (MathWorks, Natick, MA) optical simulation toolbox, we have determined preliminary configurations of microneedles for the delivery of UVB and UVA1 light. First, we model the behavior of light within skin tissue by plugging in absorption coefficients and scattering coefficients of skin, as previously determined.[31] Simulations enabled us to determine the effect of needle geometry (e.g. tetrahedral, conical). In our preliminary data, we demonstrate the simulated light dissipation of UVA1 across the length of a tetrahedral microneedle. Identifying the optimal polymer for microneedle composition requires consideration of optical transparency (so that the light can get into the surrounding tissue), stiffness (to ensure skin penetration), and biocompatibility. We have identified poly lactic-co-glycolic acid (PLGA) as one target polymer, given its excellent optical properties, high stiffness, and excellent biocompatibility.[32] Alternatives include polylactic acid, poly-methyl-methacrylate, and carboxymethyl cellulose. Finally, the density of the microneedles are assessed with simulations to determine how decreasing microneedle pitch (distance between each individual needles) increases light transmission. As shown below (FIG. 11), the presence of the microneedles significantly increases UV light dissipation in skin (compare 1000 µm to 400 µm).

There are several important safety parameters to consider. The UV LEDs are theoretically modeled with respect to heat dissipation when embedded in various flexible substrates such as PDMS. The encapsulation of the device with various flexible substrates affects heat dissipation. We have experience with finite element modeling (FEM) of the performance of LEDs in flexible substrates using commercially available software (ABAQUS).[33] For this example, we model light-current-voltage curves for UV-LEDs of varying sizes. This means that with increasing current input from a battery source, we will know how much heat is created and dissipated. Given the intimate connection with the epidermis, temperature dissipation is a critical consideration. Thus, careful modeling will be performed to assess how changes in temperature vary with inputted power. Detailed thermal analyses and modeling have been performed previously for LEDs deployed in a flexible configuration and layout.[34] This previous work provides a specific heat transfer model that can be deployed for the specific aims in this proposal involving multiple arrays of LEDs. In instances where heat generation exceeds 10° C. (threshold of pain in humans), we will vary the geometry of the LEDs. This may include changing parallel arrays into hexagonal arrays within a standard surface area (2 cm×2 cm). Combined with optical and optoelectronic modeling, we determine the maximum LED density allowable before temperature changes degrade performance or represent a risk for thermal injury. Multiple substrates with varying thermal conductivity characteristics are tested.

For example, FEM analysis will include PDMS (0.15 W/m/K), glass (1.4 W/m/K), benzocyclobutene (0.3 W/m/K), polyethylene terephthalate (0.15 W/m/K), and composite silicones. The power requirements will then be calculated depending on the final allowable LED density. The FEM analysis will also analyze component buckling with various levels of strain.[35] The characterization of the mechanics of the device will allow us to select the ideal elastomer, and ensure device performance when deployed on human skin. Finally, we have experience in deploying multiple power options including the use of embedded batteries, near field communication (NFC) chips, and Bluetooth.[17] Our design goal is to ensure that at least 1 mW/cm² of irradiance is delivered predominately in the spectral band between the excimer laser (308 nm) and the Philips TL01 mercury gas lamps (311 nm) while ensuring adequate temperature dissipation. Modeling will ensure the device will operate with the desired characteristics. Our current preliminary data demonstrates increased UVA1 delivery which can be further improved with additional microneedle geometries, microneedle density configurations, and LED density configurations to further optimize light delivery for NBUVB and UVA1.

Develop and Characterize Microneedle Designs Optically Engineered for NBUVB and UVA1 Light Delivery Additional microneedle molds are optically engineered for light delivery for UVA1 and NBUVB light. This requires consideration of several factors including biocompatibility, optical transparency, and mechanical robustness. Matching epidermis and dermis refractive index enables the optimal dissipation of UVA1 and NBUVB light based on the Fresnel Equation of light loss by reflection. Poly(lactic-co-glycolic acid) or PLGA represents an optimal polymer given its good refractive index match and high stiffness (2 GPa), which enables epidermal and dermal penetration. Construction of the microneedle array can be accomplished with several strategies. Molds from PDMS can be made from metal microneedle masters available off-the-shelf. In our preliminary data, we took an off the shelf metal mold to create a negative mold. Then, we embedded solubilized PLGA and poured it into this mold. The PLGA microneedles are shown here with transmission electron microscopy illustrating the array of microneedles. The length of the needles is 700 µm with a pitch distance of 500 µm (space between needles).

Although using microneedle masters is a straightforward construction method, further changes may enable more control over microneedle density. This includes strategies such as electroplating of metals into denser microneedle masters. Denser microneedle arrays would further increase UV light delivery. While PLGA is a promising, biocompatible material, other polymers such as poly(vinyl pyrrolidone) PVP or polylactic acid (PLA) may offer advantages. This includes better optical matching to increase UV light dissipation or softer microneedles that are more comfortable for patients (see, e.g., Table 2).

TABLE 2

Multiple polymers represent potential materials for the microneedles.

| Polymer | Young's Modulus | Refractive Index |
| --- | --- | --- |
| Polylactic Acid (PLA) | 3.5 GPa | 1.53 |
| Poly(vinyl pyrrolidone) (PVP) | ~1 GPa | 1.55 |
| Poly(lactic-co-glycolic acid) (PLGA) | ~2 GPa | 1.46 |
| PDMS | <3 MPa | 1.40 |
| Epidermis | | 1.47 |
| Dermis | | 1.40 |

Histological Testing of Microneedle Performance

Ex vivo testing of microneedle performance on cadaveric porcine skin, an accepted model for microneedle validation[36], can be utilized. Using our preliminary molds of PLGA, I applied them to cadaveric porcine skin to demonstrate the successful formation of microneedle channels after insertion. Although the needles are 700 µm in length, the microneedle channels in H&E histology vary from 200-400 µm. This discrepancy is likely fixation artifact. We can utilize longer microneedles and further histological characterization of penetration.

Evaluating Light Dissipation in the Microneedle Waveguides

The evaluation of the PLGA microneedles shows lateral and deep light dissipation. These experimental data are obtained using agarose gel penetrated by our PLGA microneedles. Confocal microscopy is used to measure the intensity of fluorescence (visible green light) through the light channels created by the microneedle waveguides. We use visible green light given the ease of visualization. Further experimentation under will involve testing the dissipation of UV-light and a UV-spectrophotometer (Ocean Optics) within the lab.

Figure 13:
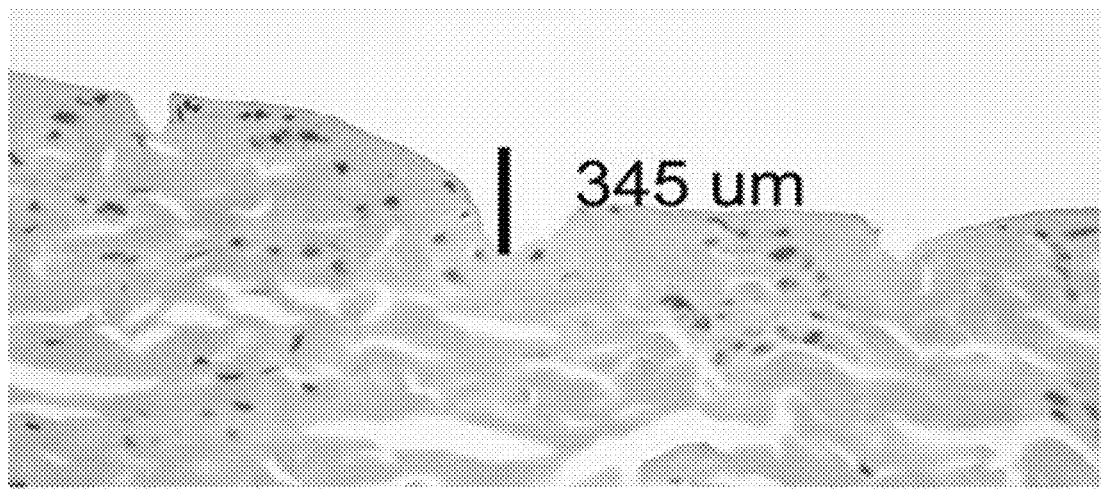
FIG. 13. Preliminary data using cadaveric porcine skin punctured by microneedles formed of PLGA.

Perform Ex Vivo Experiments to Characterize the Optical Performance, Heat Dissipation, and Microneedle Performance for an Integrated UVA1 and NBUVB Flexible Microneedle Waveguide Therapy Patch We determine optimal existing off-the-shelf LEDs for UVB light delivery: Currently, there are several existing manufacturers that offer LEDs with performance characteristics that theoretically meet the requirements for NBUVB and UVA1 phototherapy. The criteria include several requirements. The first and foremost is production of light at a narrow spectrum of activity (~311 nm). The second requirement is the ability to deliver energy at irradiances (1 mW/cm$^2$) that have been previously validated as necessary to deliver a therapeutic effect.[9] The third requirement is that the device can operate in continuous cycle to deliver an effective energy dose of 100 to 500 mJ/cm$^2$. The energy dose varies with patient skin type (fairer skin requires less total energy) and is up-titrated depending on clinical response. For instance, MarkTech Optoelectronics (Albany, NY) offers potential options with LEDs at the 310 nm±5 nm spectrum (FIG. 13). The low profile (4 mm) enables the delivery of up to 1 mW/cm$^2$ as each LED is capable of generating up to 0.8 mW of power. For UVA1, there are multiple potential suppliers. Vishay (Shelton, C) offers numerous micro and mm-scale UVA1 LEDs that re-capitulate the optical parameters of UVA lamps with peak spectral outputs at 360 nm and with irradiance outputs up to 30 mW/cm$^2$.

Testing performance characteristics of off-the-shelf LEDs for UVA and UVB light delivery: Electrical measurements will be performed with a semiconductor parameter analyzer. This will involve measurement of performance changes of UV-LEDs with variations in injection current (mA). The operating parameters of the UV-LEDs will be determined with varying levels of applied current up to the maximum specified by the manufacturer. The optical parameters of the LEDs will be assessed using a high-resolution spectrometer (HR4000, Ocean Optics). The heat generation of each LED will be quantified using mid-wave length infrared thermal imaging (InfraScope, Quantum Focus Instruments). Finally, we will test that the spectral and energy output of the LEDs maintain stability over time. After demonstrating the optical and power performance of available off the shelf UV-LEDs in isolation, we will then move on to assess optimal geometric arrangements. Using a spectrophotometer, we have confirmed the spectral output of Vishay's UVA1 LEDs and have selected these off-the-shelf LEDS to pursue further development. We similarly select and validate NBUVB LEDs. In cases where commercially available UV LEDs do not meet our needs, we can construct appropriate LEDs.

We embed UV LEDs on a flexible silicone substrate: A procedure for fabricating flexible phototherapy devices are described as follows:

1. A single silicon crystal wafer is coated with a layer of poly(methyl methacrylate) and polyimide.

2. With photolithography (AZ P4620 AZ 400 k), the wafer is patterned with a bilayer of copper deposited with an electron beam evaporator (e-beam evaporator, AJA). This technique defines the temperature sensing/heating elements. A second layer of multilayer of titanium, copper, and gold is lithographically patterned to form precise nanometer-thin ribbons and membranes. A second layer of polyimide provides electrical insulation and mechanical strain isolation.

3. Reactive ion etching defines the mesh layout.

4. Water soluble tape (5414, 3M, US) can be used to remove the layout from the silicon wafer.

5. A soft stamp made of an elastomer such as PDMS or silicone (Ecoflex, Smooth-On, USA) ~5 μm in thickness is designed to allow retrieval of the nanoribbons via transfer printing.

6. Incorporation of UV-LEDs patterned within the substrate will first be done manually to enable rapid prototyping. A flip-chip method allows assembly of components interconnected by the nanoribbons.

7. Incorporation of power source either as an integrated coin cell battery or through a wireless power strategy. The Rogers group has done extensive work on the power requirements of flexible devices.[37] A thin flexible, conductive cable (HST-9805-210, Elform) can be bonded to contact pads in the device to connect with external electronics such as additional power sources or data acquisition units.

8. Embed a UV protective covering with incorporation of titanium oxide within the outermost layer of the elastomer (PDMS)[38] of the device for ophthalmologic protection.

9. Adhere base-layer of polymeric microneedle waveguides to the constructed UV LED device.

Figure 9:
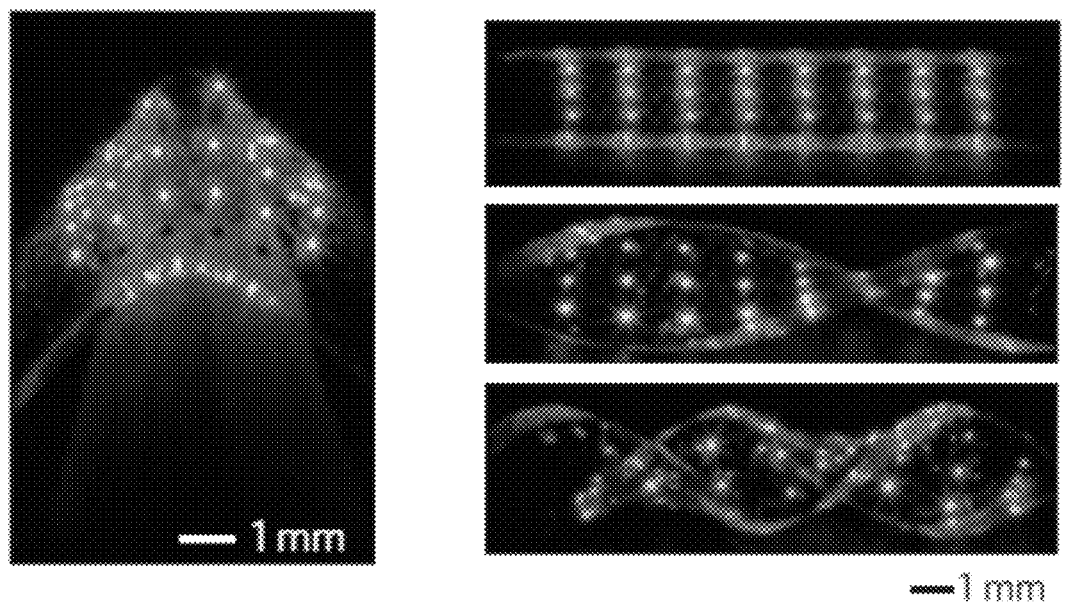
FIG. 9. Demonstration of LEDs (670 nm) in a flexible substrate, useful for facilitating conformal contact to a tissue surface, including a curvilinear surface. See, e.g., Kim, et al. Nat. Mater. 2010, 9, 929.

The nanoribbons can be patterned in both 2-D and 3-D configurations with high throughput. Multiple layers can be added to create more complex devices. The serpentine design of the nanoribbons has been carefully elucidated to enable strain that is biomimetic with the epidermis without loss of performance. With deformation, the system can strain-isolate critical components of the device. Furthermore, the above prototyping techniques are highly scalable to existing fabrication technologies yielding the ability to create flexible light therapy systems at costs low enough to operate as disposable devices. Our preliminary work shown below demonstrates the feasibility of patterning an array of 1.6 mm UVA1 LEDs with copper interconnects. This array has been deployed into a flexible PDMS substrate with an adherent layer of microneedle waveguides composed of PLGA. FIG. 9 demonstrates a prototype device. Further development will involve increasing LED density to ensure adequate light delivery to the surface of the target as well as improving device flexibility to treat curvilinear surfaces.

Characterization of the physical properties of the UVB-LED epidermal, flexible device in bench testing: Optical performance: Using a high-resolution spectrometer (HR4000, Ocean Optics), we will assess the spectral output of the UV LEDs (UVA1 and NBUVB) when embedded within a flexible substrate and adhered to a microneedle waveguide. This is important to ensure that the spectral and power output of the entire system is safe and effective for human testing. We will assess any edge effects and light leakage from the device surface in regards to spectral output. UV light poses an ophthalmological risk. Thus, the adequacy of the protective outer UV-coating must be tested. Mechanical robustness: Protocols to assess the mechanical robustness of flexible electronics have been established previously in the Rogers' laboratory.[35] The lab has a custom uniaxial/biaxial stretcher for inducing controllable deformations. A single lens reflex camera captures deformation and a dynamic mechanical analyzer (TA instruments, Q800) can yield stress/strain curves. A DC source-meter (Model 2400, Keithley) will measure electrical performance with repeated deformation. Temperature safety: Previous works have illustrated that temperatures up to 43° C. is safe in patients for pulse oximeter devices left on for 8 hours or less.[39] The thermal transport characteristics of human skin in vivo have also been previously studied.[40] Thus, experimental modeling can be deployed to ensure adequate heat dissipation within the experimental design. The Roger's laboratory has a thermal imager (FIIR E5) device to ensure real-world thermal safety.

Trial Evaluating the Performance of the UVA1 Flexible Microneedle Waveguide Device for the Treatment of Morphea in Adults.: Morphea is a localized fibrosing skin disease that affects both pediatric and adult patient populations in equal rates at an incidence of up to 2.7 new cases per 100,000 people per year.[41] There are several clinical variants. The appearance of firm, indurated plaques overlying joints or the face can be disfiguring and cause significant morbidity. Systemic therapy with methotrexate or systemic steroids are not ideal for long term therapy given the risk of side effects, particularly in the case of pediatric patients.[42] Topical therapies are only minimally beneficial. UVA1 has been well studied and shown to be effective without the risk of systemic side effects but the lack of availability and patient inconvenience limits its use.[6] Experimental primary endpoints include a validated scale (mLoSSI) for morphea and a Physician Global Assessment of Activity after 15-30 sessions of UVA1 phototherapy.[44] Durometry, a non-invasive device, will also be to quantify tissue hardness between the experimental device and traditional UVA1 phototherapy at 15 and 30 sessions. Finally, histological evaluation of patients graded by a dermatopathologist will be conducted after 30 phototherapy sessions to determine differences in the depth of skin fibrosis between our experimental system and standard of care phototherapy.

There are numerous clinical applications that extend beyond NBUVB and UVA1. For example, modifications of the substrates can enable the deployment of these devices on oral or mucosa surfaces. From a photobiology standpoint, I can use the skills learned here to pursue future, more fundamental work elucidating biological responses of skin in normal and diseased states in response to light delivery of varying wavelengths, pulse structures, irradiances, and dosing times.

REFERENCES FOR EXAMPLE 2

1. American Academy of Dermatology Work, G.; Menter, A.; Korman, N. J.; Elmets, C. A.; Feldman, S. R.; Gelfand, J. M.; Gordon, K. B.; Gottlieb, A.; Koo, J. Y.; Lebwohl, M.; Leonardi, C. L.; Lim, H. W.; Van Voorhees, A. S.; Beutner, K. R.; Ryan, C.; Bhushan, R., *Journal of the American Academy of Dermatology* 2011, 65 (1), 137-74.
2. Wong, T.; Hsu, L.; Liao, W., *J Cutan Med Surg* 2013, 17 (1), 6-12.
3. Lapolla, W.; Yentzer, B. A.; Bagel, J.; Halvorson, C. R.; Feldman, S. R., *Journal of the American Academy of Dermatology* 2011, 64 (5), 936-49.
4. Evans, C., *Am J Manag Care* 2016, 22 (8 Suppl), s238-43.
5. Rachakonda, T. D.; Schupp, C. W.; Armstrong, A. W., *Journal of the American Academy of Dermatology* 2014, 70 (3), 512-6.
6. Teske, N. M.; Jacobe, H. T., *Clin Dermatol* 2016, 34 (5), 614-22.
7. Stege, H.; Berneburg, M.; Humke, S.; Klammer, M.; Grewe, M.; Grether-Beck, S.; Boedeker, R.; Diepgen, T.; Dierks, K.; Goerz, G.; Ruzicka, T.; Krutmann, J., *Journal of the American Academy of Dermatology* 1997, 36 (6 Pt 1), 938-44.
8. Zandi, S.; Kalia, S.; Lui, H., *Skin Therapy Lett* 2012, 17 (1), 1-4.
9. Kemeny, L.; Csoma, Z.; Bagdi, E.; Banham, A. H.; Krenacs, L.; Koreck, A., *Br J Dermatol* 2010, 163 (1), 167-73.
10. Yeung, H.; Wan, J.; Van Voorhees, A. S.; Callis Duffin, K.; Krueger, G. G.; Kalb, R. E.; Weisman, J. D.; Sperber, B. R.; Brod, B. A.; Schleicher, S. M.; Bebo, B. F., Jr.; Shin, D. B.; Troxel, A. B.; Gelfand, J. M., *Journal of the American Academy of Dermatology* 2013, 68 (1), 64-72.
11. Nolan, B. V.; Yentzer, B. A.; Feldman, S. R., *Dermatol Online J* 2010, 16 (2), 1.
12. Passeron, T.; Ortonne, J., *Clinics in Dermatology* 2006, 24 (1), 33-42.
13. Vangipuram, R.; Feldman, S. R., *Oral Dis* 2016, 22 (4), 253-9.
14. Khan, A.; Balakrishnan, K.; Katona, T., *Nature Photonics* 2008, 2, 77-84.
15. Taniyasu, Y.; Kasu, M.; Makimoto, T., *Nature Photonics* 2006, 441, 325-328.
16. Rogers, J. A., *JAMA* 2015, 313 (6), 561-2.
17. Kim, D. H.; Lu, N.; Ma, R.; Kim, Y. S.; Kim, R. H.; Wang, S.; Wu, J.; Won, S. M.; Tao, H.; Islam, A.; Yu, K. J.; Kim, T. I.; Chowdhury, R.; Ying, M.; Xu, L.; Li, M.; Chung, H. J.; Keum, H.; McCormick, M.; Liu, P.; Zhang, Y. W.; Omenetto, F. G.; Huang, Y.; Coleman, T.; Rogers, J. A., *Science* 2011, 333 (6044), 838-43.
18. Sun, Y.; Choi, W. M.; Jiang, H.; Huang, Y. Y.; Rogers, J. A., *Nat Nanotechnol* 2006, 1 (3), 201-7.
19. Kim, D. H.; Ghaffari, R.; Lu, N.; Rogers, J. A., *Annu Rev Biomed Eng* 2012, 14, 113-28.
20. Kim, R. H.; Tao, H.; Kim, T. I.; Zhang, Y.; Kim, S.; Panilaitis, B.; Yang, M.; Kim, D. H.; Jung, Y. H.; Kim, B. H.; Li, Y.; Huang, Y.; Omenetto, F. G.; Rogers, J. A., *Small* 2012, 8 (18), 2812-8.
21. Kim, H.-s.; Brueckner, E.; Song, J.; Li, Y.; Kim, S.; Lu, C.; Sulkin, J.; Choquette, K.; Huang, Y.; Nuzzo, R. G.; Rogers, J. A., *PNAS* 2011, 108 (25), 10072-10077.
22. Meinhardt, M.; Krebs, R.; Anders, A.; Heinrich, U.; Tronnier, H., *J Biomed Opt* 2008, 13 (4), 044030.
23. Doddaballapur, S., *J Cutan Aesthet Surg* 2009, 2 (2), 110-1.
24. Nizamoglu, S.; Gather, M. C.; Humar, M.; Choi, M.; Kim, S.; Kim, K. S.; Hahn, S. K.; Scarcelli, G.; Randolph, M.; Redmond, R. W.; Yun, S. H., *Nat Commun* 2016, 7, 10374.
25. Menter, A.; Korman, N. J.; Elmets, C. A.; Feldman, S. R.; Gelfand, J. M.; Gordon, K. B.; Gottlieb, A.; Koo, J. Y.; Lebwohl, M.; Lim, H. W.; Van Voorhees, A. S.; Beutner, K. R.; Bhushan, R., *Journal of the American Academy of Dermatology* 2010, 62 (1), 114-35.
26. Simpson, G. L.; Yelverton, C. B.; Rittenberg, S.; Feldman, S. R., *Journal of Dermatological Treatment* 2006, 17 (6), 359-361.
27. Luersen, K.; Dabade, T.; West, C.; SDavis, S.; Feldman, S. R., *Journal of Dermatological Treatment* 2014, 25 (6), 478-488.
28. Weng, Q. Y.; Buzney, E.; Joyce, C.; Mostaghimi, A., *Journal of the American Academy of Dermatology* 2016, 74 (6), 1256-9.
29. Karha, P.; Manninen, P.; Hovila, J.; Seppala, L.; Ikonen, E. In *Determination of luminous intensity of light-emitting* diodes with modified inverse-square law., Proceedings of the 9th International Conference on New Developments and Applications in Optical Radiometry., Davos, Switzerland, Grobner, J., Ed. Davos, Switzerland, 2005; pp 211-212.
30. Li, H., *Optik* 2014, 125, 1096-1100.
31. Graaff, R.; Dassel, A. C.; Koelink, M. H.; de Mul, F. F.; Aarnoudse, J. G.; Zijistra, W. G., *Appl Opt* 1993, 32 (4), 435-47.
32. Makadia, H. K.; Siegel, S. J., *Polymers* (Basel) 2011, 3 (3), 1377-1397.
33. Kim, T. I.; Lee, S.; Li, Y.; Shi, Y.; Shin, G.; Lee, S.; Huang, Y.; Rogers, J. A.; Yu, J., *Applied Physics Letters* 2014, 104, 051901.
34. Lu, C.; Li, Y.; Song, J.; Kim, H.; Brueckner, E.; Fang, B.; Hwang, K.-C.; Huang, Y.; Nuzzo, R. G.; Rogers, J. A., *Proc. R. Soc. A* 2012, 468, 3215-3223.
35. Lee, J. W.; Xu, R.; Lee, S.; Jang, K. I.; Yang, Y.; Banks, A.; Yu, K. J.; Kim, J.; Xu, S.; Ma, S.; Jang, S. W.; Won, P.; Li, Y.; Kim, B. H.; Choe, J. Y.; Huh, S.; Kwon, Y. H.; Huang, Y.; Paik, U.; Rogers, J. A., *Proc Natl Acad Sci USA* 2016, 113 (22), 6131-6.
36. Chen, Y.; Chen, B. Z.; Wang, Q. L.; Jin, X.; Guo, X. D., *J Control Release* 2017.
37. Kim, J.; Banks, A.; Xie, Z.; Heo, S.; Gutru, P.; Lee, J.; Xu, S.; Jang, K. I.; Liu, F.; Brown, G.; Choi, J.; Kim, J.; Feng, X.; Huang, Y.; Paik, U.; Rogers, J. A., *Adv. Funct. Mater.* 2015, 25, 4761-4767.
38. Calvo, M. E.; Smirnov, J. C.; Miguez, H., *Journal of Polymer Science Part B: Polymer Physics* 2012, 50, 945-956.
39. Greenhalgh, D. G.; Lawless, M. B.; Chew, B. B.; Crone, W. A.; Fein, M. E.; Palmieri, T. L., *J Burn Care Rehabil* 2004, 25 (5), 411-5.
40. Webb, R. C.; Pielak, R. M.; Bastien, P.; Ayers, J.; Niittynen, J.; Kurniawan, J.; Manco, M.; Lin, A.; Cho, N. H.; Malyrchuk, V.; Balooch, G.; Rogers, J. A., *PLoS One* 2015, 10 (2), e0118131.
41. Fett, N.; Werth, V. P., *Journal of the American Academy of Dermatology* 2011, 64 (2), 217-28; quiz 229-30.
42. Fett, N.; Werth, V. P., *Journal of the American Academy of Dermatology* 2011, 64 (2), 231-42; quiz 243-4.
43. Christen-Zaech, S.; Hakim, M. D.; Afsar, F. S., *Journal of the American Academy of Dermatology* 2008, 59 (3), 385-96.
44. Kelsey, C. E.; Torok, K. S., *Journal of the American Academy of Dermatology* 2013, 69 (2), 214-20.

Example 3: NBUVB

Narrow-band ultraviolet B (NBUVB) phototherapy is an important treatment modality for psoriasis' that yields a relatively high PASI-75 response (60-75%), lacks potential systemic side effects, and is cost-effective.[2-5] However, NBUVB use in physician offices, which has been primarily for moderate-to-severe psoriasis, has decreased in the U.S. by more than 90% in recent history,[6] particularly because of the success of biologics.[7,8] NBUVB is slow, requiring 36 sessions (3 months) before meaningful efficacy is seen, and time until response is a critical factor related to patient-reported improvement in quality of life for psoriasis.[9,10] Second, newer biologic agents (IL-17 and IL-23 inhibitors) exhibit higher PASI-75 scores compared to NBUVB.[11] Third, there is a major access barrier, because office-based treatments require time commitment and travel, may be infeasible for those with mobility issues, and can be costly (each treatment requiring a separate insurance co-pay).[12,13] Despite this, phototherapy remains an important option for psoriasis therapy, especially given its favorable risk-benefit profile.[14] Furthermore, for patients with mild-to-moderate psoriasis or limited involvement after systemic intervention, once to twice daily application of topical corticosteroids with or without vitamin D3 remains typical therapy is burdensome with high rates of patient non-adherence and often incomplete clearance,[15,16] further increasing the need for new approaches.[10]

We provide a novel thin, flexible, and conformable phototherapy device for psoriatic lesions, capable of enhancing the depth penetration of therapeutic NBUVB. The device increases the speed of response and improve overall efficacy, while remaining cost-effective, safe, and convenient. The device includes two main components that can operate in synchrony or separately. The outer layer is a thin, flexible array of micro-NBUVB light emitting diodes (LEDs) embedded within a flexible silicone substrate with circuit interconnects that exactly recapitulate the optical output of standard-of-care systems. Given its flexibility, it can conform to a psoriatic lesion located on any curvilinear location (e.g. elbow or knee). The inner layer adherent to the skin includes a flexible array of transparent, optically-engineered microneedle waveguides (PLGA) with a pre-specified depth (100 μm) that can guide incident NBUVB deeper into the psoriatic lesion. This inner microneedle waveguides can be used separately as an adjuvant for traditional phototherapy to clear recalcitrant lesions. We propose the following Specific Aims:

We have recently developed a flexible, conformable, depth-modulated phototherapy device that delivers UVA-1 (360 nm) to the skin. That system is modified to deliver NBUVB with new LEDs capable of a narrow peak spectral output of 310 nm with lower depth-penetration optimized to penetrate through only the stratum corneum of psoriatic lesions (100 μm).

Validate the bench-top performance of the new flexible, depth-modulated NBUVB phototherapy device for spectral output, mechanical strength, and heat generation in vitro. Success is delivery of 1 mW/cm$^2$ of irradiance with a key spectral output peak at 310 nm.

Safety and efficacy of the NBUVB phototherapy device. We will test the device in 3 psoriasis patients starting NBUVB. Physician assessment of erythema, thickness, and scaling of device-treated vs. standard phototherapy will be performed after each NBUVB session up to 36 sessions. Success will be parallel efficacy to traditional phototherapy and no evidence of adverse events.

Successful completion will produce preliminary data necessary for future NIH grant funding for broader, more wide-scale clinical validation. These results will inform future new designs to target special sites (e.g. hands, feet, scalp), where there is a need for improved NBUVB therapy.

Phototherapy Mechanisms in Psoriasis: NBUVB is thought to reverse the pro-inflammatory cytokine profile in psoriasis by downregulating the Th17 axis,[17] and restoring $T_{reg}$ function by upregulating FOXP3.[18] Another key mechanism involves NBUVB's induction of apoptosis of pathogenic T lymphocytes and keratinocytes.[19] Specifically, activated T-cells target basal keratinocytes that drive epidermal hyperproliferation.[20,21,22] Given the known attenuation of NBUVB intensity with depth, specifically in pathologies in which the stratum corneum is thickened (e.g. psoriasis vulgaris), we hypothesize that controlled, deeper delivery of NBUVB holds significant therapeutic potential. Clinically, in a double-blind randomized trial, high dose of NBUVB resulted in more prolonged remission compared to low dose NBUVB.[23] In regards to safety, a systematic review of NBUVB did not show an increase risk of subsequent cutaneous malignancy.[24]

Limitations of Existing Office and Home-Based Phototherapy Devices: Phototherapy in the office setting is largely delivered via mercury gas lamps (Philips TL01) with spectral filters that are inefficient, have irregular output across the length of the lamp, require high-energy input, and have limited shelf life. Patients with moderate to severe psoriasis typically require 36 sessions requiring 3 months of therapy before meaningful improvement.[25] The medical board of the National Psoriasis Foundation emphasizes treatment goals that lead to significant skin improvement within 3 months,[26] which suggests the need for strategies that decrease NBUVB response time. Although the excimer laser provides therapy targeted to localized areas, the system is highly expensive, poses an ophthalmic risk, and is not suitable for home use.[27] While home NBUVB is associated with higher patient satisfaction, and even cost-effectiveness,[28] the use of home NBUVB faces numerous barriers.[13,28-30] This includes high initial out-of-pocket expenses[12] in purchasing a home unit, medical-legal risk, and provider concern for the need for medical supervision.[31-34] Although these barriers persist, continued concerns regarding the cost of biologics[35,36] and their unknown long-term safety has increased interest in home NBUVB. National Biological® and Daavlin® are established manufacturers offering mercury gas lamp systems (handheld and whole body) for home-use.[37] More recently, Clarify Medical recently earned FDA-clearance in 2017 for a handheld LED-based NBUVB system paired to a smartphone.[38] Psoria-Shield™, though not explicitly marketed as a home-use device, is another FDA-cleared LED-based NBUVB system.[39] While Psoria-Shield™ and Clarify Medical offer NBUVB LEDs with greater robustness and no warm-up time, these systems only recapitulate existing office-based phototherapy modalities without demonstration of increased efficacy or speed until response. Luma™ Therapeutics offers a new approached inspired by Goeckerman therapy by pairing NBUVB with a coal-tar embedded hydrogel patch.[40] However, this system requires an additional topical drug component, risks irritant contact dermatitis, may be inconvenient for patients, and has yet to be validated in larger studies. A phototherapy device suitable for future home use, designed to do more than recapitulate existing systems, would represent a significant advance.

Figure 8:
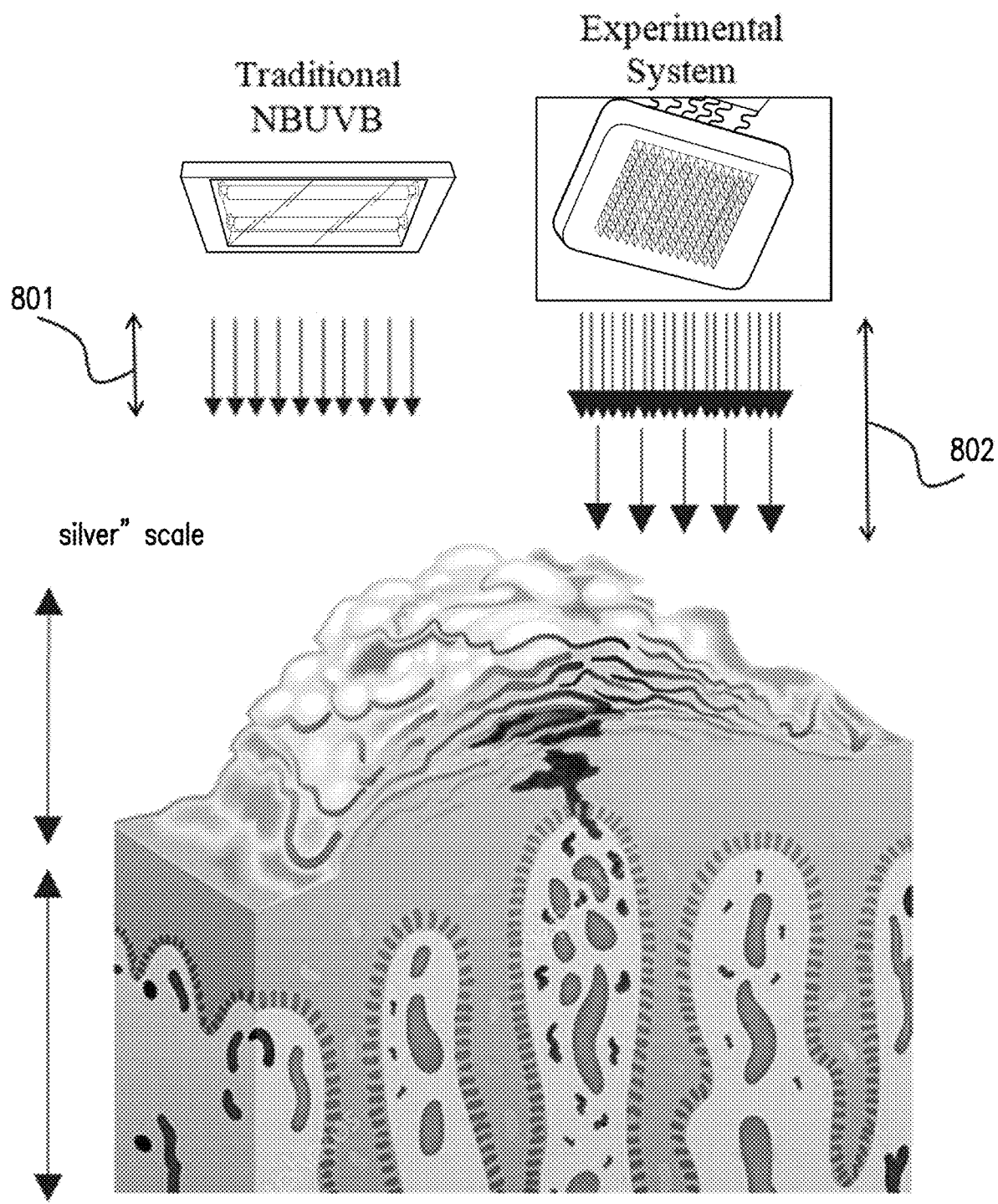
FIG. 8. Traditional NBUVB and Experimental System. Current systems have limited ultra-violet light penetration (compare top left panel penetration depth 801 with top right panel penetration depth 802). The top layer of skin in psoriasis is extra-thickened (see bottom panel), which limits the penetration of the ultra-violet light that treats psoriasis. The devices provided herein are soft and flexible, allowing the device to wrap around a psoriasis spot (e.g., conformal contact) for better light delivery. Also, the devices provided herein can have tiny micro-needles that allow deeper penetration of therapeutic light. They create optical channels in the skin.

Through advancements in materials science and biomedical engineering, it is now possible to create hyper-flexible epidermal electronics that resemble temporary tattoos that adhere to any curvilinear body surface.[41] Leveraging these advances, a flexible epidermal electronics system capable of delivering phototherapy with embedded therapeutic LEDs has the potential to offer more efficacious, faster, and more convenient delivery. We propose a novel system incorporating NBUVB LEDs in a flexible silicone elastomer coupled to polymeric microneedle waveguides optically engineered to allow controlled depth-enhancement of NBUVB delivery for treating psoriasis. Key advantages include:

Faster Response Time with Enhanced Depth Penetration through Microneedle Waveguides: The speed to response from NBUVB requires a balance between adequate UVB irradiance and radiant energy density per area of skin for treatment effect without causing deleterious skin erythema. The advantages of our technology is that the outermost surface of the skin does not receive any additional UVB energy compared to traditional phototherapy systems. However, the microneedles enable delivery of therapeutic NBUVB to affected T lymphocytes and keratinocytes deeper in the epidermis than would otherwise not be treated by conventional systems. For instance, the average penetration of UVB at 305-320 nm is only 30 μm.[42] The stratum corneum thickness of the volar arm is 20 μm,[43] while the palm and soles averages more than 170 μm.[44] Moreover, psoriatic lesions are more than 200% thicker than unaffected skin.[45] We hypothesize that deeper penetration through the stratum corneum of thick psoriatic lesions, particularly on acral skin, will enable faster skin clearance. While previous works have developed implantable polymers to guide laser light to deeper tissues, those devices require a surgical procedure to implant and have been limited to the delivery of longer wavelengths of visible light.[46] Although optical clearing agents (e.g. glycerol, perfluordecalin) that reduce light back-scatter and increase target transparency have been shown to enhance the efficacy of laser-assisted tattoo removal (nanosecond QS 755-$n$ Alexandrite laser),[47,48] these strategies would have minimal effect in enhancing the absorption of the lower wavelengths in the UV spectra (<400 nm).[49] We propose a conservative microneedle waveguide length of 100 μm to penetrate solely through the stratum corneum (SC) on most glabrous skin. Given the short-length of the microneedles, we expect this to be regulated as a non-significant risk Class II medical device by the FDA enabling direct to human studies. For example, non-sterile dermal micro-rollers are available without a prescription for cosmetic purposes up to 4,000 μm (4 mm) in length. See FIG. 8.

Figure 11:
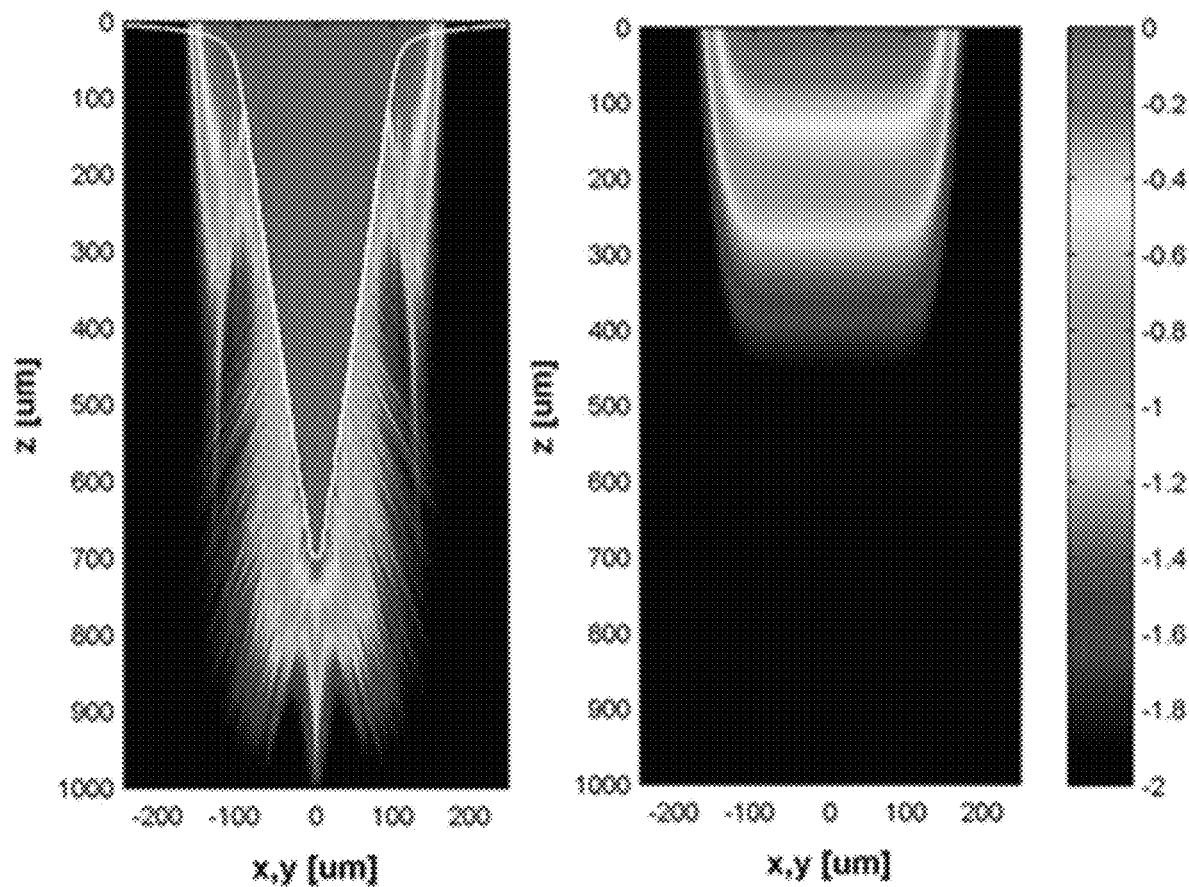
FIG. 11. Depending on the simulation model, results indicate increased light dissipation along the z-axis with a microneedle waveguide (left panel). Without a microneedle waveguide, UVA1 penetrates only 200 microns (right panel). Thus, the devices provided herein significantly increase UVA1 delivery in the z-axis, thereby increasing penetration depth.

Greater Efficacy with Conformability to Curvilinear Body Surfaces: We hypothesize that our ability to wrap circumferentially around a psoriatic lesion will enable improved psoriasis clearance. The hypothesis is based on several fundamental laws of physics governing light delivery. Traditional NBUVB systems require users to stand within a large booth or aim a handheld unit at the lesion. The Lambert cosine law states that the target irradiance ($I_a$) is equal to the irradiance ($I_0$) at normal multiplied by the cosine of the angle from normal; this essentially means that incident UV radiation is most effective when a photon strikes a surface at 90°. Curvilinear surfaces (e.g. knees) creates 'cold spots' for traditional phototherapy systems. Furthermore, peak spectral output of phototherapy lamps is uneven, leaving the lower legs and upper body with less energy delivery. Thus, we hypothesize that intimate integration with the skin through a thin, flexible therapeutic light system will enable more precise and direct delivery of light (FIG. 11).

The device may be 'cut' to size by the patient during home use to a desired geometric shape of the psoriatic lesion. Currently, the energy output of the system is controlled by the current input from the power source and time of operation to recapitulate existing energy delivery algorithms for NBUVB. Future work can deploy the use of an embedded Bluetooth® control unit in the system enabling smartphone based control of the NBUVB microneedle waveguides; prior work in our group demonstrates the feasibility of this in wearable electronics.[50]

Figure 12:
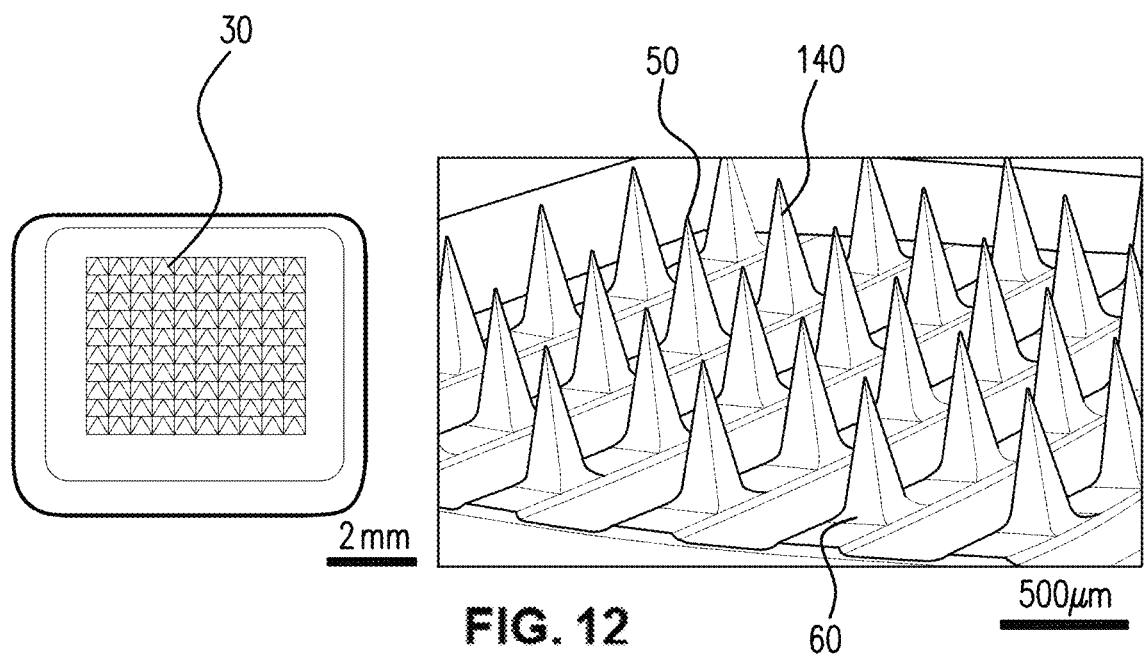
FIG. 12. SEM images of tissue penetrating members, also referred herein as microneedle waveguides, with a view of the entire array (left panel) and a close-up view of a portion of the array.
Figure 14:
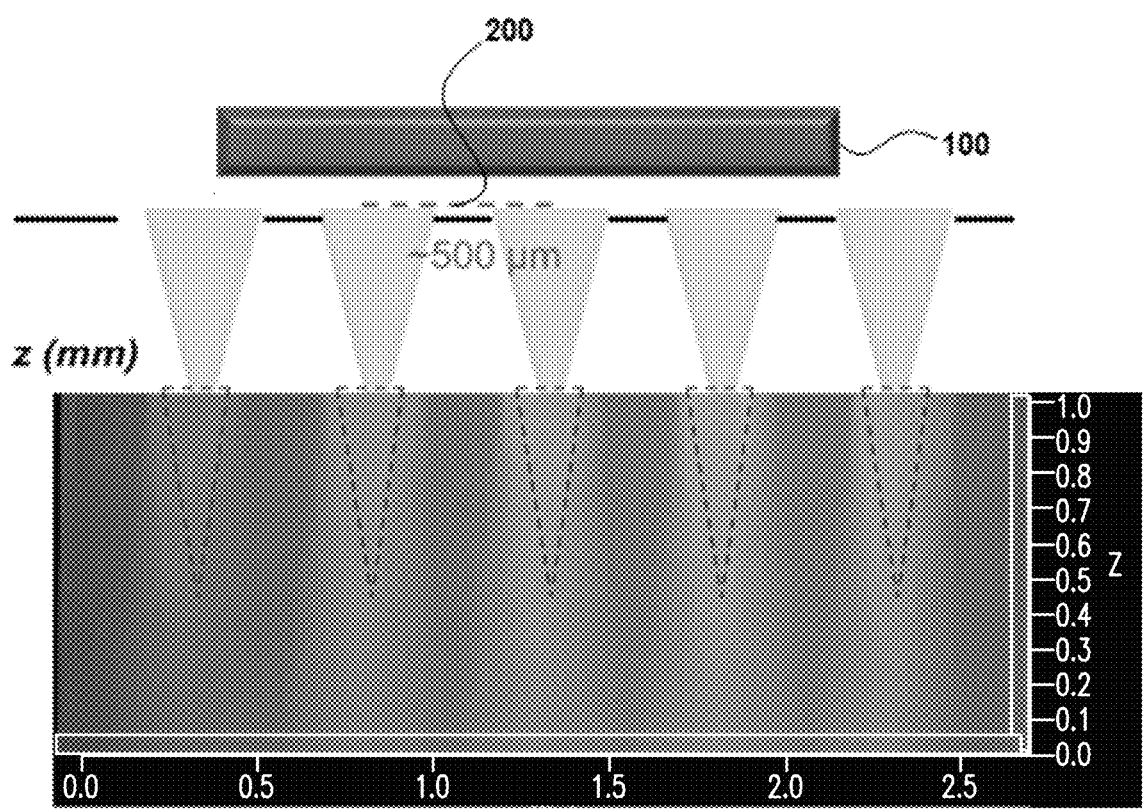
FIG. 14. Agarose gel is used to model skin. Confocal microscopy shows increased fluorescence (green light) created by the PLGA microneedles.
Figure 16:
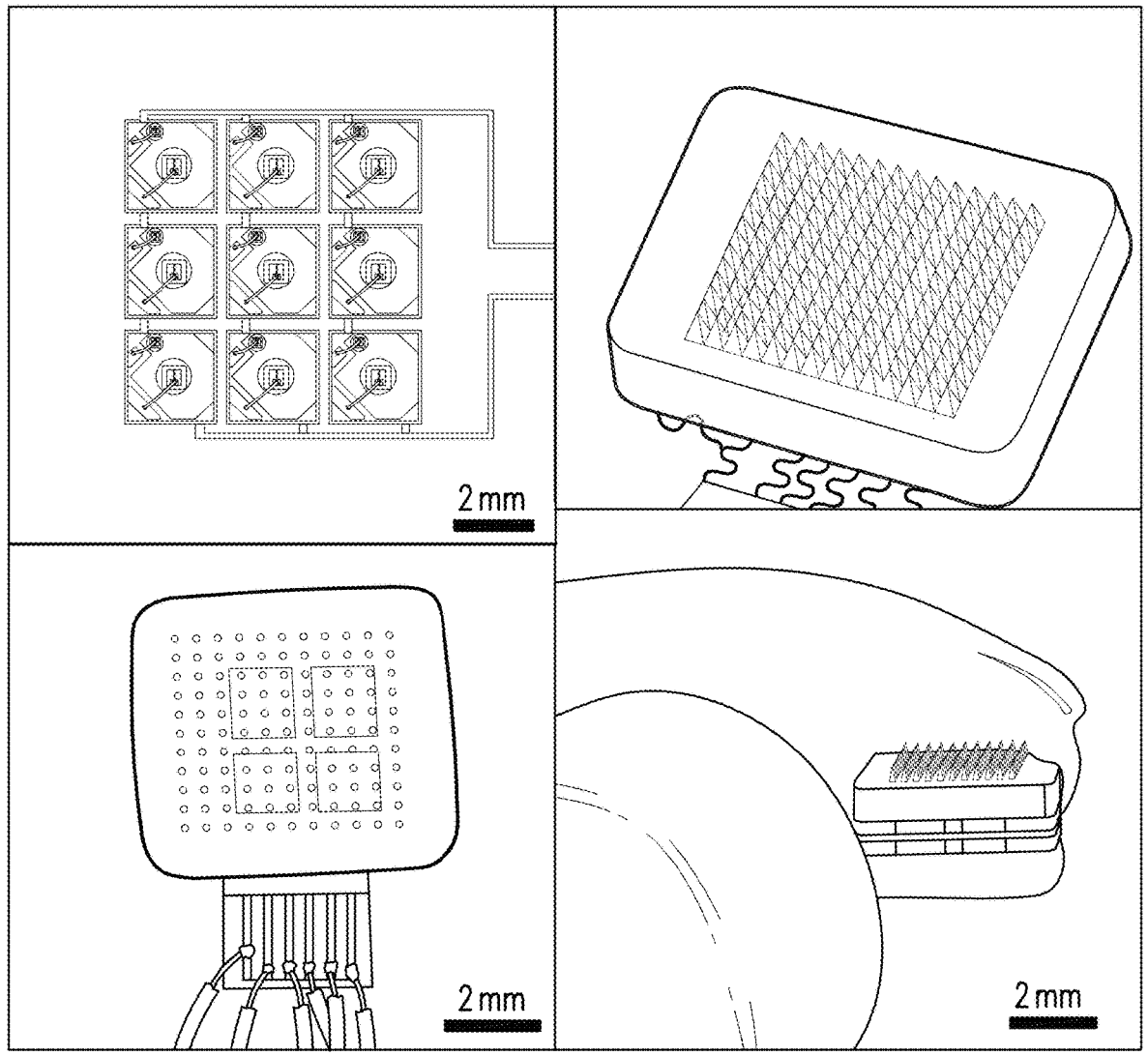
FIG. 16. Device constructed with UVA1 LEDs (Vishay) coupled to PLGA microneedles. A 1×1 cm device demonstrates feasibility. Larger devices with more arrays of LEDs and microneedle waveguides with a larger total surface area are compatible. Scale bar is 2 mm, and bottom right is an image of the device held between fingers.

Demonstration of Optical and Theoretical Modeling to Rationally Design the System: Our preliminary data and studies have shown the feasibility of a similar system for UVA-1 (360 nm) phototherapy. We first employ theoretical modeling using MatLab's (MathWorks, Natick, Mass.) optical simulation toolbox to determine the optimal configuration and composition of microneedles for the delivery of UV-light. The absorption coefficients and scattering coefficients of skin tissue are used for all simulations.[51] In our preliminary data, we demonstrate the simulated light dissipation of UVA-1 across the length of a tetrahedral microneedle (FIG. 11). Minimal modifications to the optical modeling can be employed to determine NBUVB delivery. Identifying the optimal polymer requires consideration of optical transparency, stiffness for skin penetration, and biocompatibility. We have created microneedle prototypes using negative molds of poly lactic-co-glycolic acid (PLGA), given its excellent optical properties and biocompatibility.[52] Below shows preliminary data with an image of the microneedles, and TEM characterization (FIG. 12). In addition, preliminary tests show microneedle channel formation after insertion into cadaveric pigskin. Our preliminary experimental, obtained using agarose gel and confocal microscopy, shows increased lateral and deep light dissipation from the optical channels created by our PLGA microneedles (FIG. 14). We calculate that our microneedles increase UV transmittance by 250-300% in the z-plane along the length of the microneedles. Our UVA-1 prototype demonstrates the feasibility of an integrated system with a top layer of UV LEDs (3×3 and 2×2 arrays) within a flexible silicone substrate, adhered to PLGA microneedle waveguides (FIG. 16).

Experiment Design: Develop a NBUVB phototherapy device. Several manufacturers offer LEDs with performance characteristics that meet the requirements for NBUVB phototherapy (e.g., MarkTech Optoelectronics (Albany, NY) with LEDs at the 310 nm±5 nm spectrum). The low profile (4 mm) enables light irradiance that is comparable to existing NBUVB gas lamp outputs. To fabricate flexible phototherapy devices: i) a circuit print layout is constructed with serpentine copper interconnects to facilitate bending and stretching without breakage; ii) the array of NBUVB LEDs are added; a flexible, conductive cable is bonded to connect to an external battery; iii) the circuitry is embedded within a transparent silicone elastomer (PDMS, 3M); iv) an optical diffuser is added to the base and a UV protective covering (titanium oxide) is added to the top layer[41]; and v) the base layer of PLGA polymeric microneedle waveguides (100 μm), made through a smaller negative mold, is adhered.

Validate the bench-top performance. 1) Optical performance: Using a high-resolution UV radiometer (SolarLight), we will assess the spectral output (nm) and irradiance (mW/cm$^2$) of the NBUVB LEDs when embedded within a flexible substrate and adhered to the microneedle waveguides including edge leakage, and the adequacy of the protective outer UV-coating. 2) Mechanical robustness: our lab has a custom uniaxial/biaxial stretcher for inducing controllable deformations.[53] A single lens reflex camera captures deformation and a dynamic mechanical analyzer (TA instruments, Q800) can yield stress/strain curves. 3) Temperature safety: Temperatures up to 43° C. are safe in patients for pulse oximetry devices worn for <8 hours.[54] Thermal output of the device is measured with 1 hour of continuous operation with a thermal camera (FIR E5).

After validation, we will conduct a 3-arm pilot study evaluating the safety and early efficacy of the experimental system in psoriasis patients (n=3) undergoing NBUVB phototherapy for lesions on glabrous skin. Our goal is to evaluate the safety and early efficacy of the integrated device with NBUVB LEDs and microneedle waveguides (length 100 μm) for psoriatic lesions, and the microneedle waveguides coupled to standard NBUVB compared with standard NBUVB alone. In the Northwestern phototherapy unit, we will choose patients with two symmetrical psoriatic lesions at least 9 cm$^2$ in size on glabrous skin. Within each symmetrical psoriatic lesion, we will identify 2 areas (1 cm$^2$ in size) using anatomical landmarks and sequential photography separated by a border of 2 mm of lesional skin. A medical caliper accurate to 30 μm (Mituyoyo®) will be used to confirm area size. Identify a 1 cm$^2$ area where a 1 cm×1 cm integrated device with NBUVB LEDs (2×2 array) and microneedle waveguides will be placed sequentially. The top layer of the integrated device blocks all UV from the external environment and the device itself. The output of the LEDs will exactly match the settings of the standard phototherapy unit at every session. On the contralateral side, identify a 1 cm$^2$ area where only the microneedle waveguide patch (1 cm×1 cm) will be placed without a UV-blocking layer. Identify a 1 cm$^2$ control area where only standard NBUVB phototherapy is delivered on both symmetrical lesions. The integrated device and microneedle waveguides alone will be applied during each phototherapy session at the same location sequentially for 36 sessions.

After every session, the experimental devices are removed and all 4 locations will be photographed by a research assistant. Then, the 4 locations will be evaluated by 2-blinded dermatologist raters. Each 1 cm$^2$ site will be scored analogously to the PASI-75 for redness, thickness, and scaling on a 0 (none) to 4 (maximum) scale and a physician global assessment (0=clear to 4=severe). After 36 sessions, all 4 sites will be biopsied (4 mm punch) and evaluated histologically by 2 blinded dermatopathologists to quantify epidermal and SC thickness. A baseline biopsy prior to NBUVB initiation will be taken for comparison purposes. The Northwestern's Skin Disease Research Center's Morphology and Phenotyping Core will perform routine histology and IHC staining for CD3 and KRT16. Adverse effects such as erosions, blistering, or dermatitis (scale 0-3) will be evaluated at every session by both raters immediately after device removal and 15 minutes later. In cases where the experimental device leads to skin disruption at 15 minutes, it will be discontinued and the adverse event recorded. We will determine success if the treatment areas evaluated for erythema, thickness, and scaling (0-4) do not exhibit significant differences (one-way ANOVA with pairwise comparisons) after 36 sessions between the microneedle waveguides with the coupled NBUVB LED array, traditional NBUVB with augmentation from the microneedle waveguides, and traditional NBUVB phototherapy alone. If the psoriatic lesion has cleared by rater assessment, NBUVB will be stopped.

Alternative Strategies: Bench testing with our UVA-1 system, which operates at a higher current, shows minimal temperature increase at steady state (<10° C., which is barely noticed). If the heat is too high, we can add a thermal insulating layer or increase LED spacing. Although we have identified PLGA as an ideal polymer, we can also evaluate other polymers (e.g. poly-lactic acid). The microneedle length can be easily modified by adjusting the mold dimensions. The proposed system can treat difficult areas: palms, soles, and the proximal nail fold.

REFERENCES FOR EXAMPLE 3

1. Menter A, Korman N J, Elmets C A, et al. Guidelines of care for the management of psoriasis and psoriatic arthritis: section 4. Guidelines of care for the management and treatment of psoriasis with traditional systemic agents. *Journal of the American Academy of Dermatology.* 2009; 61(3):451-485.
2. Naldi L, Griffiths C E. Traditional therapies in the management of moderate to severe chronic plaque psoriasis: an assessment of the benefits and risks. *Br J Dermatol.* 2005; 152(4):597-615.

3. Staidle J P, Dabade T S, Feldman S R. A pharmacoeconomic analysis of severe psoriasis therapy: a review of treatment choices and cost efficiency. *Expert Opin Pharmacother.* 2011; 12(13):2041-2054.
4. Babalola O, Strober B E. Management of psoriasis in pregnancy. *Dermatol Ther.* 2013; 26(4):285-292.
5. Almutawa F, Alnomair N, Wang Y, Hamzavi I, Lim H W. Systematic review of UV-based therapy for psoriasis. *American journal of clinical dermatology.* 2013; 14(2):87-109.
6. Housman T S, Rohrback J M, Fleischer A B, Jr., Feldman S R. Phototherapy utilization for psoriasis is declining in the United States. *Journal of the American Academy of Dermatology.* 2002; 46(4):557-559.
7. Kimball A, Gauthier G, Hiscock R, Zhang H. Psoriasis Treatment Patterns: Phototherapy, Oral Nonbiologic, and Biologic Therapies. *American Journal of Pharmacy Benefits.* 2015; 7(2):e44-e52.
8. Richard E G, Honigsmann H. Phototherapy, psoriasis, and the age of biologics. *Photodermatol Photoimmunol Photomed.* 2014; 30(1):3-7.
9. Biome C, Simianer S, Purwins S, et al. Time needed for treatment is the major predictor of quality of life in psoriasis. *Dermatology.* 2010; 221(2):154-159.
10. Feldman S R, Goffe B, Rice G, et al. The Challenge of Managing Psoriasis: Unmet Medical Needs and Stakeholder Perspectives. *Am Health Drug Benefits.* 2016; 9(9):504-513.
11. Dong J, Goldenberg G. New biologics in psoriasis: an update on IL-23 and IL-17 inhibitors. *Cutis.* 2017; 99(2):123-127.
12. Nolan B V, Yentzer B A, Feldman S R. A review of home phototherapy for psoriasis. *Dermatol Online J.* 2010; 16(2):1.
13. Cameron H, Yule S, Dawe R S, Ibbotson S H, Moseley H, Ferguson J. Review of an established UK home phototherapy service 1998-2011: improving access to a cost-effective treatment for chronic skin disease. *Public Health.* 2014; 128(4):317-324.
14. Lim H W, Silpa-archa N, Amadi U, Menter A, Van Voorhees A S, Lebwohl M. Phototherapy in dermatology: A call for action. *Journal of the American Academy of Dermatology.* 2015; 72(6):1078-1080.
15. van de Kerkhof P C, Steegers-Theunissen R P, Kuipers M V. Evaluation of topical drug treatment in psoriasis. *Dermatology.* 1998; 197(1):31-36.
16. Brown K K, Rehmus W E, Kimball A B. Determining the relative importance of patient motivations for nonadherence to topical corticosteroid therapy in psoriasis. *Journal of the American Academy of Dermatology.* 2006; 55(4):607-613.
17. Enk C D, Sredni D, Blauvelt A, Katz S I. Induction of IL-10 gene expression in human keratinocytes by UVB exposure in vivo and in vitro. *J Immunol.* 1995; 154(9):4851-4856.
18. Bovenschen H J, van de Kerkhof P C, van Erp P E, Woestenenk R, Joosten I, Koenen H J. Foxp3+ regulatory T cells of psoriasis patients easily differentiate into IL-17A-producing cells and are found in lesional skin. *The Journal of investigative dermatology.* 2011; 131(9):1853-1860.
19. Weatherhead S C, Farr P M, Jamieson D, et al. Keratinocyte apoptosis in epidermal remodeling and clearance of psoriasis induced by UV radiation. *The Journal of investigative dermatology.* 2011; 131(9):1916-1926.
20. Bata-Csorgo Z, Hammerberg C, Voorhees J J, Cooper K D. Kinetics and regulation of human keratinocyte stem cell growth in short-term primary ex vivo culture. Cooperative growth factors from psoriatic lesional T lymphocytes stimulate proliferation among psoriatic uninvolved, but not normal, stem keratinocytes. *The Journal of clinical investigation.* 1995; 95(1):317-327.
21. Bata-Csorgo Z, Hammerberg C, Voorhees J J, Cooper K D. Flow cytometric identification of proliferative subpopulations within normal human epidermis and the localization of the primary hyperproliferative population in psoriasis. *J Exp Med.* 1993; 178(4):1271-1281.
22. Chen G, McCormick T S, Hammerberg C, Ryder-Diggs S, Stevens S R, Cooper K D. Basal keratinocytes from uninvolved psoriatic skin exhibit accelerated spreading and focal adhesion kinase responsiveness to fibronectin. *The Journal of investigative dermatology.* 2001; 117(6):1538-1545.
23. Kleinpenning M M, Smits T, Boezeman J, van de Kerkhof P C, Evers A W, Gerritsen M J. Narrowband ultraviolet B therapy in psoriasis: randomized double-blind comparison of high-dose and low-dose irradiation regimens. *Br J Dermatol.* 2009; 161(6):1351-1356.
24. Archier E, Devaux S, Castela E, et al. Carcinogenic risks of psoralen UV-A therapy and narrowband UV-B therapy in chronic plaque psoriasis: a systematic literature review. *J Eur Acad Dermatol Venereol.* 2012; 26 Suppl 3:22-31.
25. Lapolla W, Yentzer B A, Bagel J, Halvorson C R, Feldman S R. A review of phototherapy protocols for psoriasis treatment. *Journal of the American Academy of Dermatology.* 2011; 64(5):936-949.
26. Armstrong A W, Siegel M P, Bagel J, et al. From the Medical Board of the National Psoriasis Foundation: Treatment targets for plaque psoriasis. *Journal of the American Academy of Dermatology.* 2017; 76(2):290-298.
27. Passeron T, Ortonne J P. Use of the 308-nm excimer laser for psoriasis and vitiligo. *Clin Dermatol.* 2006; 24(1):33-42.
28. Koek M B, Buskens E, van Weelden H, Steegmans P H, Bruijnzeel-Koomen C A, Sigurdsson V. Home versus outpatient ultraviolet B phototherapy for mild to severe psoriasis: pragmatic multicentre randomised controlled non-inferiority trial (PLUTO study). *BMJ.* 2009; 338:b1542.
29. Hung R, Ungureanu S, Edwards C, Gambles B, Anstey A V. Home phototherapy for psoriasis: a review and update. *Clin Exp Dermatol.* 2015; 40(8):827-822; quiz 832-823.
30. Nakamura M, Farahnik B, Bhutani T. Recent advances in phototherapy for psoriasis. *F1000Res.* 2016; 5.
31. Yentzer B A, Feldman S R. Trends in home phototherapy adoption in the US: monetary disincentives are only the tip of the iceberg. *J Dermatolog Treat.* 2011; 22(1):27-30.
32. Koek M B, Buskens E, Steegmans P H, van Weelden H, Bruijnzeel-Koomen C A, Sigurdsson V. UVB phototherapy in an outpatient setting or at home: a pragmatic randomised single-blind trial designed to settle the discussion. The PLUTO study. *BMC Med Res Methodol.* 2006; 6:39.
33. Koek M B, Buskens E, Bruijnzeel-Koomen C A, Sigurdsson V. Home ultraviolet B phototherapy for psoriasis: discrepancy between literature, guidelines, general opinions and actual use. Results of a literature review, a web search, and a questionnaire among dermatologists. *Br J Dermatol.* 2006; 154(4):701-711.

34. Yelverton C B, Kulkarni A S, Balkrishnan R, Feldman S R. Home ultraviolet B phototherapy: a cost-effective option for severe psoriasis. *Manag Care Interface.* 2006; 19(1):33-36, 39.
35. Beyer V, Wolverton S E. Recent trends in systemic psoriasis treatment costs. *Arch Dermatol.* 2010; 146(1): 46-54.
36. Hakim D. Humira's Best-Selling Drug Formula: Start at a High Price. Go Higher. *New York Times* 2018.
37. Zhang P, Wu M X. A clinical review of phototherapy for psoriasis. *Lasers Med Sci.* 2017.
38. K170489-510(k) Clearance: Clarify Medical's Skylit Phototherapy System. In: FDA, ed. Rockville, Md. 2017.
39. Kemeny L, Csoma Z, Bagdi E, Banham A H, Krenacs L, Koreck A. Targeted phototherapy of plaque-type psoriasis using ultraviolet B-light-emitting diodes. *Br J Dermatol.* 2010; 163(1):167-173.
40. Anderson E, Pell C, Dugan S, Martos A, Inventors; Luma Therapeutics, assignee. Phototherapy dressing for treating psoriasis. 2015.
41. Calvo M E, Smirnov J C, Miguez H. Novel Approaches to Flexible Visible Transparent Hybrid Films for Ultraviolet Protection. *Journal of Polymer Science Part B: Polymer Physics.* 2012; 50:945-956.
42. Meinhardt M, Krebs R, Anders A, Heinrich U, Tronnier H. Wavelength-dependent penetration depths of ultraviolet radiation in human skin. *J Biomed Opt.* 2008;13(4): 044030.
43. Bohling A, Bielfeldt S, Himmelmann A, Keskin M, Wilhelm K P. Comparison of the stratum corneum thickness measured in vivo with confocal Raman spectroscopy and confocal reflectance microscopy. *Skin Res Technol.* 2014; 20(1):50-57.
44. Egawa M, Hirao T, Takahashi M. In vivo estimation of stratum corneum thickness from water concentration profiles obtained with Raman spectroscopy. *Acta dermatovenereologica.* 2007; 87(1):4-8.
45. Vaillant L, Berson M, Machet L, Callens A, Pourcelot L, Lorette G. Ultrasound imaging of psoriatic skin: a noninvasive technique to evaluate treatment of psoriasis. *Int J Dermatol.* 1994; 33(11):786-790.
46. Nizamoglu S, Gather M C, Humar M, et al. Bioabsorbable polymer optical waveguides for deep-tissue photomedicine. *Nat Commun.* 2016; 7:10374.
47. Biesman B S, Costner C. Evaluation of a transparent perfluorodecalin-infused patch as an adjunct to laser-assisted tattoo removal: A pivotal trial. *Lasers Surg Med.* 2017; 49(4):335-340.
48. Biesman B S, O'Neil M P, Costner C. Rapid, high-fluence multi-pass q-switched laser treatment of tattoos with a transparent perfluorodecalin-infused patch: A pilot study. *Lasers Surg Med.* 2015; 47(8):613-618.
49. Jansen E D, Pickett P M, Mackanos M A, Virostko J. Effect of optical tissue clearing on spatial resolution and sensitivity of bioluminescence imaging. *J Biomed Opt.* 2006; 11(4):041119.
50. Liu Y, Norton J J, Qazi R, et al. Epidermal mechano-acoustic sensing electronics for cardiovascular diagnostics and human-machine interfaces. *Sci Adv.* 2016; 2(11): e1601185.
51. Graaff R, Dassel A C, Koelink M H, de Mul F F, Aarnoudse J G, Zijlstra W G. Optical properties of human dermis in vitro and in vivo. *Appl Opt.* 1993; 32(4):435-447.
52. Makadia H K, Siegel S J. Poly Lactic-co-Glycolic Acid (PLGA) as Biodegradable Controlled Drug Delivery Carrier. *Polymers* (Basel). 2011; 3(3):1377-1397.
53. Lee J W, Xu R, Lee S, et al. Soft, thin skin-mounted power management systems and their use in wireless thermography. *Proc Natl Acad Sci USA.* 2016; 113(22): 6131-6136.
54. Greenhalgh D G, Lawless M B, Chew B B, Crone W A, Fein M E, Palmieri T L. Temperature threshold for burn injury: an oximeter safety study. *J Burn Care Rehabil.* 2004; 25(5):411-415.

UVB and UVA Biological Activity:

UVB (290 nm to 320 nm) induces apoptosis: programmed cell death in T lymphocytes, keratinocytes and antigen presenting cells; Immunosuppressive: decreases TNF-α, IFN-γ, IL-17, IL-22 (all pro-inflammatory); Increases IL-10 (immunosuppressive cytokine); field effect extends beyond clinical lesions; Side effects: skin erythema; skin cancer pathogenesis UVA (320 nm to 400 nm): Induces apoptosis (B & T cells) via stimulation of superoxide anions and singlet oxygen species (depolarizes mitochondrial membrane); Unique in that it stimulates immediate apoptosis; Immunosuppressive by decreasing TNF-α, IL-12, IFN-γ (both are pro-inflammatory), and ICAM-1 (trafficking of immune cells to tissue); Anti-fibrotic by stimulating collagenase expression; Vasodilatory: stimulates release of nitric oxide (NO) from keratinocytes via photolabile intracutaneous NO metabolites which diffuse to capillary vessels; Side effects: hyperpigmentation, photoaging, skin cancer pathogenesis. See, e.g., International Journal of Dermatology 2010, 49, 623-630; J Cutan Med Surg 2013, 17, 6-12.

UVA liberates NO from photolabile intracutaneous NO metabolites. A fraction of the highly mobile NO diffuses toward the outer surface, where it escapes into the ambient atmosphere. (This fraction is detectable with the airtight skin chamber.) Another NO fraction diffuses to deeper tissue layers, where it enters the capillary vessels and enhances local levels of RS-NO.

Low level light therapy (400 nm to 1400 nm) uses coherent (laser) or non-coherent sources (LEDs); Growing evidence suggests coherent light sources is not important for effect; Photobiomodulation mechanism not even close to being elucidated fully; Biphasic behavior: "Goldilocks" problem; Absorption of light causes photo-dissociation of inhibitory NO from cytochrome c oxidase (respiratory chain transmembrane protein in mitochondria); This increases production of ATP; modulation of reactive oxygen species; induces transcription factors (NF-kB, p53 cAMP, HIF); Seems to stimulate cellular metabolic activity; Immune cells e.g. lymphocytes, fibroblasts (produces collagen); Hemoglobin and melanin have absorption bands 600-1070 nm; 600-700 nm for treating superficial tissue; 780-950 nm for deeper targets; Dosimetry: Irradiance and total fluence delivered both important. See, e.g., Ann Biomed Eng. 2012 February; 40(2): 516-533.

Medicine: appropriate wavelength selected for the target application; Dose: irradiance (mW/cm$^2$), radiant exposure (J/cm$^2$), pulse structure; Delivery: substrate, lateral spread and penetration depth; Heat: avoiding burns but using it as a secondary therapeutic modality; Target size: μLEDs for highly specific targets (single lesions); Larger arrays for field treatments Silicone Sheeting: Proposed Mechanisms in Wound healing; Silicone gels for scarring: typically lightly cross-linked PDMS chains (H-bridges); Ability to provide improved occlusion (thus extension of hydration) similar to normal skin; prevents evaporative water loss from the impaired skin barrier; Transfer tension from the lateral edges of the wound bed to the silicone sheeting; Cooling effect of silicone reduces hyperemia and excess vasodilation; Free silicone diffuses to top layer of skin->unclear biological significance Optical Tissue Clearing: Enables surface-application of biocompatible substances to increase depth of light; Allows us greater optical efficacy regardless of needle depth/density; Immersion of tissues into optical-clearing agents (OCAs) that reduces the scattering of tissue and make tissue more transparent; Glycerol (safe—biocompatible); Polyethylene glycol (commonly used in cosmetics); Perfluorodecalin; DMSO (biocompatible); Thiazone (chemical enhancer—some irritation)

Perfluorodecalin (PFD) Patch: Reduce Optical Scatter; Biocompatible fluorocarbon liquid with high optical transparency (UV to IR); Low surface energy—rapidly wicks into porous materials; Used for detached retinas; Absorbs half of its liquid volume of gaseous oxygen—investigated as a hemoglobin substitute; Refractive index of skin: 1.44 to 1.42 depending on wavelength of light; Refractive index of perfluorodecalin is 1.31; silicone gel is 1.40; good optical matching; Reduces optical scattering from keratinocytes—increases depth of penetration and energy delivery of light into the skin for tattoo removal; Peruorodecalin reduces optical scattering or the scattering of light from microbubbles and skin cells, thus increasing the depth of the penetration and energy delivery of light into the skin to shatter more ink particles trapped in the dermis Light-Tissue Interactions: Flexible light therapy systems intimately connected to skin reduces surface reflectance (tissue follows Snell's law); Coefficient $\mu_a$ (cm$^{-1}$) characterizes tissue absorption; Coefficient $\mu_s$ (cm$^{-1}$) characterizes tissue scatter ($1/\mu_s$=mean free path length until the next scattering event); Scattering is not isotropic in biological tissue; Forward scattering is predominant in biological tissue; Anisotropy factor (g) ranges from 0 to 1; in tissue vary from 0.8 to 0.99:

$$\mu'_s = \mu_s(1-g)$$

The sum of $\mu_s$ and $\mu_a$ is called the total attenuation coefficient $\mu_t$ (cm$^{-1}$): $\mu_t = \mu_s + \mu_a$ Transport theory: radiance L(r,s) of light at position r traveling in direction of unit vector s is decreased by absorption and scattering; Radiance is a radiometric measure: describes the amount of light that passes through or is emitted from a particular area; falls within a given solid angle in a specific direction $$s \cdot \nabla L(r,s) = -(\mu_a + \mu_s)L(r,s) + \mu_s \int_{4\pi} p(s,s')L(r,s')d\omega'$$

Depth and Spread: Optimize microneedle length to enable full depth delivery; Full treatment of dermis would be ~2.5 mm depending on location (assumes 0.5 mm additional depth penetration); Consider options to minimize epidermal light exposure; deliver light in only at specific layers; Maximize microneedle density to enable axial light delivery; Consider methods to allow light dissipation across length of needle Pulse Structure: There have been some reports that pulse structure is an important factor in LLLT; some have found better effects using 1 or 2 Hz pulses than 8 Hz or CW 830 nm laser on rat bone cells, but the underlying mechanism for this effect is unclear FIG. 36 Novel Microneedle Designs: Heat insulated and opaque at the top (0.1 mm) of the needle with thicker silicone coating->protects epidermis from injury and post-inflammatory hyperpigmentation; Heat conductive and transparent bottom (0.1-0.5 mm) without coating->allows light delivery The devices may be used in a medical or beauty application.

UVA+Waveguides: Morphea: A localized sclerotic disease that can cause significant disfigurement among both pediatric and adult patients; UVA is highly effective but: Low availability of UVA units; Patients at increased risk of skin cancer; systematic tanning; Clinical need: ability to apply UVA directly to the skin lesion; preferably in a home setting with an auto-shut off mechanism.

UVA+Heat: Digital Ischemia: Distal perfusion issues remain a major unmet clinical need with pharmacological interventions of minimal benefit; Minimal modification of morphea UVA device; but optimize for more heat generation (DC drive the LEDs); Broad applications with tremendous unmet needs; Applications: digital ischemia ulcers (systemic sclerosis, chronic renal failure, Raynaud's phenomena), vasopressor induced necrosis (ICU setting), chronic vascular dysfunction (peripheral vascular disease), wound healing.

Cutaneous T-Cell Lymphoma: Malignant cells are exquisitely sensitive to NBUVB; it is standard of care for Stage IA (patch stage); The disease often progresses to plaque/tumoral stage where NBUVB does not penetrate; Opportunity to utilize existing NBUVB systems but apply disposable microneedle waveguides on thicker tumoral lesions; Require greater depth and maximum tissue density.

Interventional Cardiology: UVA; microUVA embedded guidewire that vasodilates as it extends into narrower coronary vessels; New class of coronary stents that will reduce restenosis without drugs. UV LEDs can be vasodilatory, thereby providing a non-pharmacological method to vasodilate blood vessels.

LLLT+Waveguides+Heat: Pain; U.S. faces an opioid pain crisis; Pediatric pain remains poorly managed; Many localized pain syndromes; Longer wavelengths (~800 to 900 nm) and higher output powers (to 100 mW) have been preferred in therapeutic devices for deeper tissue penetration; In 2002, MicroLight Corp received 510K FDA clearance for a 830 nm diode laser for the treatment of carpal tunnel syndrome; Acupuncture—growing body of evidence for needle modulation of local pain; selected locations of anatomical importance; Heat—long history as a therapeutic modality to reduce pain.

Low Level Light Therapy: Acne Vulgaris; Several systematic studies demonstrate LLLT efficacy in acne vulgaris; *P. acnes* destroyed via activation of protoporphyrin IX->ROS; Blue LED (400-500 nm)—77% improvement; Red LED (620-660 nm)—66% improvement; 10-200 mW/cm$^2$; 2-60 J/cm$^2$; Better efficacy vs. 5% benzoyl peroxide; Target: deep, cystic lesions that occur 2-4 times monthly; painful—too deep for topical medications; Commonly occurs in pregnant women (hence need for safe light based system); Parameters: 10-200 mW/cm$^2$; 2 J/cm$^2$-60 J/cm$^2$.

Low Level Light Therapy: Periorobital Rhytides: Microneedling works to stimulate collagen neogenesis through the creation of micro-puncture wounds; Some studies show equivalence to fraxel laser ablation; Needle pitch, width, and length (0.5 mm to 4 mm) are all variable; Heat likely plays a role in efficacy; Parameters: 10-200 mW/cm$^2$; 2 J/cm$^2$-60 J/cm$^2$ Low Level Light Therapy: Periorbital Rhytides: Dissolvable single-use microneedle patches with LEDs for localized periorbital rhytides; Heat production is beneficial->one underlying mechanism of RF (but much higher heating here); consider addition of dye to disperse heat from the optical energy. Challenge of dumping heat into the epidermis. Parameters: 10-200 mW/cm$^2$; 2 J/cm$^2$-60 J/cm$^2$ NBUVB+Waveguides for Nails; Predominantly a penetration problem for phototherapy and topical medicines; Nail has significantly higher modulus; Implications for a wide range of nail diseases (major need)

Injectable, Cellular-Scale Optoelectronics with Applications for Wireless Optogenetics, including flexible electronics on balloon catheters Opportunity space is vast: new treatment modality with broad applications across clinical medicine and aesthetics, including:

UVA-1 waveguides for morphea.

UVA-1 waveguides+heat: distal perfusion problems.

UVA-1 for interventional cardiology applications.

LLLT waveguides+heat: regional cutaneous pain syndromes (or part of nerve cuffs).

LLLT waveguides (485 nm & 640 nm): cystic acne lesions; Broad applications for other deep infectious or inflammatory etiologies.

LLLT waveguides+heat: (830 nm) for periorbital rhytids; Broad applications for other aesthetic problem areas.

NBUVB waveguides (311 nm) for nail psoriasis; Broad applications for other nail pathologies, rigid topographies (bone).

Scars: Keloids and Hypertrophic Scarring: $16 billion dollar problem: burns, piercings, accidents, post-surgical scars; Similarly, an abnormal hyper-fibrosis of injured skin; Current standard of care: silicone gel sheeting (3 RCTs in 186 patients show benefit); Small studies showing benefit of infrared LED devices (805 nm); Mechanical effects: microneedling reduces and softens smaller acne scars; Our combination of silicone+light therapy+microneedles can be applied to both morphea and keloids. 30 days with an infrared LED device (805-nm at 30 mW/cm2) and showed significant improvement with no associated side effects as evidenced by improvements in VSS score, measurement of scar height by quantitative skin topography, and blinded clinical assessment of photographs. See, e.g., Barolet D, Boucher A. Prophylactic low-level light therapy for the treatment of hypertrophic scars and keloids: a case series. Lasers in surgery and medicine. 2010; 42:597-601. [PubMed: 20662038].

Example 4: Microneedle Light Guides for Integrated Wearable Devices to Enhance UV Delivery for Deep Skin Applications There are many biological applications for light therapy, including medical therapeutic applications such as photothermal, photochemical (generation of free radicals and isomerization) and photobiological (cell stimulation). A common issue, however, is ensuring the appropriate light wavelength and intensity is delivered to the desired tissue region. On a skin surface, this is not an issue. In deeper tissue (e.g., below the epidermal layer, such as at a depth greater than 50 µm, 75 µm or 150 µm to about 3 mm, or sub-ranges thereof), however, where the epidermis can act as a light barrier, this is a significant limitation. Conventional tissue illumination, such as by medical lamps, suffer from the fundamental limitation that both affected and healthy skin tissues are exposed. This is particularly problematic for light that itself that has a risk factor of adversely impacting healthy tissue, including UV light.

The devices and methods presented herein address this issue by providing a type of waveguide to light that generates a well-defined exposure region, including a three-dimensionally defined exposure region where both tissue depth and tissue area are well-controlled. Accordingly, any of the devices and methods described herein may be characterized as providing a controlled depth illumination, in terms of maximum penetration depth from the surface (e.g., up to 5 mm, up to 4 mm, up to 3 mm, up to 2 mm, and any subranges thereof). Furthermore, the controlled depth illumination may be described in terms of slice of tissue from the tissue surface, such as between 50 µm and 5 mm, 150 µm and 3 mm, or 150 µm and 2 mm, and any subranges thereof. Similarly, the illumination area footprint, which is dependent on the array of microneedles footprint, can be controlled by the geometrical configuration, spacing and density of microneedles and optical light sources. By activating every individual light source of an array of optical light sources, such as every LED that forms the overall light source, maximum footprint and intensity is achieved. By activating fewer light sources in the array, the illumination footprint and/or intensity is controlled.

Accordingly, provided herein is a robust and powerful platform to tailor the device and method to the application of interest, including a desired therapeutic area and/or therapeutic volume underlying a tissue surface. In this manner, the light delivery is tailored to the desired tissue, thereby minimizing light delivery to healthy tissue, and decreasing power load requirement of the device. This provides a fundamental biological improvement of minimizing unwanted exposure to healthy tissue (even for enhanced light delivery in deep skin) and providing the ability to power the device with an on-board power source (e.g., a battery) to facilitate device wearability and freedom of movement of the patient.

Fabrication scheme: An exemplary method of making an array of polymeric microneedles is illustrated in FIG. 36. Provided herein are fabrication schemes that involve melt-molding of biocompatible polymers. A material, such as polydimethylsiloxane (PDMS), is patterned, including by laser etching to provide laser-ablated PDMS molds. Poly (lactic-co-glycolic acid) PLGA is placed on top of the mold, including PLGA pellets. Under high-temperature (about 180° C.) and vacuum (about 25 inches of mercury), the PLGA flows into the mold recess features. Temperature is reduced and the PLGA material separated from the mold, thereby providing a microarray of microneedles. The molds may be reused.

FIG. 37 illustrates high quality microscale light guides are made from the fabrication scheme, including in the form of a 12×12 pyramidal microneedle array. There is negligible light loss in the guides (FIG. 38).

The dimensions of the microneedles are readily tunable. FIG. 39 are photographs of various densities of microneedles, including 44% (left panel), 56% (middle panel), and 64% (right panel) occupancy. Relatively longer microneedles, such as 1 mm, can have increased occupancy. Microneedle length, however, is variable, including lengths between 0.5 mm to 2 mm, for light delivery at target depths.

LEDs may be assembled on polyimide substrates with laser-cut or photolithographically defined interconnects. FIG. 40 illustrates high performance LEDs (e.g., UVA) having a footprint of 1.6×1.6×1.4 mm with a corresponding emission spectrum. Suitable optical power is generated with mild increases in temperatures.

The devices provided herein are characterized by well-defined light intensity distribution, including a uniform light intensity (FIG. 41A-41B) with high flexibility to facilitate conformal contact with curvilinear surfaces (FIGS. 41C-

41E). FIG. 42 further illustrates the mechanical properties of the devices provided herein, suitable for soft, conformal contact with skin, with a bending radius of up to 3.5 mm (top panel). Solvent treatments provide microneedles with extremely flexible substrate layers (FIG. 42 middle and bottom panels). The relatively hard needles (FIG. 43A) effectively penetrate skin (FIG. 43B), including with an insertion depth that averages 0.73±0.04 mm (n=10), which is over 70% of the needle length.

The dermal penetrating members provided herein enhance light delivery to deep tissue, including in deep skin. This is demonstrated in a gel phantom that is optically similar to human skin. Use of PLGA microneedles increase light penetration depth in turbid, skin-mimicking media compared to an identical control but without microneedles. Quantification of light intensity by Monte Carlo simulations (360 nm decay in skin) is provided in FIG. 44. Greater than 3-times power is delivered in deep skin (e.g., below 500 µm from the skin surface).

Computational models are validated using a UV photoactivated dye doped phantom. Microneedles are inserted into the phantom and light generated. FIG. 45A-45B illustrates the experimentally-obtained result (FIG. 45A) matches the computationally determined results (FIG. 45B) for both without microneedles (top panels) and with microneedles (bottom panels).

FIG. 46A-46B is a photograph of a device laminated on ex-plant human skin tissue. FIGS. 46C-46D are experimental results of cell damage at 13.5 $J/cm^2$ and 67.5 $J/cm^2$ for conventional lamps and the instant microneedle devices (MN). Cleaved caspase 3 is a biomarker for UV toxicity. The UV LED patches deliver less light in the epidermis, with a corresponding lower level of damaged cells.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a numerical range, a wavelength range, a power range, a light intensity range, a transmission range, a length or width range, a pitch distance range, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A light delivery device for delivering light to a tissue of a patient, the light delivery device comprising:
   a tissue penetrating member having a distal end and a proximal end, the tissue penetrating member configured to to be inserted into the tissue, wherein the tissue penetrating member is at least partially optically transparent along a surface of the tissue penetrating member positioned between the distal end of the tissue penetrating member and the proximal end of the tissue penetrating member to provide optical transmission of at least a portion of the light through the surface of the tissue penetrating member, thereby allowing at least the portion of the light to be delivered into the tissue of the patient when the tissue penetrating member is inserted into the tissue, wherein the tissue penetrating member has an effective Young's modulus selected to withstand stresses during insertion through a tissue surface without substantial deformation in a direction that decreases penetration depth in the tissue; and
   a substrate that supports the tissue penetrating member.

2. The light delivery device of claim 1, comprising:
   a plurality of tissue penetrating members comprising the tissue penetrating member, the plurality of tissue penetrating members being configured to penetrate the tissue of the patient and being at least partially optically transparent.

3. The light delivery device of claim 2, comprising:
   an array of microneedles comprising the plurality of tissue penetrating members.

4. The light delivery device of claim 3, further comprising:
   an array of optical sources optically aligned with the array of microneedles.

5. The light delivery device of claim 3, wherein a microneedle of the array of microneedles has a geometrical shape that is tetrahedral, square, pyramidal, or conical.

6. The light delivery device of claim 2, wherein a tissue penetrating occupancy fraction of the plurality of tissue penetrating members is between 0.05 and 0.9.

7. The light delivery device of claim 1, further comprising:
   an optical source in optical communication with the tissue penetrating member, the optical source configured to emit the light.

8. The light delivery device of claim 7, wherein the optical source has an emission maximum in a visible range or an ultraviolet range of the electromagnetic spectrum.

9. The light delivery device of claim 7, wherein the optical source is removably connected to the tissue penetrating member.

10. The light delivery device of claim 9, comprising:
    a tissue contacting unit comprising the tissue penetrating member and the substrate, wherein the tissue contacting unit is disposable.

11. The light delivery device of claim 1, wherein the tissue penetrating member has a length that is no less than 100 µm and that is no more than 10 mm and/or a pitch distance that is greater than or equal to 100 µm and less than or equal to 1 mm.

12. The light delivery device of claim 1, wherein the tissue penetrating member is tapered, the tissue penetrating member having a maximum width at the proximal end of the tissue penetrating member and a minimum width at the distal end of the tissue penetrating member.

13. The light delivery device of claim 12, wherein the maximum width of the tissue penetrating member is no less than 100 µm and is no more than 1 mm.

14. The light delivery device of claim 1, wherein the tissue penetrating member is formed of a biocompatible material, wherein the biocompatible material comprises a polymer.

15. The light delivery device of claim 1, wherein the tissue penetrating member is solid.

16. The light delivery device of claim 1, further comprising:
    an optical dispersion element in optical communication with at least one tissue penetrating member, the optical dispersion element comprising at least one of:
    (i) a roughened tissue penetrating member surface;
    (ii) an optical coating;
    (iii) a diffraction grating;
    (iv) a waveguide;
    (v) a chemically-modified tissue penetrating member surface;
    (vi) a patterned optically opaque layer;
    (vii) lenses; or
    (viii) upconverting or downconverting phosphors.

17. The light delivery device of claim 1, further comprising:
    a light intensity modulator for controlling an intensity of at least the portion of the light transmitted through the tissue penetrating member as a function of a depth of the distal end of the tissue penetrating member from a surface of the tissue.

18. The light delivery device of claim 17, wherein the light intensity modulator comprises a non-transparent coating extending from the proximal end of the tissue penetrating member to a tissue surface region of the tissue penetrating member.

19. The light delivery device of claim 1, further comprising a bioactive agent releasably connected to the tissue penetrating member, wherein the bioactive agent is activated by light transmitted by the tissue penetrating member.

20. A method of delivering light to a tissue of a patient, the method comprising:
    contacting one or more tissue penetrating members of a light delivery device with the tissue of the patient;
    inserting the one or more tissue penetrating members into the tissue of the patient; and
    delivering the light through the one or more tissue penetrating members to the tissue of the patient while the one or more tissue penetrating members are inserted into the tissue of the patient,
    wherein the one or more tissue penetrating members have an effective Young's modulus selected to withstand stresses during insertion through a tissue surface without substantial deformation in a direction that decreases penetration depth in the tissue.

21. The method of claim 20, wherein:
    the light delivery device comprises an array of tissue penetrating members and an optical source;
    said inserting the one or more tissue penetrating members into the tissue of the patient comprises:
        inserting the array of tissue penetrating members into the tissue of the patient; and
    said delivering the light through the one or more tissue penetrating members to the tissue of the patient comprises:

operating the optical source of the light delivery device to deliver the light through the array of tissue penetrating members.

\* \* \* \* \*